United States Patent
Pfizenmaier et al.

(10) Patent No.: US 8,927,205 B2
(45) Date of Patent: Jan. 6, 2015

(54) RECOMBINANT POLYPEPTIDES OF THE MEMBERS OF THE TNF LIGAND FAMILY AND USE THEREOF

(75) Inventors: Klaus Pfizenmaier, Tiefenbronn (DE); Peter Scheurich, Stuttgart (DE); Ingo Grunwald, Bremen (DE); Anja Krippner-Heidenreich, Newcastle upon Tyne (GB)

(73) Assignee: Universitat of Stuttgart, Stuttgart (DE)

( * ) Notice: Subject to any disclaimer, the term of this patent is extended or adjusted under 35 U.S.C. 154(b) by 1137 days.

(21) Appl. No.: 10/594,189

(22) PCT Filed: Mar. 24, 2005

(86) PCT No.: PCT/EP2005/003158
§ 371 (c)(1),
(2), (4) Date: Jul. 13, 2007

(87) PCT Pub. No.: WO2005/103077
PCT Pub. Date: Nov. 3, 2005

(65) Prior Publication Data
US 2007/0286843 A1  Dec. 13, 2007

(30) Foreign Application Priority Data
Mar. 26, 2004 (DE) .......................... 10 2004 014 983

(51) Int. Cl.
*G01N 33/48* (2006.01)
*G01N 33/49* (2006.01)
*G01N 33/50* (2006.01)
*G01N 33/53* (2006.01)
*G01N 33/543* (2006.01)
*C07K 14/525* (2006.01)
*A61K 45/06* (2006.01)
*C07K 14/705* (2006.01)
*C07K 16/40* (2006.01)
*G01N 33/544* (2006.01)
*G01N 33/68* (2006.01)
*A61K 38/00* (2006.01)

(52) U.S. Cl.
CPC .............. *C07K 14/525* (2013.01); *G01N 33/53* (2013.01); *A61K 45/06* (2013.01); *C07K 14/70575* (2013.01); *C07K 16/40* (2013.01); *G01N 33/543* (2013.01); *G01N 33/544* (2013.01); *G01N 33/6863* (2013.01); *G01N 2333/525* (2013.01); *A61K 38/00* (2013.01); *C07K 2317/622* (2013.01); *C07K 2319/00* (2013.01); *Y10S 530/811* (2013.01); *Y10S 530/812* (2013.01)
USPC ................. 435/4; 435/7.1; 435/7.8; 530/350; 530/811; 530/812; 436/501

(58) Field of Classification Search
None
See application file for complete search history.

(56) References Cited

U.S. PATENT DOCUMENTS

| | | | |
|---|---|---|---|
| 5,350,836 A * | 9/1994 | Kopchick et al. | 530/399 |
| 6,231,536 B1 * | 5/2001 | Lentz | 604/5.04 |
| 6,379,708 B1 * | 4/2002 | Howell et al. | 424/529 |
| 7,368,295 B2 * | 5/2008 | Tovar et al. | 436/526 |
| 7,662,367 B2 * | 2/2010 | Desjarlais et al. | 424/85.1 |
| 8,197,430 B1 * | 6/2012 | Lentz | 604/6.01 |
| 2003/0185845 A1 * | 10/2003 | Klysner et al. | 424/185.1 |
| 2004/0014948 A1 * | 1/2004 | Halkier et al. | 530/388.22 |

FOREIGN PATENT DOCUMENTS

| | | |
|---|---|---|
| CA | 2524623 | 11/2004 |
| DE | 10144252 A1 | 3/2003 |
| WO | WO 99/61085 | 12/1999 |
| WO | 01/25277 A1 | 4/2001 |
| WO | 0125277 A1 | 4/2001 |
| WO | 01/49866 A1 | 7/2001 |
| WO | 02/00893 A1 | 1/2002 |
| WO | 02/22680 A2 | 3/2002 |
| WO | 02/22680 A3 | 3/2002 |
| WO | 02/077018 A1 | 10/2002 |
| WO | 03/042244 A2 | 5/2003 |
| WO | 03/042244 A3 | 5/2003 |
| WO | 2004/099244 A2 | 11/2004 |
| WO | 2004/099244 A3 | 11/2004 |

OTHER PUBLICATIONS

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details". Nature Biotech 15: 1222-1223, 1997.*

(Continued)

*Primary Examiner* — Bridget E Bunner
(74) *Attorney, Agent, or Firm* — Pillsbury Winthrop Shaw Pittman LLP

(57) ABSTRACT

The invention relates to polypeptides comprising, as constituent A, at least three monomers of a member of the TNF ligand family and, as constituent B, at least two peptide linkers that link the monomers of the member of the TNF ligand family to one another. The invention also relates to the use of these polypeptides for treating diseases and for producing a medicament or a vaccine. The invention also relates to methods for producing and isolating these polypeptides, to nucleic acids that code for these polypeptides, to vectors containing these nucleic acids, to host cells transfected with these vectors, and to pharmaceutical compositions containing these inventive objects. Finally, the invention relates to methods for the extracorporeal manipulation, depletion and/or removal of components contained in body fluids, e.g. by means of apheresis.

23 Claims, 41 Drawing Sheets

(56) References Cited

OTHER PUBLICATIONS

Brenner, S.E. Errors in genome function. Trends in Genetics 15(4): 132-133, 1999.*

Bork et al. Go hunting in sequence databases but watch out for the traps. Trends in Genetics. 12(10): 425-427, 1996.*

Wells. J.A. Additivity of mutational effects in proteins. Biochemistry 29 (37): 8509-8517, 1990.*

Ngo et al. Computational complexity, protein structure prediction, and the Levinthal paradox. The Protein Folding Problem and Tertiary Structure Prediction, pp. 492-495, 1994.*

Krippner-Heidenreich et al. Single-chain TNF, a TNF derivative with enhanced stability and antitumoral activity. J Immunol 180: 8176-8183, 2008.*

Idriss et al. TNFalpha and the TNF receptor superfamily: structure-function relationship(s). Microsc Res Tech 50: 184-195, 2000.*

Lentz et al. Low Molecular weight protein apheresis and regression of breast cancer. Jpn J Apheresis 16(1): 107-14, 1997.*

Lentz et al. The role of therapeutic apheresis in the treatment of cancer: a review. Therapeutic Apheresis 3(1): 40-49, 1999.*

Canadian Application No. 2,563,754, Office Action dated Feb. 20, 2012.

Canadian Application No. 2,563,754, Office Action dated Feb. 1, 2013.

Loetscher, H., et al., Human Tumor Necrosis Factor a (TNFα) Mutants with Exclusive Specificity for the 55-kDa or 75-kDa TNF Receptors, The Journal of Biological Chemistry, 1993, 268(35):26350-26357.

Van Ostade, X., et al., Structure-Activity Studies of Human Tumour Necrosis Factors, Protein Engineering, 1994, 7 (1):5-22.

* cited by examiner

IkB degradation assay

JNK assay

Electrophoretic Mobility Shift Assay (EMSA)

Key: Leitpeptidsequenz = leader peptide sequence
Modul = module

Nucleic acid sequence and corresponding amino acid sequence of scTNF-L$_{short}$ Construct A-II

```
1     ATG AGA GGA TCG CAT CAC CAT CAC CAT CAC GGA TCA GCG TCG TCT    45
1      M   R   G   S   H   H   H   H   H   H   G   S   A   S   S    15

46    TCT TCT CGT ACC CCG TCT GAC AAA CCG GTT GCT CAC GTT GTT GCA    90
16     S   S   R   T   P   S   D   K   P   V   A   H   V   V   A    30

91    AAC CCG CAG GCT GAA GGT CAA CTG CAA TGG CTG AAC CGT CGT GCT    135
31     N   P   Q   A   E   G   Q   L   Q   W   L   N   R   R   A    45

136   AAC GCT CTG CTG GCT AAC GGT GTT GAA CTG CGT GAC AAC CAG CTG    180
46     N   A   L   L   A   N   G   V   E   L   R   D   N   Q   L    60

181   GTT GTT CCG TCT GAA GGC CTG TAC CTG ATC TAC TCC CAG GTT CTG    225
61     V   V   P   S   E   G   L   Y   L   I   Y   S   Q   V   L    75

226   TTC AAA GGC CAG GGC TGC CCG TCC ACC CAC GTT CTG CTG ACC CAC    270
76     F   K   G   Q   G   C   P   S   T   H   V   L   L   T   H    90

271   ACC ATC TCT CGT ATC GCT GTT TCC TAC CAG ACC AAA GTA AAC CTG    315
91     T   I   S   R   I   A   V   S   Y   Q   T   K   V   N   L    105

316   CTG TCT GCA ATC AAA TCT CCG TGC CAG CGT GAA ACC CCG GAA GGT    360
106    L   S   A   I   K   S   P   C   Q   R   E   T   P   E   G    120

361   GCT GAA GCT AAA CCG TGG TAC GAA CCG ATC TAC CTG GGT GGC GTT    405
121    A   E   A   K   P   W   Y   E   P   I   Y   L   G   G   V    135

406   TTT CAA CTG GAG AAA GGT GAC CGT CTG TCT GCA GAA ATT AAC CGT    450
136    F   Q   L   E   K   G   D   R   L   S   A   E   I   N   R    150

451   CCG GAC TAC CTG GAC TTC GCA GAA TCT GGT CAG GTT TAC TTC GGT    495
151    P   D   Y   L   D   F   A   E   S   G   Q   V   Y   F   G    165

496   ATC ATC GCT CTG GGT GGC GGT TCT GGT GGC GGT TCT GGT GGC GGA    540
166    I   I   A   L   G   G   G   S   G   G   G   S   G   G   G    180

541   TCC TCT TCT CGT ACC CCG TCT GAC AAA CCG GTT GCT CAC GTT GTT    585
181    S   S   S   R   T   P   S   D   K   P   V   A   H   V   V    195

586   GCA AAC CCG CAG GCT GAA GGT CAA CTG CAA TGG CTG AAC CGT CGT    630
196    A   N   P   Q   A   E   G   Q   L   Q   W   L   N   R   R    210

631   GCT AAC GCT CTG CTG GCT AAC GGT GTT GAA CTG CGT GAC AAC CAG    675
211    A   N   A   L   L   A   N   G   V   E   L   R   D   N   Q    225

676   CTG GTT GTT CCG TCT GAA GGC CTG TAC CTG ATC TAC TCC CAG GTT    720
226    L   V   V   P   S   E   G   L   Y   L   I   Y   S   Q   V    240

721   CTG TTC AAA GGC CAG GGC TGC CCG TCC ACC CAC GTT CTG CTG ACC    765
241    L   F   K   G   Q   G   C   P   S   T   H   V   L   L   T    255

766   CAC ACC ATC TCT CGT ATC GCT GTT TCC TAC CAG ACC AAA GTA AAC    810
256    H   T   I   S   R   I   A   V   S   Y   Q   T   K   V   N    270

811   CTG CTG TCT GCA ATC AAA TCT CCG TGC CAG CGT GAA ACC CCG GAA    855
271    L   L   S   A   I   K   S   P   C   Q   R   E   T   P   E    285
```

Figure 19A

```
856   GGT GCT GAA GCT AAA CCG TGG TAC GAA CCG ATC TAC CTG GGT GGC   900
286    G   A   E   A   K   P   W   Y   E   P   I   Y   L   G   G   300

901   GTT TTT CAA CTG GAG AAA GGT GAC CGT CTG TCT GCA GAA ATT AAC   945
301    V   F   Q   L   E   K   G   D   R   L   S   A   E   I   N   315

946   CGT CCG GAC TAC CTG GAC TTC GCA GAA TCT GGT CAG GTT TAC TTC   990
316    R   P   D   Y   L   D   F   A   E   S   G   Q   V   Y   F   330

991   GGT ATC ATC GCT CTG GGT GGC GGT TCT GGT GGC GGT TCT GGT GGC   1035
331    G   I   I   A   L   G   G   G   S   G   G   G   S   G   G   345

1036  GGA TCC TCT TCT CGT ACC CCG TCT GAC AAA CCG GTT GCT CAC GTT   1080
346    G   S   S   S   R   T   P   S   D   K   P   V   A   H   V   360

1081  GTT GCA AAC CCG CAG GCT GAA GGT CAA CTG CAA TGG CTG AAC CGT   1125
361    V   A   N   P   Q   A   E   G   Q   L   Q   W   L   N   R   375

1126  CGT GCT AAC GCT CTG CTG GCT AAC GGT GTT GAA CTG CGT GAC AAC   1170
376    R   A   N   A   L   L   A   N   G   V   E   L   R   D   N   390

1171  CAG CTG GTT GTT CCG TCT GAA GGC CTG TAC CTG ATC TAC TCC CAG   1215
391    Q   L   V   V   P   S   E   G   L   Y   L   I   Y   S   Q   405

1216  GTT CTG TTC AAA GGC CAG GGC TGC CCG TCC ACC CAC GTT CTG CTG   1260
406    V   L   F   K   G   Q   G   C   P   S   T   H   V   L   L   420

1261  ACC CAC ACC ATC TCT CGT ATC GCT GTT TCC TAC CAG ACC AAA GTA   1305
421    T   H   T   I   S   R   I   A   V   S   Y   Q   T   K   V   435

1306  AAC CTG CTG TCT GCA ATC AAA TCT CCG TGC CAG CGT GAA ACC CCG   1350
436    N   L   L   S   A   I   K   S   P   C   Q   R   E   T   P   450

1351  GAA GGT GCT GAA GCT AAA CCG TGG TAC GAA CCG ATC TAC CTG GGT   1395
451    E   G   A   E   A   K   P   W   Y   E   P   I   Y   L   G   465

1396  GGC GTT TTT CAA CTG GAG AAA GGT GAC CGT CTG TCT GCA GAA ATT   1440
466    G   V   F   Q   L   E   K   G   D   R   L   S   A   E   I   480

1441  AAC CGT CCG GAC TAC CTG GAC TTC GCA GAA TCT GGT CAG GTT TAC   1485
481    N   R   P   D   Y   L   D   F   A   E   S   G   Q   V   Y   495

1486  TTC GGT ATC ATC GCT CTG TGA                                   1506
496    F   G   I   I   A   L   *                                   501
```

Figure 19B

Nucleic acid sequence and corresponding amino acid sequence of cys-scTNF-L$_{short}$ Construct B-II

```
  1    ATG GGA GAG CTC ATC GAA GGT CGC TGC GCC GGT GGA TCT GGT CAT   45
  1     M   G   E   L   I   E   G   R   C   A   G   G   S   G   H   15

46    CAT CAT CAC CAT CAC GGC TCA GAC GGA GCG TCG TCT TCT TCT CGT   90
 16     H   H   H   H   H   G   S   D   G   A   S   S   S   S   R   30

91    ACC CCG TCT GAC AAA CCG GTT GCT CAC GTT GTT GCA AAC CCG CAG  135
 31     T   P   S   D   K   P   V   A   H   V   V   A   N   P   Q   45

136    GCT GAA GGT CAA CTG CAA TGG CTG AAC CGT CGT GCT AAC GCT CTG  180
 46     A   E   G   Q   L   Q   W   L   N   R   R   A   N   A   L   60

181    CTG GCT AAC GGT GTT GAA CTG CGT GAC AAC CAG CTG GTT GTT CCG  225
 61     L   A   N   G   V   E   L   R   D   N   Q   L   V   V   P   75

226    TCT GAA GGC CTG TAC CTG ATC TAC TCC CAG GTT CTG TTC AAA GGC  270
 76     S   E   G   L   Y   L   I   Y   S   Q   V   L   F   K   G   90

271    CAG GGC TGC CCG TCC ACC CAC GTT CTG CTG ACC CAC ACC ATC TCT  315
 91     Q   G   C   P   S   T   H   V   L   L   T   H   T   I   S  105

316    CGT ATC GCT GTT TCC TAC CAG ACC AAA GTA AAC CTG CTG TCT GCA  360
106     R   I   A   V   S   Y   Q   T   K   V   N   L   L   S   A  120

361    ATC AAA TCT CCG TGC CAG CGT GAA ACC CCG GAA GGT GCT GAA GCT  405
121     I   K   S   P   C   Q   R   E   T   P   E   G   A   E   A  135

406    AAA CCG TGG TAC GAA CCG ATC TAC CTG GGT GGC GTT TTT CAA CTG  450
136     K   P   W   Y   E   P   I   Y   L   G   G   V   F   Q   L  150

451    GAG AAA GGT GAC CGT CTG TCT GCA GAA ATT AAC CGT CCG GAC TAC  495
151     E   K   G   D   R   L   S   A   E   I   N   R   P   D   Y  165

496    CTG GAC TTC GCA GAA TCT GGT CaG GTT TAC TTC GGT ATC ATC GCT  540
166     L   D   F   A   E   S   G   Q   V   Y   F   G   I   I   A  180

541    CTG GGT GGC GGT TCT GGT GGC GGT TCT GGT GGC GGA TCC TCT TCT  585
181     L   G   G   G   S   G   G   G   S   G   G   G   S   S   S  195

586    CGT ACC CCG TCT GAC AAA CCG GTT GCT CAC GTT GTT GCA AAC CCG  630
196     R   T   P   S   D   K   P   V   A   H   V   V   A   N   P  210

631    CAG GCT GAA GGT CAA CTG CAA TGG CTG AAC CGT CGT GCT AAC GCT  675
211     Q   A   E   G   Q   L   Q   W   L   N   R   R   A   N   A  225

676    CTG CTG GCT AAC GGT GTT GAA CTG CGT GAC AAC CAG CTG GTT GTT  720
226     L   L   A   N   G   V   E   L   R   D   N   Q   L   V   V  240

721    CCG TCT GAA GGC CTG TAC CTG ATC TAC TCC CAG GTT CTG TTC AAA  765
241     P   S   E   G   L   Y   L   I   Y   S   Q   V   L   F   K  255

766    GGC CAG GGC TGC CCG TCC ACC CAC GTT CTG CTG ACC CAC ACC ATC  810
256     G   Q   G   C   P   S   T   H   V   L   L   T   H   T   I  270
```

Figure 20A

```
811  TCT CGT ATC GCT GTT TCC TAC CAG ACC AAA GTA AAC CTG CTG TCT  855
271   S   R   I   A   V   S   Y   Q   T   K   V   N   L   L   S   285

856  GCA ATC AAA TCT CCG TGC CAG CGT GAA ACC CCG GAA GGT GCT GAA  900
286   A   I   K   S   P   C   Q   R   E   T   P   E   G   A   E   300

901  GCT AAA CCG TGG TAC GAA CCG ATC TAC CTG GGT GGC GTT TTT CAA  945
301   A   K   P   W   Y   E   P   I   Y   L   G   G   V   F   Q   315

946  CTG GAG AAA GGT GAC CGT CTG TCT GCA GAA ATT AAC CGT CCG GAC  990
316   L   E   K   G   D   R   L   S   A   E   I   N   R   P   D   330

991  TAC CTG GAC TTC GCA GAA TCT GGT CAG GTT TAC TTC GGT ATC ATC  1035
331   Y   L   D   F   A   E   S   G   Q   V   Y   F   G   I   I   345

1036 GCT CTG GGT GGC GGT TCT GGT GGC GGT TCT GGT GGC GGA TCC TCT  1080
346   A   L   G   G   G   S   G   G   G   S   G   G   G   S   S   360

1081 TCT CGT ACC CCG TCT GAC AAA CCG GTT GCT CAC GTT GTT GCA AAC  1125
361   S   R   T   P   S   D   K   P   V   A   H   V   V   A   N   375

1126 CCG CAG GCT GAA GGT CAA CTG CAA TGG CTG AAC CGT CGT GCT AAC  1170
376   P   Q   A   E   G   Q   L   Q   W   L   N   R   R   A   N   390

1171 GCT CTG CTG GCT AAC GGT GTT GAA CTG CGT GAC AAC CAG CTG GTT  1215
391   A   L   L   A   N   G   V   E   L   R   D   N   Q   L   V   405

1216 GTT CCG TCT GAA GGC CTG TAC CTG ATC TAC TCC CAG GTT CTG TTC  1260
406   V   P   S   E   G   L   Y   L   I   Y   S   Q   V   L   F   420

1261 AAA GGC CAG GGC TGC CCG TCC ACC CAC GTT CTG CTG ACC CAC ACC  1305
421   K   G   Q   G   C   P   S   T   H   V   L   L   T   H   T   435

1306 ATC TCT CGT ATC GCT GTT TCC TAC CAG ACC AAA GTA AAC CTG CTG  1350
436   I   S   R   I   A   V   S   Y   Q   T   K   V   N   L   L   450

1351 TCT GCA ATC AAA TCT CCG TGC CAG CGT GAA ACC CCG GAA GGT GCT  1395
451   S   A   I   K   S   P   C   Q   R   E   T   P   E   G   A   465

1396 GAA GCT AAA CCG TGG TAC GAA CCG ATC TAC CTG GGT GGC GTT TTT  1440
466   E   A   K   P   W   Y   E   P   I   Y   L   G   G   V   F   480

1441 CAA CTG GAG AAA GGT GAC CGT CTG TCT GCA GAA ATT AAC CGT CCG  1485
481   Q   L   E   K   G   D   R   L   S   A   E   I   N   R   P   495

1486 GAC TAC CTG GAC TTC GCA GAA TCT GGT CAG GTT TAC TTC GGT ATC  1530
496   D   Y   L   D   F   A   E   S   G   Q   V   Y   F   G   I   510

1531 ATC GCT CTG TGA                                                1542
511   I   A   L   *                                                 513
```

Figure 20B

Nucleic acid sequence and corresponding amino acid sequence of scFasL Construct C

```
1     ATG GCT ATC ATC TAC CTC ATC CTC CTG TTC ACC GCT GTG CGG GGC   45
1      M   A   I   I   Y   L   I   L   L   F   T   A   V   R   G    15

46    GCG GCC GCG GAT TAC AAA GAC GAT GAC GAT AAA GAA TTC ACG CGT   90
16     A   A   A   D   Y   K   D   D   D   D   K   E   F   T   R    30

91    GAA AAA AAG GAG CTG AGG AAA GTG GCC CAT TTA ACA GGC AAG TCC  135
31     E   K   K   E   L   R   K   V   A   H   L   T   G   K   S    45

136   AAC TCA AGG TCC ATG CCT CTG GAA TGG GAA GAC ACC TAT GGA ATT  180
46     N   S   R   S   M   P   L   E   W   E   D   T   Y   G   I    60

181   GTC CTG CTT TCT GGA GTG AAG TAT AAG AAG GGT GGC CTT GTG ATC  225
61     V   L   L   S   G   V   K   Y   K   K   G   G   L   V   I    75

226   AAT GAA ACT GGG CTG TAC TTT GTA TAT TCC AAA GTA TAC TTC CGG  270
76     N   E   T   G   L   Y   F   V   Y   S   K   V   Y   F   R    90

271   GGT CAA TCT TGC AAC AAC CTG CCC CTG AGC CAC AAG GTC TAC ATG  315
91     G   Q   S   C   N   N   L   P   L   S   H   K   V   Y   M   105

316   AGG AAC TCT AAG TAT CCC CAG GAT CTG GTG ATG ATG GAG GGG AAG  360
106    R   N   S   K   Y   P   Q   D   L   V   M   M   E   G   K   120

361   ATG ATG AGC TAC TGC ACT ACT GGG CAG ATG TGG GCC CGC AGC AGC  405
121    M   M   S   Y   C   T   T   G   Q   M   W   A   R   S   S   135

406   TAC CTG GGG GCA GTG TTC AAT CTT ACC AGT GCT GAT CAT TTA TAT  450
136    Y   L   G   A   V   F   N   L   T   S   A   D   H   L   Y   150

451   GTC AAC GTA TCT GAG CTC TCT CTG GTC AAT TTT GAG GAA TCT CAG  495
151    V   N   V   S   E   L   S   L   V   N   F   E   E   S   Q   165

496   ACG TTT TTC GGC TTA TAT AAG CTC GGT GGC GGT TCT GGT GGC GGT  540
166    T   F   F   G   L   Y   K   L   G   G   G   S   G   G   G   180

541   TCT GGT GGC GGT TCT GGT GGC GGA TCA GAA AAA AAG GAG CTG AGG  585
181    S   G   G   G   S   G   G   G   S   E   K   K   E   L   R   195

586   AAA GTG GCC CAT TTA ACA GGC AAG TCC AAC TCA AGG TCC ATG CCT  630
196    K   V   A   H   L   T   G   K   S   N   S   R   S   M   P   210

631   CTG GAA TGG GAA GAC ACC TAT GGA ATT GTC CTG CTT TCT GGA GTG  675
211    L   E   W   E   D   T   Y   G   I   V   L   L   S   G   V   225

676   AAG TAT AAG AAG GGT GGC CTT GTG ATC AAT GAA ACT GGG CTG TAC  720
226    K   Y   K   K   G   G   L   V   I   N   E   T   G   L   Y   240

721   TTT GTA TAT TCC AAA GTA TAC TTC CGG GGT CAA TCT TGC AAC AAC  765
241    F   V   Y   S   K   V   Y   F   R   G   Q   S   C   N   N   255
```

Figure 21A

```
766   CTG CCC CTG AGC CAC AAG GTC TAC ATG AGG AAC TCT AAG TAT CCC   810
256    L   P   L   S   H   K   V   Y   M   R   N   S   K   Y   P   270

811   CAG GAT CTG GTG ATG ATG GAG GGG AAG ATG ATG AGC TAC TGC ACT   855
271    Q   D   L   V   M   M   E   G   K   M   M   S   Y   C   T   285

856   ACT GGG CAG ATG TGG GCC CGC AGC AGC TAC CTG GGG GCA GTG TTC   900
286    T   G   Q   M   W   A   R   S   S   Y   L   G   A   V   F   300

901   AAT CTT ACC AGT GCT GAT CAT TTA TAT GTC AAC GTA TCT GAG CTC   945
301    N   L   T   S   A   D   H   L   Y   V   N   V   S   E   L   315

946   TCT CTG GTC AAT TTT GAG GAA TCT CAG ACG TTT TTC GGC TTA TAT   990
316    S   L   V   N   F   E   E   S   Q   T   F   F   G   L   Y   330

991   AAG CTC GGT GGC GGT TCT GGT GGC GGT TCT GGT GGC GGT TCT GGT   1035
331    K   L   G   G   G   S   G   G   G   S   G   G   G   S   G   345

1036  GGC GGA TCC GAA AAA AAG GAG CTG AGG AAA GTG GCC CAT TTA ACA   1080
346    G   G   S   E   K   K   E   L   R   K   V   A   H   L   T   360

1081  GGC AAG TCC AAC TCA AGG TCC ATG CCT CTG GAA TGG GAA GAC ACC   1125
361    G   K   S   N   S   R   S   M   P   L   E   W   E   D   T   375

1126  TAT GGA ATT GTC CTG CTT TCT GGA GTG AAG TAT AAG AAG GGT GGC   1170
376    Y   G   I   V   L   L   S   G   V   K   Y   K   K   G   G   390

1171  CTT GTG ATC AAT GAA ACT GGG CTG TAC TTT GTA TAT TCC AAA GTA   1215
391    L   V   I   N   E   T   G   L   Y   F   V   Y   S   K   V   405

1216  TAC TTC CGG GGT CAA TCT TGC AAC AAC CTG CCC CTG AGC CAC AAG   1260
406    Y   F   R   G   Q   S   C   N   N   L   P   L   S   H   K   420

1261  GTC TAC ATG AGG AAC TCT AAG TAT CCC CAG GAT CTG GTG ATG ATG   1305
421    V   Y   M   R   N   S   K   Y   P   Q   D   L   V   M   M   435

1306  GAG GGG AAG ATG ATG AGC TAC TGC ACT ACT GGG CAG ATG TGG GCC   1350
436    E   G   K   M   M   S   Y   C   T   T   G   Q   M   W   A   450

1351  CGC AGC AGC TAC CTG GGG GCA GTG TTC AAT CTT ACC AGT GCT GAT   1395
451    R   S   S   Y   L   G   A   V   F   N   L   T   S   A   D   465

1396  CAT TTA TAT GTC AAC GTA TCT GAG CTC TCT CTG GTC AAT TTT GAG   1440
466    H   L   Y   V   N   V   S   E   L   S   L   V   N   F   E   480

1441  GAA TCT CAG ACG TTT TTC GGC TTA TAT AAG CTC TGA               1476
481    E   S   Q   T   F   F   G   L   Y   K   L   *               491
```

Figure 21B

Nucleic acid sequence and corresponding amino acid sequence of scTRAIL Construct D

```
  1    ATG GCT ATC ATC TAC CTC ATC CTC CTG TTC ACC GCT GTG CGG GGC   45
  1     M   A   I   I   Y   L   I   L   L   F   T   A   V   R   G    15

46    GCG GCC GCG GAT TAC AAA GAC GAT GAC GAT AAA GAA TTC GGA ACC   90
 16     A   A   A   D   Y   K   D   D   D   D   K   E   F   G   T    30

91    TCT GAG GAA ACC ATT TCT ACA GTT CAA GAA AAG CAA CAA AAT ATT   135
 31     S   E   E   T   I   S   T   V   Q   E   K   Q   Q   N   I    45

136    TCT CCC CTA GTG AGA GAA AGA GGT CCT CAG AGA GTA GCA GCT CAC   180
 46     S   P   L   V   R   E   R   G   P   Q   R   V   A   A   H    60

181    ATA ACT GGG ACC AGA GGA AGA AGC AAC ACA TTG TCT TCT CCA AAC   225
 61     I   T   G   T   R   G   R   S   N   T   L   S   S   P   N    75

226    TCC AAG AAT GAA AAG GCT CTG GGC CGC AAA ATA AAC TCC TGG GAA   270
 76     S   K   N   E   K   A   L   G   R   K   I   N   S   W   E    90

271    TCA TCA AGG AGT GGG CAT TCA TTC CTG AGC AAC TTG CAC TTG AGG   315
 91     S   S   R   S   G   H   S   F   L   S   N   L   H   L   R   105

316    AAT GGT GAA CTG GTC ATC CAT GAA AAA GGG TTT TAC TAC ATC TAT   360
106     N   G   E   L   V   I   H   E   K   G   F   Y   Y   I   Y   120

361    TCC CAA ACA TAC TTT CGA TTT CAG GAG GAA ATA AAA GAA AAC ACA   405
121     S   Q   T   Y   F   R   F   Q   E   E   I   K   E   N   T   135

406    AAG AAC GAC AAA CAA ATG GTC CAA TAT ATT TAC AAA TAC ACA AGT   450
136     K   N   D   K   Q   M   V   Q   Y   I   Y   K   Y   T   S   150

451    TAT CCT GAC CCT ATA TTG TTG ATG AAA AGT GCT AGA AAT AGT TGT   495
151     Y   P   D   P   I   L   L   M   K   S   A   R   N   S   C   165

496    TGG TCT AAA GAT GCA GAA TAT GGA CTC TAT TCC ATC TAT CAA GGG   540
166     W   S   K   D   A   E   Y   G   L   Y   S   I   Y   Q   G   180

541    GGA ATA TTT GAG CTT AAG GAA AAT GAC AGA ATT TTT GTT TCT GTA   585
181     G   I   F   E   L   K   E   N   D   R   I   F   V   S   V   195

586    ACA AAT GAG CAC TTG ATA GAC ATG GAC CAT GAA GCC AGT TTT TTC   630
196     T   N   E   H   L   I   D   M   D   H   E   A   S   F   F   210

631    GGG GCC TTT TTA GTT GGC GGT GGC GGT TCT GGT GGC GGT TCT GGT   675
211     G   A   F   L   V   G   G   G   G   S   G   G   G   S   G   225

676    GGC GGT TCT GGT GGC GGA TCA ACC TCT GAG GAA ACC ATT TCT ACA   720
226     G   G   S   G   G   G   S   T   S   E   E   T   I   S   T   240

721    GTT CAA GAA AAG CAA CAA AAT ATT TCT CCC CTA GTG AGA GAA AGA   765
241     V   Q   E   K   Q   Q   N   I   S   P   L   V   R   E   R   255
```

Figure 22A

```
766   GGT CCT CAG AGA GTA GCA GCT CAC ATA ACT GGG ACC AGA GGA AGA   810
256    G   P   Q   R   V   A   A   H   I   T   G   T   R   G   R    270

811   AGC AAC ACA TTG TCT TCT CCA AAC TCC AAG AAT GAA AAG GCT CTG   855
271    S   N   T   L   S   S   P   N   S   K   N   E   K   A   L    285

856   GGC CGC AAA ATA AAC TCC TGG GAA TCA TCA AGG AGT GGG CAT TCA   900
286    G   R   K   I   N   S   W   E   S   S   R   S   G   H   S    300

901   TTC CTG AGC AAC TTG CAC TTG AGG AAT GGT GAA CTG GTC ATC CAT   945
301    F   L   S   N   L   H   L   R   N   G   E   L   V   I   H    315

946   GAA AAA GGG TTT TAC TAC ATC TAT TCC CAA ACA TAC TTT CGA TTT   990
316    E   K   G   F   Y   Y   I   Y   S   Q   T   Y   F   R   F    330

991   CAG GAG GAA ATA AAA GAA AAC ACA AAG AAC GAC AAA CAA ATG GTC   1035
331    Q   E   E   I   K   E   N   T   K   N   D   K   Q   M   V    345

1036  CAA TAT ATT TAC AAA TAC ACA AGT TAT CCT GAC CCT ATA TTG TTG   1080
346    Q   Y   I   Y   K   Y   T   S   Y   P   D   P   I   L   L    360

1081  ATG AAA AGT GCT AGA AAT AGT TGT TGG TCT AAA GAT GCA GAA TAT   1125
361    M   K   S   A   R   N   S   C   W   S   K   D   A   E   Y    375

1126  GGA CTC TAT TCC ATC TAT CAA GGG GGA ATA TTT GAG CTT AAG GAA   1170
376    G   L   Y   S   I   Y   Q   G   G   I   F   E   L   K   E    390

1171  AAT GAC AGA ATT TTT GTT TCT GTA ACA AAT GAG CAC TTG ATA GAC   1215
391    N   D   R   I   F   V   S   V   T   N   E   H   L   I   D    405

1216  ATG GAC CAT GAA GCC AGT TTT TTC GGG GCC TTT TTA GTT GGC GGT   1260
406    M   D   H   E   A   S   F   F   G   A   F   L   V   G   G    420

1261  GGC GGT TCT GGT GGC GGT TCT GGT GGC GGT TCT GGT GGC GGA TCC   1305
421    G   G   S   G   G   G   S   G   G   G   S   G   G   G   S    435

1306  ACC TCT GAG GAA ACC ATT TCT ACA GTT CAA GAA AAG CAA CAA AAT   1350
436    T   S   E   E   T   I   S   T   V   Q   E   K   Q   Q   N    450

1351  ATT TCT CCC CTA GTG AGA GAA AGA GGT CCT CAG AGA GTA GCA GCT   1395
451    I   S   P   L   V   R   E   R   G   P   Q   R   V   A   A    465

1396  CAC ATA ACT GGG ACC AGA GGA AGA AGC AAC ACA TTG TCT TCT CCA   1440
466    H   I   T   G   T   R   G   R   S   N   T   L   S   S   P    480

1441  AAC TCC AAG AAT GAA AAG GCT CTG GGC CGC AAA ATA AAC TCC TGG   1485
481    N   S   K   N   E   K   A   L   G   R   K   I   N   S   W    495

1486  GAA TCA TCA AGG AGT GGG CAT TCA TTC CTG AGC AAC TTG CAC TTG   1530
496    E   S   S   R   S   G   H   S   F   L   S   N   L   H   L    510

1531  AGG AAT GGT GAA CTG GTC ATC CAT GAA AAA GGG TTT TAC TAC ATC   1575
511    R   N   G   E   L   V   I   H   E   K   G   F   Y   Y   I    525

1576  TAT TCC CAA ACA TAC TTT CGA TTT CAG GAG GAA ATA AAA GAA AAC   1620
526    Y   S   Q   T   Y   F   R   F   Q   E   E   I   K   E   N    540
```

Figure 22B

```
1621  ACA AAG AAC GAC AAA CAA ATG GTC CAA TAT ATT TAC AAA TAC ACA  1665
541    T   K   N   D   K   Q   M   V   Q   Y   I   Y   K   Y   T   555

1666  AGT TAT CCT GAC CCT ATA TTG TTG ATG AAA AGT GCT AGA AAT AGT  1710
556    S   Y   P   D   P   I   L   L   M   K   S   A   R   N   S   570

1711  TGT TGG TCT AAA GAT GCA GAA TAT GGA CTC TAT TCC ATC TAT CAA  1755
571    C   W   S   K   D   A   E   Y   G   L   Y   S   I   Y   Q   585

1756  GGG GGA ATA TTT GAG CTT AAG GAA AAT GAC AGA ATT TTT GTT TCT  1800
586    G   G   I   F   E   L   K   E   N   D   R   I   F   V   S   600

1801  GTA ACA AAT GAG CAC TTG ATA GAC ATG GAC CAT GAA GCC AGT TTT  1845
601    V   T   N   E   H   L   I   D   M   D   H   E   A   S   F   615

1846  TTC GGG GCC TTT TTA GTT GGC TGA                              1866
616    F   G   A   F   L   V   G   *                               622
```

Figure 22C

Nucleic acid sequence and corresponding amino acid sequence of scTNF
Construct E

```
1    ATG GCT ATC ATC TAC CTC ATC CTC CTG TTC ACC GCT GTG CGG GGC    45
1     M   A   I   I   Y   L   I   L   L   F   T   A   V   R   G    15

46   GCG GCC GCG GAT TAC AAA GAC GAT GAC GAT AAA GAA TTC GGA TCA    90
16    A   A   A   D   Y   K   D   D   D   D   K   E   F   G   S    30

91   TCT TCT CGA ACC CCG AGT GAC AAG CCT GTA GCC CAT GTT GTA GCA   135
31    S   S   R   T   P   S   D   K   P   V   A   H   V   V   A    45

136  AAC CCT CAA GCT GAG GGG CAG CTC CAG TGG CTG AAC CGC CGG GCC   180
46    N   P   Q   A   E   G   Q   L   Q   W   L   N   R   R   A    60

181  AAT GCC CTC CTG GCC AAT GGC GTG GAG CTG AGA GAT AAC CAG CTG   225
61    N   A   L   L   A   N   G   V   E   L   R   D   N   Q   L    75

226  GTG GTG CCA TCA GAG GGC CTG TAC CTC ATC TAC TCC CAG GTC CTC   270
76    V   V   P   S   E   G   L   Y   L   I   Y   S   Q   V   L    90

271  TTC AAG GGC CAA GGC TGC CCC TCC ACC CAT GTG CTC CTC ACC CAC   315
91    F   K   G   Q   G   C   P   S   T   H   V   L   L   T   H   105

316  ACC ATC AGC CGC ATC GCC GTC TCC TAC CAG ACC AAG GTC AAC CTC   360
106   T   I   S   R   I   A   V   S   Y   Q   T   K   V   N   L   120

361  CTC TCT GCC ATC AAG AGC CCC TGC CAG AGG GAG ACC CCA GAG GGG   405
121   L   S   A   I   K   S   P   C   Q   R   E   T   P   E   G   135

406  GCT GAG GCC AAG CCC TGG TAT GAG CCC ATC TAT CTG GGA GGG GTC   450
136   A   E   A   K   P   W   Y   E   P   I   Y   L   G   G   V   150

451  TTC CAG CTG GAG AAG GGT GAC CGA CTC AGC GCT GAG ATC AAT CGG   495
151   F   Q   L   E   K   G   D   R   L   S   A   E   I   N   R   165

496  CCC GAC TAT CTC GAC TTT GCC GAG TCT GGG CAG GTC TAC TTT GGG   540
166   P   D   Y   L   D   F   A   E   S   G   Q   V   Y   F   G   180

541  ATC ATT GCC CTG GGT GGC GGT TCT GGT GGC GGT TCT GGT GGC GGT   585
181   I   I   A   L   G   G   G   S   G   G   G   S   G   G   G   195

586  TCT GGT GGC GGA TCA TCA TCT TCT CGA ACC CCG AGT GAC AAG CCT   630
196   S   G   G   G   S   S   S   S   R   T   P   S   D   K   P   210

631  GTA GCC CAT GTT GTA GCA AAC CCT CAA GCT GAG GGG CAG CTC CAG   675
211   V   A   H   V   V   A   N   P   Q   A   E   G   Q   L   Q   225

676  TGG CTG AAC CGC CGG GCC AAT GCC CTC CTG GCC AAT GGC GTG GAG   720
226   W   L   N   R   R   A   N   A   L   L   A   N   G   V   E   240

721  CTG AGA GAT AAC CAG CTG GTG GTG CCA TCA GAG GGC CTG TAC CTC   765
241   L   R   D   N   Q   L   V   V   P   S   E   G   L   Y   L   255
```

Figure 23A

```
766  ATC TAC TCC CAG GTC CTC TTC AAG GGC CAA GGC TGC CCC TCC ACC  810
256   I   Y   S   Q   V   L   F   K   G   Q   G   C   P   S   T  270

811  CAT GTG CTC CTC ACC CAC ACC ATC AGC CGC ATC GCC GTC TCC TAC  855
271   H   V   L   L   T   H   T   I   S   R   I   A   V   S   Y  285

856  CAG ACC AAG GTC AAC CTC CTC TCT GCC ATC AAG AGC CCC TGC CAG  900
286   Q   T   K   V   N   L   L   S   A   I   K   S   P   C   Q  300

901  AGG GAG ACC CCA GAG GGG GCT GAG GCC AAG CCC TGG TAT GAG CCC  945
301   R   E   T   P   E   G   A   E   A   K   P   W   Y   E   P  315

946  ATC TAT CTG GGA GGG GTC TTC CAG CTG GAG AAG GGT GAC CGA CTC  990
316   I   Y   L   G   G   V   F   Q   L   E   K   G   D   R   L  330

991  AGC GCT GAG ATC AAT CGG CCC GAC TAT CTC GAC TTT GCC GAG TCT  1035
331   S   A   E   I   N   R   P   D   Y   L   D   F   A   E   S  345

1036 GGG CAG GTC TAC TTT GGG ATC ATT GCC CTG GGT GGC GGT TCT GGT  1080
346   G   Q   V   Y   F   G   I   I   A   L   G   G   G   S   G  360

1081 GGC GGT TCT GGT GGC GGT TCT GGT GGC GGA TCA TCA TCT TCT CGA  1125
361   G   G   S   G   G   G   S   G   G   G   S   S   S   S   R  375

1126 ACC CCG AGT GAC AAG CCT GTA GCC CAT GTT GTA GCA AAC CCT CAA  1170
376   T   P   S   D   K   P   V   A   H   V   V   A   N   P   Q  390

1171 GCT GAG GGG CAG CTC CAG TGG CTG AAC CGC CGG GCC AAT GCC CTC  1215
391   A   E   G   Q   L   Q   W   L   N   R   R   A   N   A   L  405

1216 CTG GCC AAT GGC GTG GAG CTG AGA GAT AAC CAG CTG GTG GTG CCA  1260
406   L   A   N   G   V   E   L   R   D   N   Q   L   V   V   P  420

1261 TCA GAG GGC CTG TAC CTC ATC TAC TCC CAG GTC CTC TTC AAG GGC  1305
421   S   E   G   L   Y   L   I   Y   S   Q   V   L   F   K   G  435

1306 CAA GGC TGC CCC TCC ACC CAT GTG CTC CTC ACC CAC ACC ATC AGC  1350
436   Q   G   C   P   S   T   H   V   L   L   T   H   T   I   S  450

1351 CGC ATC GCC GTC TCC TAC CAG ACC AAG GTC AAC CTC CTC TCT GCC  1395
451   R   I   A   V   S   Y   Q   T   K   V   N   L   L   S   A  465

1396 ATC AAG AGC CCC TGC CAG AGG GAG ACC CCA GAG GGG GCT GAG GCC  1440
466   I   K   S   P   C   Q   R   E   T   P   E   G   A   E   A  480

1441 AAG CCC TGG TAT GAG CCC ATC TAT CTG GGA GGG GTC TTC CAG CTG  1485
481   K   P   W   Y   E   P   I   Y   L   G   G   V   F   Q   L  495

1486 GAG AAG GGT GAC CGA CTC AGC GCT GAG ATC AAT CGG CCC GAC TAT  1530
496   E   K   G   D   R   L   S   A   E   I   N   R   P   D   Y  510

1531 CTC GAC TTT GCC GAG TCT GGG CAG GTC TAC TTT GGG ATC ATT GCC  1575
511   L   D   F   A   E   S   G   Q   V   Y   F   G   I   I   A  525

1576 CTG TGA                                                      1581
526   L   *                                                      526
```

Figure 23B

Nucleic acid sequence and corresponding amino acid sequence of scFasL-AMAIZe Construct F

| | | | | | | | | | | | | | | | | |
|---|---|---|---|---|---|---|---|---|---|---|---|---|---|---|---|---|
| 1 | ATG | GAC | TGG | ACC | TGG | CGC | GTG | TTT | TGC | CTG | CTC | GCC | GTG | GCT | CCT | 45 |
| 1 | M | D | W | T | W | R | V | F | C | L | L | A | V | A | P | 15 |
| 46 | GGG | GCC | CAC | AGC | CAG | GTA | CAG | CTG | GTG | CAG | TCT | GGG | GGA | GGC | ATG | 90 |
| 16 | G | A | H | S | Q | V | Q | L | V | Q | S | G | G | G | M | 30 |
| 91 | GTA | GAG | CCT | GGG | GGG | TCC | CTT | AGA | CTC | TCC | TGT | GCA | GCC | TCT | GGA | 135 |
| 31 | V | E | P | G | G | S | L | R | L | S | C | A | A | S | G | 45 |
| 136 | TTC | ACT | TTC | AGT | AAT | GCC | TGG | ATG | AGC | TGG | GTC | CGC | CAG | GCT | CCA | 180 |
| 46 | F | T | F | S | N | A | W | M | S | W | V | R | Q | A | P | 60 |
| 181 | GGG | AAG | GGG | CTG | GAG | TGG | GTT | GGC | CGT | ATA | AAA | AGC | AAA | GCT | GGT | 225 |
| 61 | G | K | G | L | E | W | V | G | R | I | K | S | K | A | G | 75 |
| 226 | GGT | GGG | ACA | GCA | GAG | TAC | GCT | GCA | CCC | GTG | AAA | GGC | AGA | TTC | ACC | 270 |
| 76 | G | G | T | A | E | Y | A | A | P | V | K | G | R | F | T | 90 |
| 271 | ATC | TCA | AGA | GAT | GAT | TCA | CAA | AAC | ACG | CTG | TAT | CTG | CAA | ATG | AAC | 315 |
| 91 | I | S | R | D | D | S | Q | N | T | L | Y | L | Q | M | N | 105 |
| 316 | AGC | CTG | AAA | ACC | GAC | GAC | ACA | GCC | GTG | TAT | TAC | TGT | ACC | ACA | CAT | 360 |
| 106 | S | L | K | T | D | D | T | A | V | Y | Y | C | T | T | H | 120 |
| 361 | GTC | TAC | GGT | GCC | CCC | CGG | AAC | TGG | GGC | CAG | GGA | TCC | CTG | GTC | ACC | 405 |
| 121 | V | Y | G | A | P | R | N | W | G | Q | G | S | L | V | T | 135 |
| 406 | GTC | TCC | TCA | GCC | TCC | ACC | AAG | GGC | CCA | AAG | CTT | GAA | GAA | GGT | GAA | 450 |
| 136 | V | S | S | A | S | T | K | G | P | K | L | E | E | G | E | 150 |
| 451 | TTT | TCA | GAA | GCA | CGC | GTA | CAG | TCT | GTG | TTG | ACT | CAG | CCG | CCC | TCA | 495 |
| 151 | F | S | E | A | R | V | Q | S | V | L | T | Q | P | P | S | 165 |
| 496 | GTG | TCT | GCG | GCC | CCA | GGA | CAG | AAG | GTC | ACC | ATC | TCC | TGC | TCT | GGA | 540 |
| 166 | V | S | A | A | P | G | Q | K | V | T | I | S | C | S | G | 180 |
| 541 | AGC | AGC | TCC | AAC | ATT | GGA | AAT | AAT | TAT | GTC | TCC | TGG | TAC | GTT | CAA | 585 |
| 181 | S | S | S | N | I | G | N | N | Y | V | S | W | Y | V | Q | 195 |
| 586 | CTC | CCA | GGA | ACA | GCC | CCC | AAA | CTC | CTC | ATT | TAT | GAC | AAT | AAT | AAG | 630 |
| 196 | L | P | G | T | A | P | K | L | L | I | Y | D | N | N | K | 210 |
| 631 | CGA | TTC | TCA | GGA | GTT | CCT | GAC | CGA | TTC | TCT | GGC | TCC | AAG | TCT | GGC | 675 |
| 211 | R | F | S | G | V | P | D | R | F | S | G | S | K | S | G | 225 |
| 676 | ACG | TCA | GCC | ACC | CTG | GGC | ATC | ACC | GGG | CTC | CAG | ACT | GGG | GAC | GAG | 720 |
| 226 | T | S | A | T | L | G | I | T | G | L | Q | T | G | D | E | 240 |
| 721 | GCC | GAT | TAT | TAC | TGC | GGA | GCA | TGG | GAT | GGC | AGC | CTG | CGT | GAA | GCG | 765 |
| 241 | A | D | Y | Y | C | G | A | W | D | G | S | L | R | E | A | 255 |

Figure 24A

```
766   GTA TTC GGC GGA GGG ACC AAG GTC ACC GTC CTA GGT GCG GCC GCA   810
256    V   F   G   G   G   T   K   V   T   V   L   G   A   A   A   270

811   GTT GAG CTC GAG gcg GCC GCG GAT TAC AAA GAC GAT GAC GAT AAA   855
271    V   E   L   E   A   A   A   D   Y   K   D   D   D   D   K   285

856   GAA TTC ACG CGT GAA AAA AAG GAG CTG AGG AAA GTG GCC CAT TTA   900
286    E   F   T   R   E   K   K   E   L   R   K   V   A   H   L   300

901   ACA GGC AAG TCC AAC TCA AGG TCC ATG CCT CTG GAA TGG GAA GAC   945
301    T   G   K   S   N   S   R   S   M   P   L   E   W   E   D   315

946   ACC TAT GGA ATT GTC CTG CTT TCT GGA GTG AAG TAT AAG AAG GGT   990
316    T   Y   G   I   V   L   L   S   G   V   K   Y   K   K   G   330

991   GGC CTT GTG ATC AAT GAA ACT GGG CTG TAC TTT GTA TAT TCC AAA   1035
331    G   L   V   I   N   E   T   G   L   Y   F   V   Y   S   K   345

1036  GTA TAC TTC CGG GGT CAA TCT TGC AAC AAC CTG CCC CTG AGC CAC   1080
346    V   Y   F   R   G   Q   S   C   N   N   L   P   L   S   H   360

1081  AAG GTC TAC ATG AGG AAC TCT AAG TAT CCC CAG GAT CTG GTG ATG   1125
361    K   V   Y   M   R   N   S   K   Y   P   Q   D   L   V   M   375

1126  ATG GAG GGG AAG ATG ATG AGC TAC TGC ACT ACT GGG CAG ATG TGG   1170
376    M   E   G   K   M   M   S   Y   C   T   T   G   Q   M   W   390

1171  GCC CGC AGC AGC TAC CTG GGG GCA GTG TTC AAT CTT ACC AGT GCT   1215
391    A   R   S   S   Y   L   G   A   V   F   N   L   T   S   A   405

1216  GAT CAT TTA TAT GTC AAC GTA TCT GAG CTC TCT CTG GTC AAT TTT   1260
406    D   H   L   Y   V   N   V   S   E   L   S   L   V   N   F   420

1261  GAG GAA TCT CAG ACG TTT TTC GGC TTA TAT AAG CTC GGT GGC GGT   1305
421    E   E   S   Q   T   F   F   G   L   Y   K   L   G   G   G   435

1306  TCT GGT GGC GGT TCT GGT GGC GGT TCT GGT GGC GGA TCA GAA AAA   1350
436    S   G   G   G   S   G   G   G   S   G   G   G   S   E   K   450

1351  AAG GAG CTG AGG AAA GTG GCC CAT TTA ACA GGC AAG TCC AAC TCA   1395
451    K   E   L   R   K   V   A   H   L   T   G   K   S   N   S   465

1396  AGG TCC ATG CCT CTG GAA TGG GAA GAC ACC TAT GGA ATT GTC CTG   1440
466    R   S   M   P   L   E   W   E   D   T   Y   G   I   V   L   480

1441  CTT TCT GGA GTG AAG TAT AAG AAG GGT GGC CTT GTG ATC AAT GAA   1485
481    L   S   G   V   K   Y   K   K   G   G   L   V   I   N   E   495

1486  ACT GGG CTG TAC TTT GTA TAT TCC AAA GTA TAC TTC CGG GGT CAA   1530
496    T   G   L   Y   F   V   Y   S   K   V   Y   F   R   G   Q   510

1531  TCT TGC AAC AAC CTG CCC CTG AGC CAC AAG GTC TAC ATG AGG AAC   1575
511    S   C   N   N   L   P   L   S   H   K   V   Y   M   R   N   525

1576  TCT AAG TAT CCC CAG GAT CTG GTG ATG ATG GAG GGG AAG ATG ATG   1620
526    S   K   Y   P   Q   D   L   V   M   M   E   G   K   M   M   540
```

Figure 24B

```
1621  AGC TAC TGC ACT ACT GGG CAG ATG TGG GCC CGC AGC AGC TAC CTG  1665
541    S   Y   C   T   T   G   Q   M   W   A   R   S   S   Y   L   555

1666  GGG GCA GTG TTC AAT CTT ACC AGT GCT GAT CAT TTA TAT GTC AAC  1710
556    G   A   V   F   N   L   T   S   A   D   H   L   Y   V   N   570

1711  GTA TCT GAG CTC TCT CTG GTC AAT TTT GAG GAA TCT CAG ACG TTT  1755
571    V   S   E   L   S   L   V   N   F   E   E   S   Q   T   F   585

1756  TTC GGC TTA TAT AAG CTC GGT GGC GGT TCT GGT GGC GGT TCT GGT  1800
586    F   G   L   Y   K   L   G   G   G   S   G   G   G   S   G   600

1801  GGC GGT TCT GGT GGC GGA TCC GAA AAA AAG GAG CTG AGG AAA GTG  1845
601    G   G   S   G   G   G   S   E   K   K   E   L   R   K   V   615

1846  GCC CAT TTA ACA GGC AAG TCC AAC TCA AGG TCC ATG CCT CTG GAA  1890
616    A   H   L   T   G   K   S   N   S   R   S   M   P   L   E   630

1891  TGG GAA GAC ACC TAT GGA ATT GTC CTG CTT TCT GGA GTG AAG TAT  1935
631    W   E   D   T   Y   G   I   V   L   L   S   G   V   K   Y   645

1936  AAG AAG GGT GGC CTT GTG ATC AAT GAA ACT GGG CTG TAC TTT GTA  1980
646    K   K   G   G   L   V   I   N   E   T   G   L   Y   F   V   660

1981  TAT TCC AAA GTA TAC TTC CGG GGT CAA TCT TGC AAC AAC CTG CCC  2025
661    Y   S   K   V   Y   F   R   G   Q   S   C   N   N   L   P   675

2026  CTG AGC CAC AAG GTC TAC ATG AGG AAC TCT AAG TAT CCC CAG GAT  2070
676    L   S   H   K   V   Y   M   R   N   S   K   Y   P   Q   D   690

2071  CTG GTG ATG ATG GAG GGG AAG ATG ATG AGC TAC TGC ACT ACT GGG  2115
691    L   V   M   M   E   G   K   M   M   S   Y   C   T   T   G   705

2116  CAG ATG TGG GCC CGC AGC AGC TAC CTG GGG GCA GTG TTC AAT CTT  2160
706    Q   M   W   A   R   S   S   Y   L   G   A   V   F   N   L   720

2161  ACC AGT GCT GAT CAT TTA TAT GTC AAC GTA TCT GAG CTC TCT CTG  2205
721    T   S   A   D   H   L   Y   V   N   V   S   E   L   S   L   735

2206  GTC AAT TTT GAG GAA TCT CAG ACG TTT TTC GGC TTA TAT AAG CTC  2250
736    V   N   F   E   E   S   Q   T   F   F   G   L   Y   K   L   750

2251  TGA                                                          2253
751    *                                                          751
```

Figure 24C

Nucleic acid sequence and corresponding amino acid sequence of scTRAIL-AMAIZe
Construct G

```
  1    ATG GAC TGG ACC TGG CGC GTG TTT TGC CTG CTC GCC GTG GCT CCT    45
  1     M   D   W   T   W   R   V   F   C   L   L   A   V   A   P    15

46    GGG GCC CAC AGC CAG GTA CAG CTG GTG CAG TCT GGG GGA GGC ATG    90
 16     G   A   H   S   Q   V   Q   L   V   Q   S   G   G   G   M    30

91    GTA GAG CCT GGG GGG TCC CTT AGA CTC TCC TGT GCA GCC TCT GGA   135
 31     V   E   P   G   G   S   L   R   L   S   C   A   A   S   G    45

136    TTC ACT TTC AGT AAT GCC TGG ATG AGC TGG GTC CGC CAG GCT CCA   180
 46     F   T   F   S   N   A   W   M   S   W   V   R   Q   A   P    60

181    GGG AAG GGG CTG GAG TGG GTT GGC CGT ATA AAA AGC AAA GCT GGT   225
 61     G   K   G   L   E   W   V   G   R   I   K   S   K   A   G    75

226    GGT GGG ACA GCA GAG TAC GCT GCA CCC GTG AAA GGC AGA TTC ACC   270
 76     G   G   T   A   E   Y   A   A   P   V   K   G   R   F   T    90

271    ATC TCA AGA GAT GAT TCA CAA AAC ACG CTG TAT CTG CAA ATG AAC   315
 91     I   S   R   D   D   S   Q   N   T   L   Y   L   Q   M   N   105

316    AGC CTG AAA ACC GAC GAC ACA GCC GTG TAT TAC TGT ACC ACA CAT   360
106     S   L   K   T   D   D   T   A   V   Y   Y   C   T   T   H   120

361    GTC TAC GGT GCC CCC CGG AAC TGG GGC CAG GGA TCC CTG GTC ACC   405
121     V   Y   G   A   P   R   N   W   G   Q   G   S   L   V   T   135

406    GTC TCC TCA GCC TCC ACC AAG GGC CCA AAG CTT GAA GAA GGT GAA   450
136     V   S   S   A   S   T   K   G   P   K   L   E   E   G   E   150

451    TTT TCA GAA GCA CGC GTA CAG TCT GTG TTG ACT CAG CCG CCC TCA   495
151     F   S   E   A   R   V   Q   S   V   L   T   Q   P   P   S   165

496    GTG TCT GCG GCC CCA GGA CAG AAG GTC ACC ATC TCC TGC TCT GGA   540
166     V   S   A   A   P   G   Q   K   V   T   I   S   C   S   G   180

541    AGC AGC TCC AAC ATT GGA AAT AAT TAT GTC TCC TGG TAC GTT CAA   585
181     S   S   S   N   I   G   N   N   Y   V   S   W   Y   V   Q   195

586    CTC CCA GGA ACA GCC CCC AAA CTC CTC ATT TAT GAC AAT AAT AAG   630
196     L   P   G   T   A   P   K   L   L   I   Y   D   N   N   K   210

631    CGA TTC TCA GGA GTT CCT GAC CGA TTC TCT GGC TCC AAG TCT GGC   675
211     R   F   S   G   V   P   D   R   F   S   G   S   K   S   G   225

676    ACG TCA GCC ACC CTG GGC ATC ACC GGG CTC CAG ACT GGG GAC GAG   720
226     T   S   A   T   L   G   I   T   G   L   Q   T   G   D   E   240
```

Figure 25A

```
721  GCC GAT TAT TAC TGC GGA GCA TGG GAT GGC AGC CTG CGT GAA GCG  765
241   A   D   Y   Y   C   G   A   W   D   G   S   L   R   E   A   255

766  GTA TTC GGC GGA GGG ACC AAG GTC ACC GTC CTA GGT GCG GCC GCA  810
256   V   F   G   G   G   T   K   V   T   V   L   G   A   A   A   270

811  GTT GAG CTC GAG GCG GCC GCG GAT TAC AAA GAC GAT GAC GAT AAA  855
271   V   E   L   E   A   A   A   D   Y   K   D   D   D   D   K   285

856  GAA TTC GGA ACC TCT GAG GAA ACC ATT TCT ACA GTT CAA GAA AAG  900
286   E   F   G   T   S   E   E   T   I   S   T   V   Q   E   K   300

901  CAA CAA AAT ATT TCT CCC CTA GTG AGA GAA AGA GGT CCT CAG AGA  945
301   Q   Q   N   I   S   P   L   V   R   E   R   G   P   Q   R   315

946  GTA GCA GCT CAC ATA ACT GGG ACC AGA GGA AGA AGC AAC ACA TTG  990
316   V   A   A   H   I   T   G   T   R   G   R   S   N   T   L   330

991  TCT TCT CCA AAC TCC AAG AAT GAA AAG GCT CTG GGC CGC AAA ATA  1035
331   S   S   P   N   S   K   N   E   K   A   L   G   R   K   I   345

1036 AAC TCC TGG GAA TCA TCA AGG AGT GGG CAT TCA TTC CTG AGC AAC  1080
346   N   S   W   E   S   S   R   S   G   H   S   F   L   S   N   360

1081 TTG CAC TTG AGG AAT GGT GAA CTG GTC ATC CAT GAA AAA GGG TTT  1125
361   L   H   L   R   N   G   E   L   V   I   H   E   K   G   F   375

1126 TAC TAC ATC TAT TCC CAA ACA TAC TTT CGA TTT CAG GAG GAA ATA  1170
376   Y   Y   I   Y   S   Q   T   Y   F   R   F   Q   E   E   I   390

1171 AAA GAA AAC ACA AAG AAC GAC AAA CAA ATG GTC CAA TAT ATT TAC  1215
391   K   E   N   T   K   N   D   K   Q   M   V   Q   Y   I   Y   405

1216 AAA TAC ACA AGT TAT CCT GAC CCT ATA TTG TTG ATG AAA AGT GCT  1260
406   K   Y   T   S   Y   P   D   P   I   L   L   M   K   S   A   420

1261 AGA AAT AGT TGT TGG TCT AAA GAT GCA GAA TAT GGA CTC TAT TCC  1305
421   R   N   S   C   W   S   K   D   A   E   Y   G   L   Y   S   435

1306 ATC TAT CAA GGG GGA ATA TTT GAG CTT AAG GAA AAT GAC AGA ATT  1350
436   I   Y   Q   G   G   I   F   E   L   K   E   N   D   R   I   450

1351 TTT GTT TCT GTA ACA AAT GAG CAC TTG ATA GAC ATG GAC CAT GAA  1395
451   F   V   S   V   T   N   E   H   L   I   D   M   D   H   E   465

1396 GCC AGT TTT TTC GGG GCC TTT TTA GTT GGC GGT GGC GGT TCT GGT  1440
466   A   S   F   F   G   A   F   L   V   G   G   G   G   S   G   480

1441 GGC GGT TCT GGT GGC GGT TCT GGT GGC GGA TCA ACC TCT GAG GAA  1485
481   G   G   S   G   G   G   S   G   G   G   S   T   S   E   E   495

1486 ACC ATT TCT ACA GTT CAA GAA AAG CAA CAA AAT ATT TCT CCC CTA  1530
496   T   I   S   T   V   Q   E   K   Q   Q   N   I   S   P   L   510

1531 GTG AGA GAA AGA GGT CCT CAG AGA GTA GCA GCT CAC ATA ACT GGG  1575
511   V   R   E   R   G   P   Q   R   V   A   A   H   I   T   G   525
```

Figure 25B

```
1576  ACC AGA GGA AGA AGC AAC ACA TTG TCT TCT CCA AAC TCC AAG AAT  1620
526    T   R   G   R   S   N   T   L   S   S   P   N   S   K   N   540

1621  GAA AAG GCT CTG GGC CGC AAA ATA AAC TCC TGG GAA TCA TCA AGG  1665
541    E   K   A   L   G   R   K   I   N   S   W   E   S   S   R   555

1666  AGT GGG CAT TCA TTC CTG AGC AAC TTG CAC TTG AGG AAT GGT GAA  1710
556    S   G   H   S   F   L   S   N   L   H   L   R   N   G   E   570

1711  CTG GTC ATC CAT GAA AAA GGG TTT TAC TAC ATC TAT TCC CAA ACA  1755
571    L   V   I   H   E   K   G   F   Y   Y   I   Y   S   Q   T   585

1756  TAC TTT CGA TTT CAG GAG GAA ATA AAA GAA AAC ACA AAG AAC GAC  1800
586    Y   F   R   F   Q   E   E   I   K   E   N   T   K   N   D   600

1801  AAA CAA ATG GTC CAA TAT ATT TAC AAA TAC ACA AGT TAT CCT GAC  1845
601    K   Q   M   V   Q   Y   I   Y   K   Y   T   S   Y   P   D   615

1846  CCT ATA TTG TTG ATG AAA AGT GCT AGA AAT AGT TGT TGG TCT AAA  1890
616    P   I   L   L   M   K   S   A   R   N   S   C   W   S   K   630

1891  GAT GCA GAA TAT GGA CTC TAT TCC ATC TAT CAA GGG GGA ATA TTT  1935
631    D   A   E   Y   G   L   Y   S   I   Y   Q   G   G   I   F   645

1936  GAG CTT AAG GAA AAT GAC AGA ATT TTT GTT TCT GTA ACA AAT GAG  1980
646    E   L   K   E   N   D   R   I   F   V   S   V   T   N   E   660

1981  CAC TTG ATA GAC ATG GAC CAT GAA GCC AGT TTT TTC GGG GCC TTT  2025
661    H   L   I   D   M   D   H   E   A   S   F   F   G   A   F   675

2026  TTA GTT GGC GGT GGC GGT TCT GGT GGC GGT TCT GGT GGC GGT TCT  2070
676    L   V   G   G   G   G   S   G   G   G   S   G   G   G   S   690

2071  GGT GGC GGA TCC ACC TCT GAG GAA ACC ATT TCT ACA GTT CAA GAA  2115
691    G   G   G   S   T   S   E   E   T   I   S   T   V   Q   E   705

2116  AAG CAA CAA AAT ATT TCT CCC CTA GTG AGA GAA AGA GGT CCT CAG  2160
706    K   Q   Q   N   I   S   P   L   V   R   E   R   G   P   Q   720

2161  AGA GTA GCA GCT CAC ATA ACT GGG ACC AGA GGA AGA AGC AAC ACA  2205
721    R   V   A   A   H   I   T   G   T   R   G   R   S   N   T   735

2206  TTG TCT TCT CCA AAC TCC AAG AAT GAA AAG GCT CTG GGC CGC AAA  2250
736    L   S   S   P   N   S   K   N   E   K   A   L   G   R   K   750

2251  ATA AAC TCC TGG GAA TCA TCA AGG AGT GGG CAT TCA TTC CTG AGC  2295
751    I   N   S   W   E   S   S   R   S   G   H   S   F   L   S   765

2296  AAC TTG CAC TTG AGG AAT GGT GAA CTG GTC ATC CAT GAA AAA GGG  2340
766    N   L   H   L   R   N   G   E   L   V   I   H   E   K   G   780

2341  TTT TAC TAC ATC TAT TCC CAA ACA TAC TTT CGA TTT CAG GAG GAA  2385
781    F   Y   Y   I   Y   S   Q   T   Y   F   R   F   Q   E   E   795

2386  ATA AAA GAA AAC ACA AAG AAC GAC AAA CAA ATG GTC CAA TAT ATT  2430
796    I   K   E   N   T   K   N   D   K   Q   M   V   Q   Y   I   810
```

Figure 25C

```
2431  TAC AAA TAC ACA AGT TAT CCT GAC CCT ATA TTG TTG ATG AAA AGT  2475
811    Y   K   Y   T   S   Y   P   D   P   I   L   L   M   K   S   825

2476  GCT AGA AAT AGT TGT TGG TCT AAA GAT GCA GAA TAT GGA CTC TAT  2520
826    A   R   N   S   C   W   S   K   D   A   E   Y   G   L   Y   840

2521  TCC ATC TAT CAA GGG GGA ATA TTT GAG CTT AAG GAA AAT GAC AGA  2565
841    S   I   Y   Q   G   G   I   F   E   L   K   E   N   D   R   855

2566  ATT TTT GTT TCT GTA ACA AAT GAG CAC TTG ATA GAC ATG GAC CAT  2610
856    I   F   V   S   V   T   N   E   H   L   I   D   M   D   H   870

2611  GAA GCC AGT TTT TTC GGG GCC TTT TTA GTT GGC TGA              2646
871    E   A   S   F   F   G   A   F   L   V   G   *               881
```

Figure 25D

Nucleic acid sequence and corresponding amino acid sequence of scTNF-AMAIZe
Construct H

```
  1   ATG GAC TGG ACC TGG CGC GTG TTT TGC CTG CTC GCC GTG GCT CCT    45
  1    M   D   W   T   W   R   V   F   C   L   L   A   V   A   P    15

46   GGG GCC CAC AGC CAG GTA CAG CTG GTG CAG TCT GGG GGA GGC ATG    90
 16    G   A   H   S   Q   V   Q   L   V   Q   S   G   G   G   M    30

91   GTA GAG CCT GGG GGG TCC CTT AGA CTC TCC TGT GCA GCC TCT GGA   135
 31    V   E   P   G   G   S   L   R   L   S   C   A   A   S   G    45

136   TTC ACT TTC AGT AAT GCC TGG ATG AGC TGG GTC CGC CAG GCT CCA   180
 46    F   T   F   S   N   A   W   M   S   W   V   R   Q   A   P    60

181   GGG AAG GGG CTG GAG TGG GTT GGC CGT ATA AAA AGC AAA GCT GGT   225
 61    G   K   G   L   E   W   V   G   R   I   K   S   K   A   G    75

226   GGT GGG ACA GCA GAG TAC GCT GCA CCC GTG AAA GGC AGA TTC ACC   270
 76    G   G   T   A   E   Y   A   A   P   V   K   G   R   F   T    90

271   ATC TCA AGA GAT GAT TCA CAA AAC ACG CTG TAT CTG CAA ATG AAC   315
 91    I   S   R   D   D   S   Q   N   T   L   Y   L   Q   M   N   105

316   AGC CTG AAA ACC GAC GAC ACA GCC GTG TAT TAC TGT ACC ACA CAT   360
106    S   L   K   T   D   D   T   A   V   Y   Y   C   T   T   H   120

361   GTC TAC GGT GCC CCC CGG AAC TGG GGC CAG GGA TCC CTG GTC ACC   405
121    V   Y   G   A   P   R   N   W   G   Q   G   S   L   V   T   135

406   GTC TCC TCA GCC TCC ACC AAG GGC CCA AAG CTT GAA GAA GGT GAA   450
136    V   S   S   A   S   T   K   G   P   K   L   E   E   G   E   150

451   TTT TCA GAA GCA CGC GTA CAG TCT GTG TTG ACT CAG CCG CCC TCA   495
151    F   S   E   A   R   V   Q   S   V   L   T   Q   P   P   S   165

496   GTG TCT GCG GCC CCA GGA CAG AAG GTC ACC ATC TCC TGC TCT GGA   540
166    V   S   A   A   P   G   Q   K   V   T   I   S   C   S   G   180

541   AGC AGC TCC AAC ATT GGA AAT AAT TAT GTC TCC TGG TAC GTT CAA   585
181    S   S   S   N   I   G   N   N   Y   V   S   W   Y   V   Q   195

586   CTC CCA GGA ACA GCC CCC AAA CTC CTC ATT TAT GAC AAT AAT AAG   630
196    L   P   G   T   A   P   K   L   L   I   Y   D   N   N   K   210

631   CGA TTC TCA GGA GTT CCT GAC CGA TTC TCT GGC TCC AAG TCT GGC   675
211    R   F   S   G   V   P   D   R   F   S   G   S   K   S   G   225

676   ACG TCA GCC ACC CTG GGC ATC ACC GGG CTC CAG ACT GGG GAC GAG   720
226    T   S   A   T   L   G   I   T   G   L   Q   T   G   D   E   240

721   GCC GAT TAT TAC TGC GGA GCA TGG GAT GGC AGC CTG CGT GAA GCG   765
241    A   D   Y   Y   C   G   A   W   D   G   S   L   R   E   A   255
```

Figure 26A

```
766   GTA TTC GGC GGA GGG ACC AAG GTC ACC GTC CTA GGT GCG GCC GCA   810
256    V   F   G   G   G   T   K   V   T   V   L   G   A   A   A   270

811   GTT GAG CTC GAG GCG GCC GCG GAT TAC AAA GAC GAT GAC GAT AAA   855
271    V   E   L   E   A   A   A   D   Y   K   D   D   D   D   K   285

856   GAA TTC GGA TCA TCT TCT CGA ACC CCG AGT GAC AAG CCT GTA GCC   900
286    E   F   G   S   S   S   R   T   P   S   D   K   P   V   A   300

901   CAT GTT GTA GCA AAC CCT CAA GCT GAG GGG CAG CTC CAG TGG CTG   945
301    H   V   V   A   N   P   Q   A   E   G   Q   L   Q   W   L   315

946   AAC CGC CGG GCC AAT GCC CTC CTG GCC AAT GGC GTG GAG CTG AGA   990
316    N   R   R   A   N   A   L   L   A   N   G   V   E   L   R   330

991   GAT AAC CAG CTG GTG GTG CCA TCA GAG GGC CTG TAC CTC ATC TAC  1035
331    D   N   Q   L   V   V   P   S   E   G   L   Y   L   I   Y   345

1036  TCC CAG GTC CTC TTC AAG GGC CAA GGC TGC CCC TCC ACC CAT GTG  1080
346    S   Q   V   L   F   K   G   Q   G   C   P   S   T   H   V   360

1081  CTC CTC ACC CAC ACC ATC AGC CGC ATC GCC GTC TCC TAC CAG ACC  1125
361    L   L   T   H   T   I   S   R   I   A   V   S   Y   Q   T   375

1126  AAG GTC AAC CTC CTC TCT GCC ATC AAG AGC CCC TGC CAG AGG GAG  1170
376    K   V   N   L   L   S   A   I   K   S   P   C   Q   R   E   390

1171  ACC CCA GAG GGG GCT GAG GCC AAG CCC TGG TAT GAG CCC ATC TAT  1215
391    T   P   E   G   A   E   A   K   P   W   Y   E   P   I   Y   405

1216  CTG GGA GGG GTC TTC CAG CTG GAG AAG GGT GAC CGA CTC AGC GCT  1260
406    L   G   G   V   F   Q   L   E   K   G   D   R   L   S   A   420

1261  GAG ATC AAT CGG CCC GAC TAT CTC GAC TTT GCC GAG TCT GGG CAG  1305
421    E   I   N   R   P   D   Y   L   D   F   A   E   S   G   Q   435

1306  GTC TAC TTT GGG ATC ATT GCC CTG GGT GGC GGT TCT GGT GGC GGT  1350
436    V   Y   F   G   I   I   A   L   G   G   G   S   G   G   G   450

1351  TCT GGT GGC GGT TCT GGT GGC GGA TCA TCA TCT TCT CGA ACC CCG  1395
451    S   G   G   G   S   G   G   G   S   S   S   S   R   T   P   465

1396  AGT GAC AAG CCT GTA GCC CAT GTT GTA GCA AAC CCT CAA GCT GAG  1440
466    S   D   K   P   V   A   H   V   V   A   N   P   Q   A   E   480

1441  GGG CAG CTC CAG TGG CTG AAC CGC CGG GCC AAT GCC CTC CTG GCC  1485
481    G   Q   L   Q   W   L   N   R   R   A   N   A   L   L   A   495

1486  AAT GGC GTG GAG CTG AGA GAT AAC CAG CTG GTG GTG CCA TCA GAG  1530
496    N   G   V   E   L   R   D   N   Q   L   V   V   P   S   E   510

1531  GGC CTG TAC CTC ATC TAC TCC CAG GTC CTC TTC AAG GGC CAA GGC  1575
511    G   L   Y   L   I   Y   S   Q   V   L   F   K   G   Q   G   525

1576  TGC CCC TCC ACC CAT GTG CTC CTC ACC CAC ACC ATC AGC CGC ATC  1620
526    C   P   S   T   H   V   L   L   T   H   T   I   S   R   I   540
```

Figure 26B

```
1621  GCC GTC TCC TAC CAG ACC AAG GTC AAC CTC CTC TCT GCC ATC AAG  1665
541    A   V   S   Y   Q   T   K   V   N   L   L   S   A   I   K   555

1666  AGC CCC TGC CAG AGG GAG ACC CCA GAG GGG GCT GAG GCC AAG CCC  1710
556    S   P   C   Q   R   E   T   P   E   G   A   E   A   K   P   570

1711  TGG TAT GAG CCC ATC TAT CTG GGA GGG GTC TTC CAG CTG GAG AAG  1755
571    W   Y   E   P   I   Y   L   G   G   V   F   Q   L   E   K   585

1756  GGT GAC CGA CTC AGC GCT GAG ATC AAT CGG CCC GAC TAT CTC GAC  1800
586    G   D   R   L   S   A   E   I   N   R   P   D   Y   L   D   600

1801  TTT GCC GAG TCT GGG CAG GTC TAC TTT GGG ATC ATT GCC CTG GGT  1845
601    F   A   E   S   G   Q   V   Y   F   G   I   I   A   L   G   615

1846  GGC GGT TCT GGT GGC GGT TCT GGT GGC GGT TCT GGT GGC GGA TCA  1890
616    G   G   S   G   G   G   S   G   G   G   S   G   G   G   S   630

1891  TCA TCT TCT CGA ACC CCG AGT GAC AAG CCT GTA GCC CAT GTT GTA  1935
631    S   S   S   R   T   P   S   D   K   P   V   A   H   V   V   645

1936  GCA AAC CCT CAA GCT GAG GGG CAG CTC CAG TGG CTG AAC CGC CGG  1980
646    A   N   P   Q   A   E   G   Q   L   Q   W   L   N   R   R   660

1981  GCC AAT GCC CTC CTG GCC AAT GGC GTG GAG CTG AGA GAT AAC CAG  2025
661    A   N   A   L   L   A   N   G   V   E   L   R   D   N   Q   675

2026  CTG GTG GTG CCA TCA GAG GGC CTG TAC CTC ATC TAC TCC CAG GTC  2070
676    L   V   V   P   S   E   G   L   Y   L   I   Y   S   Q   V   690

2071  CTC TTC AAG GGC CAA GGC TGC CCC TCC ACC CAT GTG CTC CTC ACC  2115
691    L   F   K   G   Q   G   C   P   S   T   H   V   L   L   T   705

2116  CAC ACC ATC AGC CGC ATC GCC GTC TCC TAC CAG ACC AAG GTC AAC  2160
706    H   T   I   S   R   I   A   V   S   Y   Q   T   K   V   N   720

2161  CTC CTC TCT GCC ATC AAG AGC CCC TGC CAG AGG GAG ACC CCA GAG  2205
721    L   L   S   A   I   K   S   P   C   Q   R   E   T   P   E   735

2206  GGG GCT GAG GCC AAG CCC TGG TAT GAG CCC ATC TAT CTG GGA GGG  2250
736    G   A   E   A   K   P   W   Y   E   P   I   Y   L   G   G   750

2251  GTC TTC CAG CTG GAG AAG GGT GAC CGA CTC AGC GCT GAG ATC AAT  2295
751    V   F   Q   L   E   K   G   D   R   L   S   A   E   I   N   765

2296  CGG CCC GAC TAT CTC GAC TTT GCC GAG TCT GGG CAG GTC TAC TTT  2340
766    R   P   D   Y   L   D   F   A   E   S   G   Q   V   Y   F   780

2341  GGG ATC ATT GCC CTG TGA                                      2358
781    G   I   I   A   L   *                                       785
```

Figure 26C

SEQUENCE LISTING

<160> NUMBER OF SEQ ID NOS: 41

<210> SEQ ID NO 1
<211> LENGTH: 8
<212> TYPE: PRT
<213> ORGANISM: Artificial Sequence Sequence
<220> FEATURE:
<223> OTHER INFORMATION: Description of Artificial Sequence: Synthetic
      flag-tag peptide sequence

<400> SEQUENCE: 1

Asp Tyr Lys Asp Asp Asp Asp Lys
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Peptide
      linker sequence

<400> SEQUENCE: 2

Gly Gly Gly Ser Gly Gly Gly Ser Gly Gly Gly Ser
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Peptide
      linker sequence

<400> SEQUENCE: 3

Gly Gly Gly Ser Gly Gly Gly Ser Gly Gly Gly Ser Gly Gly Gly Ser
1               5                   10                  15

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Linker
      sequence

<400> SEQUENCE: 4
ggtggcggtt ctggtggcgg ttctggtggc ggatcc                                 36

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Linker
      sequence

<400> SEQUENCE: 5
ggtggcggtt ctggtggcgg ttctggtggc ggttctggtg gcggatcc                    48

<210> SEQ ID NO 6
<211> LENGTH: 84
<212> TYPE: DNA
<213> ORGANISM: Artificial Sequence
<220> FEATURE:
<223> OTHER INFORMATION: Description of Artificial Sequence: scTNF
      Primer I

<400> SEQUENCE: 6
tcgattaagc ttcccggggg atccgccacc agaaccgcca ccagaaccgc cacccagagc    60
gatgataccg aagtaaacct gacc    84

<210> SEQ ID NO 7
<211> LENGTH: 97
<212> TYPE: DNA
<213> ORGANISM: Artificial Sequence
<220> FEATURE:
<223> OTHER INFORMATION: Description of Artificial Sequence: scTNF
      Primer II

<400> SEQUENCE: 7
atcgattaag cttcccgggg gatccgccac cagaaccgcc accagaaccg ccaccagaac    60
cgccacccag agcgatgata ccgaagtaaa cctgacc    97

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: scTNF
      Primer III

<400> SEQUENCE: 8
ccccgaattc ggatcctctt ctcgtacccc gtctgacaaa ccg    43

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: scTNF
      Primer IV

<400> SEQUENCE: 9 ggggggggaag cttatcgata gttagatatc atcacagagc gatgataccg aag    53

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: scTNF
      Primer V

<400> SEQUENCE: 10
cctgtacctg atctactccc aggttctgtt caaaggccag g    41

<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: cys-scTNF
      Primer VI

<400> SEQUENCE: 11
aattcattaa agaggagaaa ttaactatgg gagagctcat cgaaggtcgc tgcgccggtg    60
gatctggtca tcatcatcac catcacggct cagacgg    97

<210> SEQ ID NO 12
<211> LENGTH: 97
<212> TYPE: DNA

```
<213> ORGANISM: Artificial Sequence
<220> FEATURE:
<223> OTHER INFORMATION: Description of Artificial Sequence: cys-scTNF
      Primer VII

<400> SEQUENCE: 12
cgctccgtct gagccgtgat ggtgatgatg atgaccagat ccaccggcgc agcgaccttc    60
gatgagctct cccatagtta atttctcctc tttaatg                              97

<210> SEQ ID NO 13
<211> LENGTH: 100
<212> TYPE: DNA
<213> ORGANISM: Artificial Sequence
<220> FEATURE:
<223> OTHER INFORMATION: Description of Artificial Sequence: Primer
      FasL#1R

<400> SEQUENCE: 13
atcgatttct agacccgggg gatccgccac cagaaccgcc accagaaccg ccaccagaac    60
cgccaccgag cttatataag ccgaaaaacg tctgagattc                          100

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Primer
      FasL#2F

<400> SEQUENCE: 14
ggggtagcgg ccgcgctgtc gacgattaca aagac                                35

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer
      FasL#3F

<400> SEQUENCE: 15
agaaaaaaag gagctgagga aagtgg                                          26

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Primer
      FasL#4F

<400> SEQUENCE: 16
ggggcggatc cgaaaaaaag gagctgagga aagtgg                               36

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Primer
      FasL#5R

<400> SEQUENCE: 17
ggggcctcta gaatcgatgg tcagagctta tataagccga aaaacgtctg                50
```

```
<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Primer
      HA-IF

<400> SEQUENCE: 18
cgccatggct atcatctacc tcatcctcct gttcaccgct gtgcggggag c          51

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Primer
      HA-IIR

<400> SEQUENCE: 19
ggccgctgcc ccgcacagcg gtgaacagga ggatgaggta gatgatagcc atggcggtac  60

<210> SEQ ID NO 20
<211> LENGTH: 106
<212> TYPE: DNA
<213> ORGANISM: Artificial Sequence
<220> FEATURE:
<223> OTHER INFORMATION: Description of Artificial Sequence: Primer
      TRAIL#1R

<400> SEQUENCE: 20
atcgatttct agacccgggg gatccgccac cagaaccgcc accagaaccg ccaccagaac  60
cgccaccgcc aactaaaaag gccccgaaaa aactggcttc atggtc               106

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Primer
      TRAIL#2F

<400> SEQUENCE: 21
ggggtagaat tcggaacctc tgaggaaacc atttctacag ttcaag                46

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer
      TRAIL#3F

<400> SEQUENCE: 22
aacctctgag gaaaccattt ctacag                                      26

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Primer
      TRAIL#4F

<400> SEQUENCE: 23
ggggcggatc cacctctgag gaaaccattt ctacag                           36
```

<210> SEQ ID NO 24
<211> LENGTH: 53
<212> TYPE: DNA
<213> ORGANISM: Artificial Sequence
<220> FEATURE:
<223> OTHER INFORMATION: Description of Artificial Sequence: Primer
      TRAIL#5R

<400> SEQUENCE: 24
ggggcctcta gaatcgatgg tcagccaact aaaaaggccc cgaaaaaact ggc       53

<210> SEQ ID NO 25
<211> LENGTH: 1506
<212> TYPE: DNA
<213> ORGANISM: Artificial Sequence
<220> FEATURE:
<223> OTHER INFORMATION: Description of Artificial Sequence: scTNF-L
      short chain
<220> FEATURE:
<221> NAME/KEY: CDS
<222> LOCATION: (1)..(1503)

<400> SEQUENCE: 25

```
atg aga gga tcg cat cac cat cac cat cac gga tca gcg tcg tct tct        48
Met Arg Gly Ser His His His His His His Gly Ser Ala Ser Ser Ser
1               5                   10                  15 tct cgt acc ccg tct gac aaa ccg gtt gct cac gtt gtt gca aac ccg        96
Ser Arg Thr Pro Ser Asp Lys Pro Val Ala His Val Val Ala Asn Pro
            20                  25                  30 cag gct gaa ggt caa ctg caa tgg ctg aac cgt cgt gct aac gct ctg       144
Gln Ala Glu Gly Gln Leu Gln Trp Leu Asn Arg Arg Ala Asn Ala Leu
        35                  40                  45 ctg gct aac ggt gtt gaa ctg cgt gac aac cag ctg gtt gtt ccg tct       192
Leu Ala Asn Gly Val Glu Leu Arg Asp Asn Gln Leu Val Val Pro Ser
    50                  55                  60 gaa ggc ctg tac ctg atc tac tcc cag gtt ctg ttc aaa ggc cag ggc       240
Glu Gly Leu Tyr Leu Ile Tyr Ser Gln Val Leu Phe Lys Gly Gln Gly
65                  70                  75                  80 tgc ccg tcc acc cac gtt ctg ctg acc cac acc atc tct cgt atc gct       288
Cys Pro Ser Thr His Val Leu Leu Thr His Thr Ile Ser Arg Ile Ala
                85                  90                  95 gtt tcc tac cag acc aaa gta aac ctg ctg tct gca atc aaa tct ccg       336
Val Ser Tyr Gln Thr Lys Val Asn Leu Leu Ser Ala Ile Lys Ser Pro
            100                 105                 110 tgc cag cgt gaa acc ccg gaa ggt gct gaa gct aaa ccg tgg tac gaa       384
Cys Gln Arg Glu Thr Pro Glu Gly Ala Glu Ala Lys Pro Trp Tyr Glu
        115                 120                 125 ccg atc tac ctg ggt ggc gtt ttt caa ctg gag aaa ggt gac cgt ctg       432
Pro Ile Tyr Leu Gly Gly Val Phe Gln Leu Glu Lys Gly Asp Arg Leu
    130                 135                 140 tct gca gaa att aac cgt ccg gac tac ctg gac ttc gca gaa tct ggt       480
Ser Ala Glu Ile Asn Arg Pro Asp Tyr Leu Asp Phe Ala Glu Ser Gly
145                 150                 155                 160 cag gtt tac ttc ggt atc atc gct ctg ggt ggc ggt tct ggt ggc ggt       528
Gln Val Tyr Phe Gly Ile Ile Ala Leu Gly Gly Gly Ser Gly Gly Gly
                165                 170                 175 tct ggt ggc gga tcc tct tct cgt acc ccg tct gac aaa ccg gtt gct       576
Ser Gly Gly Gly Ser Ser Ser Arg Thr Pro Ser Asp Lys Pro Val Ala
            180                 185                 190 cac gtt gtt gca aac ccg cag gct gaa ggt caa ctg caa tgg ctg aac       624
His Val Val Ala Asn Pro Gln Ala Glu Gly Gln Leu Gln Trp Leu Asn
        195                 200                 205
```

```
cgt cgt gct aac gct ctg ctg gct aac ggt gtt gaa ctg cgt gac aac      672
Arg Arg Ala Asn Ala Leu Leu Ala Asn Gly Val Glu Leu Arg Asp Asn
210                 215                 220 cag ctg gtt gtt ccg tct gaa ggc ctg tac ctg atc tac tcc cag gtt      720
Gln Leu Val Val Pro Ser Glu Gly Leu Tyr Leu Ile Tyr Ser Gln Val
225                 230                 235                 240 ctg ttc aaa ggc cag ggc tgc ccg tcc acc cac gtt ctg ctg acc cac      768
Leu Phe Lys Gly Gln Gly Cys Pro Ser Thr His Val Leu Leu Thr His
                245                 250                 255 acc atc tct cgt atc gct gtt tcc tac cag acc aaa gta aac ctg ctg      816
Thr Ile Ser Arg Ile Ala Val Ser Tyr Gln Thr Lys Val Asn Leu Leu
            260                 265                 270 tct gca atc aaa tct ccg tgc cag cgt gaa acc ccg gaa ggt gct gaa      864
Ser Ala Ile Lys Ser Pro Cys Gln Arg Glu Thr Pro Glu Gly Ala Glu
        275                 280                 285 gct aaa ccg tgg tac gaa ccg atc tac ctg ggt ggc gtt ttt caa ctg      912
Ala Lys Pro Trp Tyr Glu Pro Ile Tyr Leu Gly Gly Val Phe Gln Leu
    290                 295                 300 gag aaa ggt gac cgt ctg tct gca gaa att aac cgt ccg gac tac ctg      960
Glu Lys Gly Asp Arg Leu Ser Ala Glu Ile Asn Arg Pro Asp Tyr Leu
305                 310                 315                 320 gac ttc gca gaa tct ggt cag gtt tac ttc ggt atc atc gct ctg ggt     1008
Asp Phe Ala Glu Ser Gly Gln Val Tyr Phe Gly Ile Ile Ala Leu Gly
                325                 330                 335 ggc ggt tct ggt ggc ggt tct ggt ggc gga tcc tct tct cgt acc ccg     1056
Gly Gly Ser Gly Gly Gly Ser Gly Gly Gly Ser Ser Ser Arg Thr Pro
            340                 345                 350 tct gac aaa ccg gtt gct cac gtt gtt gca aac ccg cag gct gaa ggt     1104
Ser Asp Lys Pro Val Ala His Val Val Ala Asn Pro Gln Ala Glu Gly
        355                 360                 365 caa ctg caa tgg ctg aac cgt cgt gct aac gct ctg ctg gct aac ggt     1152
Gln Leu Gln Trp Leu Asn Arg Arg Ala Asn Ala Leu Leu Ala Asn Gly
    370                 375                 380 gtt gaa ctg cgt gac aac cag ctg gtt gtt ccg tct gaa ggc ctg tac     1200
Val Glu Leu Arg Asp Asn Gln Leu Val Val Pro Ser Glu Gly Leu Tyr
385                 390                 395                 400 ctg atc tac tcc cag gtt ctg ttc aaa ggc cag ggc tgc ccg tcc acc     1248
Leu Ile Tyr Ser Gln Val Leu Phe Lys Gly Gln Gly Cys Pro Ser Thr
                405                 410                 415 cac gtt ctg ctg acc cac acc atc tct cgt atc gct gtt tcc tac cag     1296
His Val Leu Leu Thr His Thr Ile Ser Arg Ile Ala Val Ser Tyr Gln
            420                 425                 430 acc aaa gta aac ctg ctg tct gca atc aaa tct ccg tgc cag cgt gaa     1344
Thr Lys Val Asn Leu Leu Ser Ala Ile Lys Ser Pro Cys Gln Arg Glu
        435                 440                 445 acc ccg gaa ggt gct gaa gct aaa ccg tgg tac gaa ccg atc tac ctg     1392
Thr Pro Glu Gly Ala Glu Ala Lys Pro Trp Tyr Glu Pro Ile Tyr Leu
    450                 455                 460 ggt ggc gtt ttt caa ctg gag aaa ggt gac cgt ctg tct gca gaa att     1440
Gly Gly Val Phe Gln Leu Glu Lys Gly Asp Arg Leu Ser Ala Glu Ile
465                 470                 475                 480 aac cgt ccg gac tac ctg gac ttc gca gaa tct ggt cag gtt tac ttc     1488
Asn Arg Pro Asp Tyr Leu Asp Phe Ala Glu Ser Gly Gln Val Tyr Phe
                485                 490                 495 ggt atc atc gct ctg tga                                             1506
Gly Ile Ile Ala Leu
            500

<210> SEQ ID NO 26
<211> LENGTH: 501
```

<212> TYPE: PRT
<213> ORGANISM: Artificial Sequence
<220> FEATURE:
<223> OTHER INFORMATION: Description of Artificial Sequence: scTNF-L
      short chain peptide

<400> SEQUENCE: 26

Met Arg Gly Ser His His His His His His Gly Ser Ala Ser Ser Ser
1               5                   10                  15

Ser Arg Thr Pro Ser Asp Lys Pro Val Ala His Val Val Ala Asn Pro
            20                  25                  30

Gln Ala Glu Gly Gln Leu Gln Trp Leu Asn Arg Arg Ala Asn Ala Leu
        35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asp Phe Ala Glu Ser Gly
145                 150                 155                 160

Gln Val Tyr Phe Gly Ile Ile Ala Leu Gly Gly Ser Gly Gly Gly
                165                 170                 175

Ser Gly Gly Gly Ser Ser Ser Arg Thr Pro Ser Asp Lys Pro Val Ala
            180                 185                 190

His Val Val Ala Asn Pro Gln Ala Glu Gly Gln Leu Gln Trp Leu Asn
        195                 200                 205

Arg Arg Ala Asn Ala Leu Leu Ala Asn Gly Val Glu Leu Arg Asp Asn
    210                 215                 220

Gln Leu Val Val Pro Ser Glu Gly Leu Tyr Leu Ile Tyr Ser Gln Val
225                 230                 235                 240

Leu Phe Lys Gly Gln Gly Cys Pro Ser Thr His Val Leu Leu Thr His
                245                 250                 255

Thr Ile Ser Arg Ile Ala Val Ser Tyr Gln Thr Lys Val Asn Leu Leu
            260                 265                 270

Ser Ala Ile Lys Ser Pro Cys Gln Arg Glu Thr Pro Glu Gly Ala Glu
        275                 280                 285

Ala Lys Pro Trp Tyr Glu Pro Ile Tyr Leu Gly Gly Val Phe Gln Leu
    290                 295                 300

Glu Lys Gly Asp Arg Leu Ser Ala Glu Ile Asn Arg Pro Asp Tyr Leu
305                 310                 315                 320

Asp Phe Ala Glu Ser Gly Gln Val Tyr Phe Gly Ile Ile Ala Leu Gly
                325                 330                 335

Gly Gly Ser Gly Gly Gly Ser Gly Gly Ser Ser Ser Arg Thr Pro
            340                 345                 350

Ser Asp Lys Pro Val Ala His Val Val Ala Asn Pro Gln Ala Glu Gly
        355                 360                 365

Gln Leu Gln Trp Leu Asn Arg Arg Ala Asn Ala Leu Leu Ala Asn Gly
    370                 375                 380

```
Val Glu Leu Arg Asp Asn Gln Leu Val Val Pro Ser Glu Gly Leu Tyr
385                 390                 395                 400

Leu Ile Tyr Ser Gln Val Leu Phe Lys Gly Gln Gly Cys Pro Ser Thr
            405                 410                 415

His Val Leu Leu Thr His Thr Ile Ser Arg Ile Ala Val Ser Tyr Gln
        420                 425                 430

Thr Lys Val Asn Leu Leu Ser Ala Ile Lys Ser Pro Cys Gln Arg Glu
    435                 440                 445

Thr Pro Glu Gly Ala Glu Ala Lys Pro Trp Tyr Glu Pro Ile Tyr Leu
450                 455                 460

Gly Gly Val Phe Gln Leu Glu Lys Gly Asp Arg Leu Ser Ala Glu Ile
465                 470                 475                 480

Asn Arg Pro Asp Tyr Leu Asp Phe Ala Glu Ser Gly Gln Val Tyr Phe
                485                 490                 495

Gly Ile Ile Ala Leu
            500

<210> SEQ ID NO 27
<211> LENGTH: 1542
<212> TYPE: DNA
<213> ORGANISM: Artificial Sequence
<220> FEATURE:
<223> OTHER INFORMATION: Description of Artificial Sequence: cys-scTNF-L
      short chain
<220> FEATURE:
<221> NAME/KEY: CDS
<222> LOCATION: (1)..(1539)

<400> SEQUENCE: 27 atg gga gag ctc atc gaa ggt cgc tgc gcc ggt gga tct ggt cat cat        48
Met Gly Glu Leu Ile Glu Gly Arg Cys Ala Gly Gly Ser Gly His His
1               5                   10                  15 cat cac cat cac ggc tca gac gga gcg tcg tct tct tct cgt acc ccg        96
His His His His Gly Ser Asp Gly Ala Ser Ser Ser Ser Arg Thr Pro
            20                  25                  30 tct gac aaa ccg gtt gct cac gtt gtt gca aac ccg cag gct gaa ggt       144
Ser Asp Lys Pro Val Ala His Val Val Ala Asn Pro Gln Ala Glu Gly
        35                  40                  45 caa ctg caa tgg ctg aac cgt cgt gct aac gct ctg ctg gct aac ggt       192
Gln Leu Gln Trp Leu Asn Arg Arg Ala Asn Ala Leu Leu Ala Asn Gly
    50                  55                  60 gtt gaa ctg cgt gac aac cag ctg gtt gtt ccg tct gaa ggc ctg tac       240
Val Glu Leu Arg Asp Asn Gln Leu Val Val Pro Ser Glu Gly Leu Tyr
65                  70                  75                  80 ctg atc tac tcc cag gtt ctg ttc aaa ggc cag ggc tgc ccg tcc acc       288
Leu Ile Tyr Ser Gln Val Leu Phe Lys Gly Gln Gly Cys Pro Ser Thr
                85                  90                  95 cac gtt ctg ctg acc cac acc atc tct cgt atc gct gtt tcc tac cag       336
His Val Leu Leu Thr His Thr Ile Ser Arg Ile Ala Val Ser Tyr Gln
            100                 105                 110 acc aaa gta aac ctg ctg tct gca atc aaa tct ccg tgc cag cgt gaa       384
Thr Lys Val Asn Leu Leu Ser Ala Ile Lys Ser Pro Cys Gln Arg Glu
        115                 120                 125 acc ccg gaa ggt gct gaa gct aaa ccg tgg tac gaa ccg atc tac ctg       432
Thr Pro Glu Gly Ala Glu Ala Lys Pro Trp Tyr Glu Pro Ile Tyr Leu
    130                 135                 140 ggt ggc gtt ttt caa ctg gag aaa ggt gac cgt ctg tct gca gaa att       480
Gly Gly Val Phe Gln Leu Glu Lys Gly Asp Arg Leu Ser Ala Glu Ile
145                 150                 155                 160
```

-continued

| | |
|---|---|
| aac cgt ccg gac tac ctg gac ttc gca gaa tct ggt cag gtt tac ttc<br>Asn Arg Pro Asp Tyr Leu Asp Phe Ala Glu Ser Gly Gln Val Tyr Phe<br>165 170 175 | 528 |
| ggt atc atc gct ctg ggt ggc ggt tct ggt ggc ggt tct ggt ggc gga<br>Gly Ile Ile Ala Leu Gly Gly Gly Ser Gly Gly Gly Ser Gly Gly Gly<br>180 185 190 | 576 |
| tcc tct tct cgt acc ccg tct gac aaa ccg gtt gct cac gtt gtt gca<br>Ser Ser Ser Arg Thr Pro Ser Asp Lys Pro Val Ala His Val Val Ala<br>195 200 205 | 624 |
| aac ccg cag gct gaa ggt caa ctg caa tgg ctg aac cgt cgt gct aac<br>Asn Pro Gln Ala Glu Gly Gln Leu Gln Trp Leu Asn Arg Arg Ala Asn<br>210 215 220 | 672 |
| gct ctg ctg gct aac ggt gtt gaa ctg cgt gac aac cag ctg gtt gtt<br>Ala Leu Leu Ala Asn Gly Val Glu Leu Arg Asp Asn Gln Leu Val Val<br>225 230 235 240 | 720 |
| ccg tct gaa ggc ctg tac ctg atc tac tcc cag gtt ctg ttc aaa ggc<br>Pro Ser Glu Gly Leu Tyr Leu Ile Tyr Ser Gln Val Leu Phe Lys Gly<br>245 250 255 | 768 |
| cag ggc tgc ccg tcc acc cac gtt ctg ctg acc cac acc atc tct cgt<br>Gln Gly Cys Pro Ser Thr His Val Leu Leu Thr His Thr Ile Ser Arg<br>260 265 270 | 816 |
| atc gct gtt tcc tac cag acc aaa gta aac ctg ctg tct gca atc aaa<br>Ile Ala Val Ser Tyr Gln Thr Lys Val Asn Leu Leu Ser Ala Ile Lys<br>275 280 285 | 864 |
| tct ccg tgc cag cgt gaa acc ccg gaa ggt gct gaa gct aaa ccg tgg<br>Ser Pro Cys Gln Arg Glu Thr Pro Glu Gly Ala Glu Ala Lys Pro Trp<br>290 295 300 | 912 |
| tac gaa ccg atc tac ctg ggt ggc gtt ttt caa ctg gag aaa ggt gac<br>Tyr Glu Pro Ile Tyr Leu Gly Gly Val Phe Gln Leu Glu Lys Gly Asp<br>305 310 315 320 | 960 |
| cgt ctg tct gca gaa att aac cgt ccg gac tac ctg gac ttc gca gaa<br>Arg Leu Ser Ala Glu Ile Asn Arg Pro Asp Tyr Leu Asp Phe Ala Glu<br>325 330 335 | 1008 |
| tct ggt cag gtt tac ttc ggt atc atc gct ctg ggt ggc ggt tct ggt<br>Ser Gly Gln Val Tyr Phe Gly Ile Ile Ala Leu Gly Gly Gly Ser Gly<br>340 345 350 | 1056 |
| ggc ggt tct ggt ggc gga tcc tct tct cgt acc ccg tct gac aaa ccg<br>Gly Gly Ser Gly Gly Gly Ser Ser Ser Arg Thr Pro Ser Asp Lys Pro<br>355 360 365 | 1104 |
| gtt gct cac gtt gtt gca aac ccg cag gct gaa ggt caa ctg caa tgg<br>Val Ala His Val Val Ala Asn Pro Gln Ala Glu Gly Gln Leu Gln Trp<br>370 375 380 | 1152 |
| ctg aac cgt cgt gct aac gct ctg ctg gct aac ggt gtt gaa ctg cgt<br>Leu Asn Arg Arg Ala Asn Ala Leu Leu Ala Asn Gly Val Glu Leu Arg<br>385 390 395 400 | 1200 |
| gac aac cag ctg gtt gtt ccg tct gaa ggc ctg tac ctg atc tac tcc<br>Asp Asn Gln Leu Val Val Pro Ser Glu Gly Leu Tyr Leu Ile Tyr Ser<br>405 410 415 | 1248 |
| cag gtt ctg ttc aaa ggc cag ggc tgc ccg tcc acc cac gtt ctg ctg<br>Gln Val Leu Phe Lys Gly Gln Gly Cys Pro Ser Thr His Val Leu Leu<br>420 425 430 | 1296 |
| acc cac acc atc tct cgt atc gct gtt tcc tac cag acc aaa gta aac<br>Thr His Thr Ile Ser Arg Ile Ala Val Ser Tyr Gln Thr Lys Val Asn<br>435 440 445 | 1344 |
| ctg ctg tct gca atc aaa tct ccg tgc cag cgt gaa acc ccg gaa ggt<br>Leu Leu Ser Ala Ile Lys Ser Pro Cys Gln Arg Glu Thr Pro Glu Gly<br>450 455 460 | 1392 |
| gct gaa gct aaa ccg tgg tac gaa ccg atc tac ctg ggt ggc gtt ttt<br>Ala Glu Ala Lys Pro Trp Tyr Glu Pro Ile Tyr Leu Gly Gly Val Phe<br>465 470 475 480 | 1440 |

```
caa ctg gag aaa ggt gac cgt ctg tct gca gaa att aac cgt ccg gac    1488
Gln Leu Glu Lys Gly Asp Arg Leu Ser Ala Glu Ile Asn Arg Pro Asp
            485                 490                 495 tac ctg gac ttc gca gaa tct ggt cag gtt tac ttc ggt atc atc gct    1536
Tyr Leu Asp Phe Ala Glu Ser Gly Gln Val Tyr Phe Gly Ile Ile Ala
            500                 505                 510 ctg tga                                                             1542
Leu
```

<210> SEQ ID NO 28
<211> LENGTH: 513
<212> TYPE: PRT
<213> ORGANISM: Artificial Sequence
<220> FEATURE:
<223> OTHER INFORMATION: Description of Artificial Sequence: cys-scTNF-L short peptide

<400> SEQUENCE: 28

```
Met Gly Glu Leu Ile Glu Gly Arg Cys Ala Gly Gly Ser Gly His His
1               5                   10                  15

His His His His Gly Ser Asp Gly Ala Ser Ser Ser Arg Thr Pro
            20                  25                  30

Ser Asp Lys Pro Val Ala His Val Val Ala Asn Pro Gln Ala Gl

-continued

```
Tyr Glu Pro Ile Tyr Leu Gly Gly Val Phe Gln Leu Glu Lys Gly Asp
305                 310                 315                 320

Arg Leu Ser Ala Glu Ile Asn Arg Pro Asp Tyr Leu Asp Phe Ala Glu
            325                 330                 335

Ser Gly Gln Val Tyr Phe Gly Ile Ile Ala Leu Gly Gly Gly Ser Gly
        340                 345                 350

Gly Gly Ser Gly Gly Gly Ser Ser Arg Thr Pro Ser Asp Lys Pro
    355                 360                 365

Val Ala His Val Val Ala Asn Pro Gln Ala Glu Gly Gln Leu Gln Trp
370                 375                 380

Leu Asn Arg Arg Ala Asn Ala Leu Leu Ala Asn Gly Val Glu Leu Arg
385                 390                 395                 400

Asp Asn Gln Leu Val Val Pro Ser Glu Gly Leu Tyr Leu Ile Tyr Ser
                405                 410                 415

Gln Val Leu Phe Lys Gly Gln Gly Cys Pro Ser Thr His Val Leu Leu
            420                 425                 430

Thr His Thr Ile Ser Arg Ile Ala Val Ser Tyr Gln Thr Lys Val Asn
        435                 440                 445

Leu Leu Ser Ala Ile Lys Ser Pro Cys Gln Arg Glu Thr Pro Glu Gly
    450                 455                 460

Ala Glu Ala Lys Pro Trp Tyr Glu Pro Ile Tyr Leu Gly Gly Val Phe
465                 470                 475                 480

Gln Leu Glu Lys Gly Asp Arg Leu Ser Ala Glu Ile Asn Arg Pro Asp
                485                 490                 495

Tyr Leu Asp Phe Ala Glu Ser Gly Gln Val Tyr Phe Gly Ile Ile Ala
            500                 505                 510

Leu
```

<210> SEQ ID NO 29
<211> LENGTH: 1476
<212> TYPE: DNA
<213> ORGANISM: Artificial Sequence
<220> FEATURE:
<223> OTHER INFORMATION: Description of Artificial Sequence: scFasL
     sequence
<220> FEATURE:
<221> NAME/KEY: CDS
<222> LOCATION: (1)..(1473)

<400> SEQUENCE: 29

```
atg gct atc atc tac ctc atc ctc ctg ttc acc gct gtg cgg ggc gcg      48
Met Ala Ile Ile Tyr Leu Ile Leu Leu Phe Thr Ala Val Arg Gly Ala
1               5                   10                  15 gcc gcg gat tac aaa gac gat gac gat aaa gaa ttc acg cgt gaa aaa      96
Ala Ala Asp Tyr Lys Asp Asp Asp Asp Lys Glu Phe Thr Arg Glu Lys
            20                  25                  30 aag gag ctg agg aaa gtg gcc cat tta aca ggc aag tcc aac tca agg     144
Lys Glu Leu Arg Lys Val Ala His Leu Thr Gly Lys Ser Asn Ser Arg
        35                  40                  45 tcc atg cct ctg gaa tgg gaa gac acc tat gga att gtc ctg ctt tct     192
Ser Met Pro Leu Glu Trp Glu Asp Thr Tyr Gly Ile Val Leu Leu Ser
    50                  55                  60 gga gtg aag tat aag aag ggt ggc ctt gtg atc aat gaa act ggg ctg     240
Gly Val Lys Tyr Lys Lys Gly Gly Leu Val Ile Asn Glu Thr Gly Leu
65                  70                  75                  80 tac ttt gta tat tcc aaa gta tac ttc cgg ggt caa tct tgc aac aac     288
Tyr Phe Val Tyr Ser Lys Val Tyr Phe Arg Gly Gln Ser Cys Asn Asn
                85                  90                  95
```

-continued

| | | |
|---|---|---|
| ctg ccc ctg agc cac aag gtc tac atg agg aac tct aag tat ccc cag<br>Leu Pro Leu Ser His Lys Val Tyr Met Arg Asn Ser Lys Tyr Pro Gln<br>          100                        105                        110 | 336 |
| gat ctg gtg atg atg gag ggg aag atg atg agc tac tgc act act ggg<br>Asp Leu Val Met Met Glu Gly Lys Met Met Ser Tyr Cys Thr Thr Gly<br>          115                        120                        125 | 384 |
| cag atg tgg gcc cgc agc agc tac ctg ggg gca gtg ttc aat ctt acc<br>Gln Met Trp Ala Arg Ser Ser Tyr Leu Gly Ala Val Phe Asn Leu Thr<br>130                        135                        140 | 432 |
| agt gct gat cat tta tat gtc aac gta tct gag ctc tct ctg gtc aat<br>Ser Ala Asp His Leu Tyr Val Asn Val Ser Glu Leu Ser Leu Val Asn<br>145                        150                        155                        160 | 480 |
| ttt gag gaa tct cag acg ttt ttc ggc tta tat aag ctc ggt ggc ggt<br>Phe Glu Glu Ser Gln Thr Phe Phe Gly Leu Tyr Lys Leu Gly Gly Gly<br>                        165                        170                        175 | 528 |
| tct ggt ggc ggt tct ggt ggc ggt tct ggt ggc gga tca gaa aaa aag<br>Ser Gly Gly Gly Ser Gly Gly Gly Ser Gly Gly Gly Ser Glu Lys Lys<br>                        180                        185                        190 | 576 |
| gag ctg agg aaa gtg gcc cat tta aca ggc aag tcc aac tca agg tcc<br>Glu Leu Arg Lys Val Ala His Leu Thr Gly Lys Ser Asn Ser Arg Ser<br>        195                        200                        205 | 624 |
| atg cct ctg gaa tgg gaa gac acc tat gga att gtc ctg ctt tct gga<br>Met Pro Leu Glu Trp Glu Asp Thr Tyr Gly Ile Val Leu Leu Ser Gly<br>210                        215                        220 | 672 |
| gtg aag tat aag aag ggt ggc ctt gtg atc aat gaa act ggg ctg tac<br>Val Lys Tyr Lys Lys Gly Gly Leu Val Ile Asn Glu Thr Gly Leu Tyr<br>225                        230                        235                        240 | 720 |
| ttt gta tat tcc aaa gta tac ttc cgg ggt caa tct tgc aac aac ctg<br>Phe Val Tyr Ser Lys Val Tyr Phe Arg Gly Gln Ser Cys Asn Asn Leu<br>                        245                        250                        255 | 768 |
| ccc ctg agc cac aag gtc tac atg agg aac tct aag tat ccc cag gat<br>Pro Leu Ser His Lys Val Tyr Met Arg Asn Ser Lys Tyr Pro Gln Asp<br>        260                        265                        270 | 816 |
| ctg gtg atg atg gag ggg aag atg atg agc tac tgc act act ggg cag<br>Leu Val Met Met Glu Gly Lys Met Met Ser Tyr Cys Thr Thr Gly Gln<br>          275                        280                        285 | 864 |
| atg tgg gcc cgc agc agc tac ctg ggg gca gtg ttc aat ctt acc agt<br>Met Trp Ala Arg Ser Ser Tyr Leu Gly Ala Val Phe Asn Leu Thr Ser<br>290                        295                        300 | 912 |
| gct gat cat tta tat gtc aac gta tct gag ctc tct ctg gtc aat ttt<br>Ala Asp His Leu Tyr Val Asn Val Ser Glu Leu Ser Leu Val Asn Phe<br>305                        310                        315                        320 | 960 |
| gag gaa tct cag acg ttt ttc ggc tta tat aag ctc ggt ggc ggt tct<br>Glu Glu Ser Gln Thr Phe Phe Gly Leu Tyr Lys Leu Gly Gly Gly Ser<br>                        325                        330                        335 | 1008 |
| ggt ggc ggt tct ggt ggc ggt tct ggt ggc gga tcc gaa aaa aag gag<br>Gly Gly Gly Ser Gly Gly Gly Ser Gly Gly Gly Ser Glu Lys Lys Glu<br>                        340                        345                        350 | 1056 |
| ctg agg aaa gtg gcc cat tta aca ggc aag tcc aac tca agg tcc atg<br>Leu Arg Lys Val Ala His Leu Thr Gly Lys Ser Asn Ser Arg Ser Met<br>        355                        360                        365 | 1104 |
| cct ctg gaa tgg gaa gac acc tat gga att gtc ctg ctt tct gga gtg<br>Pro Leu Glu Trp Glu Asp Thr Tyr Gly Ile Val Leu Leu Ser Gly Val<br>370                        375                        380 | 1152 |
| aag tat aag aag ggt ggc ctt gtg atc aat gaa act ggg ctg tac ttt<br>Lys Tyr Lys Lys Gly Gly Leu Val Ile Asn Glu Thr Gly Leu Tyr Phe<br>385                        390                        395                        400 | 1200 |
| gta tat tcc aaa gta tac ttc cgg ggt caa tct tgc aac aac ctg ccc<br>Val Tyr Ser Lys Val Tyr Phe Arg Gly Gln Ser Cys Asn Asn Leu Pro | 1248 |

|  |  |  |  |  | 405 |  |  |  |  | 410 |  |  |  |  | 415 |  |  |
|---|---|---|---|---|---|---|---|---|---|---|---|---|---|---|---|---|---|

```
ctg agc cac aag gtc tac atg agg aac tct aag tat ccc cag gat ctg     1296
Leu Ser His Lys Val Tyr Met Arg Asn Ser Lys Tyr Pro Gln Asp Leu
        420                 425                 430 gtg atg atg gag ggg aag atg atg agc tac tgc act act ggg cag atg     1344
Val Met Met Glu Gly Lys Met Met Ser Tyr Cys Thr Thr Gly Gln Met
            435                 440                 445 tgg gcc cgc agc agc tac ctg ggg gca gtg ttc aat ctt acc agt gct     1392
Trp Ala Arg Ser Ser Tyr Leu Gly Ala Val Phe Asn Leu Thr Ser Ala
    450                 455                 460 gat cat tta tat gtc aac gta tct gag ctc tct ctg gtc aat ttt gag     1440
Asp His Leu Tyr Val Asn Val Ser Glu Leu Ser Leu Val Asn Phe Glu
465                 470                 475                 480 gaa tct cag acg ttt ttc ggc tta tat aag ctc tga                     1476
Glu Ser Gln Thr Phe Phe Gly Leu Tyr Lys Leu
                485                 490
```

<210> SEQ ID NO 30
<211> LENGTH: 491
<212> TYPE: PRT
<213> ORGANISM: Artificial Sequence
<220> FEATURE:
<223> OTHER INFORMATION: Description of Artificial Sequence: scFasL
       peptide sequence

<400> SEQUENCE: 30

```
Met Ala Ile Ile Tyr Leu Ile Leu Leu Phe Thr Ala Val Arg Gly Ala
1               5                   10                  15

Ala Ala Asp Tyr Lys Asp Asp Asp Lys Glu Phe Thr Arg Glu Lys
            20                  25                  30

Lys Glu Leu Arg Lys Val Ala His Leu Thr Gly Lys Ser Asn Ser Arg
        35                  40                  45

Ser Met Pro Leu Glu Trp Glu Asp Thr Tyr Gly Ile Val Leu Leu Ser
    50                  55                  60

Gly Val Lys Tyr Lys Lys Gly Gly Leu Val Ile Asn Glu Thr Gly Leu
65                  70                  75                  80

Tyr Phe Val Tyr Ser Lys Val Tyr Phe Arg Gly Gln Ser Cys Asn Asn
                85                  90                  95

Leu Pro Leu Ser His Lys Val Tyr Met Arg Asn Ser Lys Tyr Pro Gln
            100                 105                 110

Asp Leu Val Met Met Glu Gly Lys Met Met Ser Tyr Cys Thr Thr Gly
        115                 120                 125

Gln Met Trp Ala Arg Ser Ser Tyr Leu Gly Ala Val Phe Asn Leu Thr
    130                 135                 140

Ser Ala Asp His Leu Tyr Val Asn Val Ser Glu Leu Ser Leu Val Asn
145                 150                 155                 160

Phe Glu Glu Ser Gln Thr Phe Phe Gly Leu Tyr Lys Leu Gly Gly Gly
                165                 170                 175

Ser Gly Gly Gly Ser Gly Gly Gly Ser Gly Gly Gly Ser Glu Lys Lys
            180                 185                 190

Glu Leu Arg Lys Val Ala His Leu Thr Gly Lys Ser Asn Ser Arg Ser
        195                 200                 205

Met Pro Leu Glu Trp Glu Asp Thr Tyr Gly Ile Val Leu Leu Ser Gly
    210                 215                 220

Val Lys Tyr Lys Lys Gly Gly Leu Val Ile Asn Glu Thr Gly Leu Tyr
225                 230                 235                 240

Phe Val Tyr Ser Lys Val Tyr Phe Arg Gly Gln Ser Cys Asn Asn Leu
```

-continued

```
                    245                 250                 255
Pro Leu Ser His Lys Val Tyr Met Arg Asn Ser Lys Tyr Pro Gln Asp
            260                 265                 270
Leu Val Met Met Glu Gly Lys Met Met Ser Tyr Cys Thr Thr Gly Gln
        275                 280                 285
Met Trp Ala Arg Ser Ser Tyr Leu Gly Ala Val Phe Asn Leu Thr Ser
    290                 295                 300
Ala Asp His Leu Tyr Val Asn Val Ser Glu Leu Ser Leu Val Asn Phe
305                 310                 315                 320
Glu Glu Ser Gln Thr Phe Phe Gly Leu Tyr Lys Leu Gly Gly Gly Ser
                325                 330                 335
Gly Gly Gly Ser Gly Gly Ser Gly Gly Ser Glu Lys Lys Glu
            340                 345                 350
Leu Arg Lys Val Ala His Leu Thr Gly Lys Ser Asn Ser Arg Ser Met
        355                 360                 365
Pro Leu Glu Trp Glu Asp Thr Tyr Gly Ile Val Leu Leu Ser Gly Val
    370                 375                 380
Lys Tyr Lys Lys Gly Gly Leu Val Ile Asn Glu Thr Gly Leu Tyr Phe
385                 390                 395                 400
Val Tyr Ser Lys Val Tyr Phe Arg Gly Gln Ser Cys Asn Asn Leu Pro
                405                 410                 415
Leu Ser His Lys Val Tyr Met Arg Asn Ser Lys Tyr Pro Gln Asp Leu
            420                 425                 430
Val Met Met Glu Gly Lys Met Met Ser Tyr Cys Thr Thr Gly Gln Met
        435                 440                 445
Trp Ala Arg Ser Ser Tyr Leu Gly Ala Val Phe Asn Leu Thr Ser Ala
    450                 455                 460
Asp His Leu Tyr Val Asn Val Ser Glu Leu Ser Leu Val Asn Phe Glu
465                 470                 475                 480
Glu Ser Gln Thr Phe Phe Gly Leu Tyr Lys Leu
                485                 490
```

<210> SEQ ID NO 31
<211> LENGTH: 1869
<212> TYPE: DNA
<213> ORGANISM: Artificial Sequence
<220> FEATURE:
<223> OTHER INFORMATION: Description of Artificial Sequence: scTRAIL
      sequence
<220> FEATURE:
<221> NAME/KEY: CDS
<222> LOCATION: (1)..(1866)

<400> SEQUENCE: 31

```
atg gct atc atc tac ctc atc ctc ctg ttc acc gct gtg cgg ggc gcg     48
Met Ala Ile Ile Tyr Leu Ile Leu Leu Phe Thr Ala Val Arg Gly Ala
1               5                   10                  15 gcc gcg gat tac aaa gac gat gac gat aaa gaa ttc gga acc tct gag     96
Ala Ala Asp Tyr Lys Asp Asp Asp Asp Lys Glu Phe Gly Thr Ser Glu
                20                  25                  30 gaa acc att tct aca gtt caa gaa aag caa caa aat att tct ccc cta    144
Glu Thr Ile Ser Thr Val Gln Glu Lys Gln Gln Asn Ile Ser Pro Leu
            35                  40                  45 gtg aga gaa aga ggt cct cag aga gta gca gct cac ata act ggg acc    192
Val Arg Glu Arg Gly Pro Gln Arg Val Ala Ala His Ile Thr Gly Thr
        50                  55                  60 aga gga aga agc aac aca ttg tct tct cca aac tcc aag aat gaa aag    240
Arg Gly Arg Ser Asn Thr Leu Ser Ser Pro Asn Ser Lys Asn Glu Lys
```

```
                    65                  70                  75                  80
gct ctg ggc cgc aaa ata aac tcc tgg gaa tca tca agg agt ggg cat        288
Ala Leu Gly Arg Lys Ile Asn Ser Trp Glu Ser Ser Arg Ser Gly His
                85                  90                  95 tca ttc ctg agc aac ttg cac ttg agg aat ggt gaa ctg gtc atc cat        336
Ser Phe Leu Ser Asn Leu His Leu Arg Asn Gly Glu Leu Val Ile His
                100                 105                 110 gaa aaa ggg ttt tac tac atc tat tcc caa aca tac ttt cga ttt cag        384
Glu Lys Gly Phe Tyr Tyr Ile Tyr Ser Gln Thr Tyr Phe Arg Phe Gln
            115                 120                 125 gag gaa ata aaa gaa aac aca aag aac gac aaa caa atg gtc caa tat        432
Glu Glu Ile Lys Glu Asn Thr Lys Asn Asp Lys Gln Met Val Gln Tyr
        130                 135                 140 att tac aaa tac aca agt tat cct gac cct ata ttg ttg atg aaa agt        480
Ile Tyr Lys Tyr Thr Ser Tyr Pro Asp Pro Ile Leu Leu Met Lys Ser
145                 150                 155                 160 gct aga aat agt tgt tgg tct aaa gat gca gaa tat gga ctc tat tcc        528
Ala Arg Asn Ser Cys Trp Ser Lys Asp Ala Glu Tyr Gly Leu Tyr Ser
                165                 170                 175 atc tat caa ggg gga ata ttt gag ctt aag gaa aat gac aga att ttt        576
Ile Tyr Gln Gly Gly Ile Phe Glu Leu Lys Glu Asn Asp Arg Ile Phe
            180                 185                 190 gtt tct gta aca aat gag cac ttg ata gac atg gac cat gaa gcc agt        624
Val Ser Val Thr Asn Glu His Leu Ile Asp Met Asp His Glu Ala Ser
        195                 200                 205 ttt ttc ggg gcc ttt tta gtt ggc ggt ggc ggt tct ggt ggc ggt tct        672
Phe Phe Gly Ala Phe Leu Val Gly Gly Gly Gly Ser Gly Gly Gly Ser
210                 215                 220 ggt ggc ggt tct ggt ggc gga tca acc tct gag gaa acc att tct aca        720
Gly Gly Gly Ser Gly Gly Gly Ser Thr Ser Glu Glu Thr Ile Ser Thr
225                 230                 235                 240 gtt caa gaa aag caa caa aat att tct ccc cta gtg aga gaa aga ggt        768
Val Gln Glu Lys Gln Gln Asn Ile Ser Pro Leu Val Arg Glu Arg Gly
                245                 250                 255 cct cag aga gta gca gct cac ata act ggg acc aga gga aga agc aac        816
Pro Gln Arg Val Ala Ala His Ile Thr Gly Thr Arg Gly Arg Ser Asn
            260                 265                 270 aca ttg tct tct cca aac tcc aag aat gaa aag gct ctg ggc cgc aaa        864
Thr Leu Ser Ser Pro Asn Ser Lys Asn Glu Lys Ala Leu Gly Arg Lys
        275                 280                 285 ata aac tcc tgg gaa tca tca agg agt ggg cat tca ttc ctg agc aac        912
Ile Asn Ser Trp Glu Ser Ser Arg Ser Gly His Ser Phe Leu Ser Asn
        290                 295                 300 ttg cac ttg agg aat ggt gaa ctg gtc atc cat gaa aaa ggg ttt tac        960
Leu His Leu Arg Asn Gly Glu Leu Val Ile His Glu Lys Gly Phe Tyr
305                 310                 315                 320 tac atc tat tcc caa aca tac ttt cga ttt cag gag gaa ata aaa gaa        1008
Tyr Ile Tyr Ser Gln Thr Tyr Phe Arg Phe Gln Glu Glu Ile Lys Glu
                325                 330                 335 aac aca aag aac gac aaa caa atg gtc caa tat att tac aaa tac aca        1056
Asn Thr Lys Asn Asp Lys Gln Met Val Gln Tyr Ile Tyr Lys Tyr Thr
            340                 345                 350 agt tat cct gac cct ata ttg ttg atg aaa agt gct aga aat agt tgt        1104
Ser Tyr Pro Asp Pro Ile Leu Leu Met Lys Ser Ala Arg Asn Ser Cys
        355                 360                 365 tgg tct aaa gat gca gaa tat gga ctc tat tcc atc tat caa ggg gga        1152
Trp Ser Lys Asp Ala Glu Tyr Gly Leu Tyr Ser Ile Tyr Gln Gly Gly
        370                 375                 380 ata ttt gag ctt aag gaa aat gac aga att ttt gtt tct gta aca aat        1200
```

```
                Ile Phe Glu Leu Lys Glu Asn Asp Arg Ile Phe Val Ser Val Thr Asn
                385                 390                 395                 400 gag cac ttg ata gac atg gac cat gaa gcc agt ttt ttc ggg gcc ttt      1248
Glu His Leu Ile Asp Met Asp His Glu Ala Ser Phe Phe Gly Ala Phe
                405                 410                 415 tta gtt ggc ggt ggc ggt tct ggt ggc ggt tct ggt ggc ggt tct ggt      1296
Leu Val Gly Gly Gly Gly Ser Gly Gly Gly Ser Gly Gly Gly Ser Gly
                420                 425                 430 ggc gga tcc acc tct gag gaa acc att tct aca gtt caa gaa aag caa      1344
Gly Gly Ser Thr Ser Glu Glu Thr Ile Ser Thr Val Gln Glu Lys Gln
                435                 440                 445 caa aat att tct ccc cta gtg aga gaa aga ggt cct cag aga gta gca      1392
Gln Asn Ile Ser Pro Leu Val Arg Glu Arg Gly Pro Gln Arg Val Ala
450                 455                 460 gct cac ata act ggg acc aga gga aga agc aac aca ttg tct tct cca      1440
Ala His Ile Thr Gly Thr Arg Gly Arg Ser Asn Thr Leu Ser Ser Pro
465                 470                 475                 480 aac tcc aag aat gaa aag gct ctg ggc cgc aaa ata aac tcc tgg gaa      1488
Asn Ser Lys Asn Glu Lys Ala Leu Gly Arg Lys Ile Asn Ser Trp Glu
                485                 490                 495 tca tca agg agt ggg cat tca ttc ctg agc aac ttg cac ttg agg aat      1536
Ser Ser Arg Ser Gly His Ser Phe Leu Ser Asn Leu His Leu Arg Asn
                500                 505                 510 ggt gaa ctg gtc atc cat gaa aaa ggg ttt tac tac atc tat tcc caa      1584
Gly Glu Leu Val Ile His Glu Lys Gly Phe Tyr Tyr Ile Tyr Ser Gln
                515                 520                 525 aca tac ttt cga ttt cag gag gaa ata aaa gaa aac aca aag aac gac      1632
Thr Tyr Phe Arg Phe Gln Glu Glu Ile Lys Glu Asn Thr Lys Asn Asp
                530                 535                 540 aaa caa atg gtc caa tat att tac aaa tac aca agt tat cct gac cct      1680
Lys Gln Met Val Gln Tyr Ile Tyr Lys Tyr Thr Ser Tyr Pro Asp Pro
545                 550                 555                 560 ata ttg ttg atg aaa agt gct aga aat agt tgt tgg tct aaa gat gca      1728
Ile Leu Leu Met Lys Ser Ala Arg Asn Ser Cys Trp Ser Lys Asp Ala
                565                 570                 575 gaa tat gga ctc tat tcc atc tat caa ggg gga ata ttt gag ctt aag      1776
Glu Tyr Gly Leu Tyr Ser Ile Tyr Gln Gly Gly Ile Phe Glu Leu Lys
                580                 585                 590 gaa aat gac aga att ttt gtt tct gta aca aat gag cac ttg ata gac      1824
Glu Asn Asp Arg Ile Phe Val Ser Val Thr Asn Glu His Leu Ile Asp
                595                 600                 605 atg gac cat gaa gcc agt ttt ttc ggg gcc ttt tta gtt ggc tga          1869
Met Asp His Glu Ala Ser Phe Phe Gly Ala Phe Leu Val Gly
                610                 615                 620

<210> SEQ ID NO 32
<211> LENGTH: 622
<212> TYPE: PRT
<213> ORGANISM: Artificial Sequence
<220> FEATURE:
<223> OTHER INFORMATION: Description of Artificial Sequence: scTRAIL
      peptide sequence

<400> SEQUENCE: 32

Met Ala Ile Ile Tyr Leu Ile Leu Leu Phe Thr Ala Val Arg Gly Ala
1               5                   10                  15

Ala Ala Asp Tyr Lys Asp Asp Asp Lys Glu Phe Gly Thr Ser Glu
                20                  25                  30

Glu Thr Ile Ser Thr Val Gln Glu Lys Gln Gln Asn Ile Ser Pro Leu
                35                  40                  45
```

Val Arg Glu Arg Gly Pro Gln Arg Val Ala Ala His Ile Thr Gly Thr
 50                  55                  60

Arg Gly Arg Ser Asn Thr Leu Ser Ser Pro Asn Ser Lys Asn Glu Lys
 65              70                  75                  80

Ala Leu Gly Arg Lys Ile Asn Ser Trp Glu Ser Ser Arg Ser Gly His
                 85                  90                  95

Ser Phe Leu Ser Asn Leu His Leu Arg Asn Gly Glu Leu Val Ile His
             100                 105                 110

Glu Lys Gly Phe Tyr Tyr Ile Tyr Ser Gln Thr Tyr Phe Arg Phe Gln
         115                 120                 125

Glu Glu Ile Lys Glu Asn Thr Lys Asn Asp Lys Gln Met Val Gln Tyr
130                 135                 140

Ile Tyr Lys Tyr Thr Ser Tyr Pro Asp Pro Ile Leu Leu Met Lys Ser
145                 150                 155                 160

Ala Arg Asn Ser Cys Trp Ser Lys Asp Ala Glu Tyr Gly Leu Tyr Ser
                165                 170                 175

Ile Tyr Gln Gly Gly Ile Phe Glu Leu Lys Glu Asn Asp Arg Ile Phe
            180                 185                 190

Val Ser Val Thr Asn Glu His Leu Ile Asp Met Asp His Glu Ala Ser
        195                 200                 205

Phe Phe Gly Ala Phe Leu Val Gly Gly Gly Ser Gly Gly Gly Gly Ser
210                 215                 220

Gly Gly Gly Ser Gly Gly Gly Ser Thr Ser Glu Glu Thr Ile Ser Thr
225                 230                 235                 240

Val Gln Glu Lys Gln Gln Asn Ile Ser Pro Leu Val Arg Glu Arg Gly
                245                 250                 255

Pro Gln Arg Val Ala Ala His Ile Thr Gly Thr Arg Gly Arg Ser Asn
            260                 265                 270

Thr Leu Ser Ser Pro Asn Ser Lys Asn Glu Lys Ala Leu Gly Arg Lys
        275                 280                 285

Ile Asn Ser Trp Glu Ser Ser Arg Ser Gly His Ser Phe Leu Ser Asn
290                 295                 300

Leu His Leu Arg Asn Gly Glu Leu Val Ile His Glu Lys Gly Phe Tyr
305                 310                 315                 320

Tyr Ile Tyr Ser Gln Thr Tyr Phe Arg Phe Gln Glu Glu Ile Lys Glu
                325                 330                 335

Asn Thr Lys Asn Asp Lys Gln Met Val Gln Tyr Ile Tyr Lys Tyr Thr
            340                 345                 350

Ser Tyr Pro Asp Pro Ile Leu Leu Met Lys Ser Ala Arg Asn Ser Cys
        355                 360                 365

Trp Ser Lys Asp Ala Glu Tyr Gly Leu Tyr Ser Ile Tyr Gln Gly Gly
370                 375                 380

Ile Phe Glu Leu Lys Glu Asn Asp Arg Ile Phe Val Ser Val Thr Asn
385                 390                 395                 400

Glu His Leu Ile Asp Met Asp His Glu Ala Ser Phe Phe Gly Ala Phe
                405                 410                 415

Leu Val Gly Gly Gly Ser Gly Gly Gly Ser Gly Gly Gly Ser Gly Gly
            420                 425                 430

Gly Ser Thr Ser Glu Glu Thr Ile Ser Thr Val Gln Glu Lys Gln
        435                 440                 445

Gln Asn Ile Ser Pro Leu Val Arg Glu Arg Gly Pro Gln Arg Val Ala
450                 455                 460

Ala His Ile Thr Gly Thr Arg Gly Arg Ser Asn Thr Leu Ser Ser Pro

```
                465                 470                 475                 480
      Asn Ser Lys Asn Glu Lys Ala Leu Gly Arg Lys Ile Asn Ser Trp Glu
                      485                 490                 495

Ser Ser Arg Ser Gly His Ser Phe Leu Ser Asn Leu His Leu Arg Asn
                      500                 505                 510

Gly Glu Leu Val Ile His Glu Lys Gly Phe Tyr Tyr Ile Tyr Ser Gln
                      515                 520                 525

Thr Tyr Phe Arg Phe Gln Glu Glu Ile Lys Glu Asn Thr Lys Asn Asp
                      530                 535                 540

Lys Gln Met Val Gln Tyr Ile Tyr Lys Tyr Thr Ser Tyr Pro Asp Pro
      545                 550                 555                 560

Ile Leu Leu Met Lys Ser Ala Arg Asn Ser Cys Trp Ser Lys Asp Ala
                      565                 570                 575

Glu Tyr Gly Leu Tyr Ser Ile Tyr Gln Gly Gly Ile Phe Glu Leu Lys
                      580                 585                 590

Glu Asn Asp Arg Ile Phe Val Ser Val Thr Asn Glu His Leu Ile Asp
                      595                 600                 605

Met Asp His Glu Ala Ser Phe Phe Gly Ala Phe Leu Val Gly
                      610                 615                 620

<210> SEQ ID NO 33
<211> LENGTH: 1581
<212> TYPE: DNA
<213> ORGANISM: Artificial Sequence
<220> FEATURE:
<223> OTHER INFORMATION: Description of Artificial Sequence: scTNF
      sequence
<220> FEATURE:
<221> NAME/KEY: CDS
<222> LOCATION: (1)..(1578)

<400> SEQUENCE: 33 atg gct atc atc tac ctc atc ctc ctg ttc acc gct gtg cgg ggc gcg      48
Met Ala Ile Ile Tyr Leu Ile Leu Leu Phe Thr Ala Val Arg Gly Ala
1               5                   10                  15 gcc gcg gat tac aaa gac gat gac gat aaa gaa ttc gga tca tct tct      96
Ala Ala Asp Tyr Lys Asp Asp Asp Asp Lys Glu Phe Gly Ser Ser Ser
                20                  25                  30 cga acc ccg agt gac aag cct gta gcc cat gtt gta gca aac cct caa     144
Arg Thr Pro Ser Asp Lys Pro Val Ala His Val Val Ala Asn Pro Gln
            35                  40                  45 gct gag ggg cag ctc cag tgg ctg aac cgc cgg gcc aat gcc ctc ctg     192
Ala Glu Gly Gln Leu Gln Trp Leu Asn Arg Arg Ala Asn Ala Leu Leu
        50                  55                  60 gcc aat ggc gtg gag ctg aga gat aac cag ctg gtg gtg cca tca gag     240
Ala Asn Gly Val Glu Leu Arg Asp Asn Gln Leu Val Val Pro Ser Glu
65                  70                  75                  80 ggc ctg tac ctc atc tac tcc cag gtc ctc ttc aag ggc caa ggc tgc     288
Gly Leu Tyr Leu Ile Tyr Ser Gln Val Leu Phe Lys Gly Gln Gly Cys
                85                  90                  95 ccc tcc acc cat gtg ctc ctc acc cac acc atc agc cgc atc gcc gtc     336
Pro Ser Thr His Val Leu Leu Thr His Thr Ile Ser Arg Ile Ala Val
                100                 105                 110 tcc tac cag acc aag gtc aac ctc ctc tct gcc atc aag agc ccc tgc     384
Ser Tyr Gln Thr Lys Val Asn Leu Leu Ser Ala Ile Lys Ser Pro Cys
            115                 120                 125 cag agg gag acc cca gag ggg gct gag gcc aag ccc tgg tat gag ccc     432
Gln Arg Glu Thr Pro Glu Gly Ala Glu Ala Lys Pro Trp Tyr Glu Pro
        130                 135                 140
```

-continued

| | | |
|---|---|---|
| atc tat ctg gga ggg gtc ttc cag ctg gag aag ggt gac cga ctc agc<br>Ile Tyr Leu Gly Gly Val Phe Gln Leu Glu Lys Gly Asp Arg Leu Ser<br>145                         150                   155               160 | 480 |
| gct gag atc aat cgg ccc gac tat ctc gac ttt gcc gag tct ggg cag<br>Ala Glu Ile Asn Arg Pro Asp Tyr Leu Asp Phe Ala Glu Ser Gly Gln<br>                     165                 170                 175 | 528 |
| gtc tac ttt ggg atc att gcc ctg ggt ggc ggt tct ggt ggc ggt tct<br>Val Tyr Phe Gly Ile Ile Ala Leu Gly Gly Gly Ser Gly Gly Gly Ser<br>                180                 185                 190 | 576 |
| ggt ggc ggt tct ggt ggc gga tca tca tct tct cga acc ccg agt gac<br>Gly Gly Gly Ser Gly Gly Gly Ser Ser Ser Ser Arg Thr Pro Ser Asp<br>195                         200                   205 | 624 |
| aag cct gta gcc cat gtt gta gca aac cct caa gct gag ggg cag ctc<br>Lys Pro Val Ala His Val Val Ala Asn Pro Gln Ala Glu Gly Gln Leu<br>210                         215                   220 | 672 |
| cag tgg ctg aac cgc cgg gcc aat gcc ctc ctg gcc aat ggc gtg gag<br>Gln Trp Leu Asn Arg Arg Ala Asn Ala Leu Leu Ala Asn Gly Val Glu<br>225                         230                   235               240 | 720 |
| ctg aga gat aac cag ctg gtg gtg cca tca gag ggc ctg tac ctc atc<br>Leu Arg Asp Asn Gln Leu Val Val Pro Ser Glu Gly Leu Tyr Leu Ile<br>                     245                 250                 255 | 768 |
| tac tcc cag gtc ctc ttc aag ggc caa ggc tgc ccc tcc acc cat gtg<br>Tyr Ser Gln Val Leu Phe Lys Gly Gln Gly Cys Pro Ser Thr His Val<br>                260                 265                 270 | 816 |
| ctc ctc acc cac acc atc agc cgc atc gcc gtc tcc tac cag acc aag<br>Leu Leu Thr His Thr Ile Ser Arg Ile Ala Val Ser Tyr Gln Thr Lys<br>                     275                 280                 285 | 864 |
| gtc aac ctc ctc tct gcc atc aag agc ccc tgc cag agg gag acc cca<br>Val Asn Leu Leu Ser Ala Ile Lys Ser Pro Cys Gln Arg Glu Thr Pro<br>290                         295                   300 | 912 |
| gag ggg gct gag gcc aag ccc tgg tat gag ccc atc tat ctg gga ggg<br>Glu Gly Ala Glu Ala Lys Pro Trp Tyr Glu Pro Ile Tyr Leu Gly Gly<br>305                         310                   315               320 | 960 |
| gtc ttc cag ctg gag aag ggt gac cga ctc agc gct gag atc aat cgg<br>Val Phe Gln Leu Glu Lys Gly Asp Arg Leu Ser Ala Glu Ile Asn Arg<br>                     325                 330                 335 | 1008 |
| ccc gac tat ctc gac ttt gcc gag tct ggg cag gtc tac ttt ggg atc<br>Pro Asp Tyr Leu Asp Phe Ala Glu Ser Gly Gln Val Tyr Phe Gly Ile<br>                   340                 345                 350 | 1056 |
| att gcc ctg ggt ggc ggt tct ggt ggc ggt tct ggt ggc ggt tct ggt<br>Ile Ala Leu Gly Gly Gly Ser Gly Gly Gly Ser Gly Gly Gly Ser Gly<br>                     355                 360                 365 | 1104 |
| ggc gga tca tca tct tct cga acc ccg agt gac aag cct gta gcc cat<br>Gly Gly Ser Ser Ser Ser Arg Thr Pro Ser Asp Lys Pro Val Ala His<br>370                         375                   380 | 1152 |
| gtt gta gca aac cct caa gct gag ggg cag ctc cag tgg ctg aac cgc<br>Val Val Ala Asn Pro Gln Ala Glu Gly Gln Leu Gln Trp Leu Asn Arg<br>385                         390                   395               400 | 1200 |
| cgg gcc aat gcc ctc ctg gcc aat ggc gtg gag ctg aga gat aac cag<br>Arg Ala Asn Ala Leu Leu Ala Asn Gly Val Glu Leu Arg Asp Asn Gln<br>                     405                 410                 415 | 1248 |
| ctg gtg gtg cca tca gag ggc ctg tac ctc atc tac tcc cag gtc ctc<br>Leu Val Val Pro Ser Glu Gly Leu Tyr Leu Ile Tyr Ser Gln Val Leu<br>                     420                 425                 430 | 1296 |
| ttc aag ggc caa ggc tgc ccc tcc acc cat gtg ctc ctc acc cac acc<br>Phe Lys Gly Gln Gly Cys Pro Ser Thr His Val Leu Leu Thr His Thr<br>                     435                 440                 445 | 1344 |
| atc agc cgc atc gcc gtc tcc tac cag acc aag gtc aac ctc ctc tct<br>Ile Ser Arg Ile Ala Val Ser Tyr Gln Thr Lys Val Asn Leu Leu Ser<br>450                         455                   460 | 1392 |

```
gcc atc aag agc ccc tgc cag agg gag acc cca gag ggg gct gag gcc    1440
Ala Ile Lys Ser Pro Cys Gln Arg Glu Thr Pro Glu Gly Ala Glu Ala
465                 470                 475                 480 aag ccc tgg tat gag ccc atc tat ctg gga ggg gtc ttc cag ctg gag    1488
Lys Pro Trp Tyr Glu Pro Ile Tyr Leu Gly Gly Val Phe Gln Leu Glu
                485                 490                 495 aag ggt gac cga ctc agc gct gag atc aat cgg ccc gac tat ctc gac    1536
Lys Gly Asp Arg Leu Ser Ala Glu Ile Asn Arg Pro Asp Tyr Leu Asp
            500                 505                 510 ttt gcc gag tct ggg cag gtc tac ttt ggg atc att gcc ctg tga        1581
Phe Ala Glu Ser Gly Gln Val Tyr Phe Gly Ile Ile Ala Leu
                515                 520                 525

<210> SEQ ID NO 34
<211> LENGTH: 526
<212> TYPE: PRT
<213> ORGANISM: Artificial Sequence
<220> FEATURE:
<223> OTHER INFORMATION: Description of Artificial Sequence: scTNF
      peptide sequence

<400> SEQUENCE: 34

Met Ala Ile Ile Tyr Leu Ile Leu Leu Phe Thr Ala Val Arg Gly Ala
1               5                   10                  15

Ala Ala Asp Tyr Lys Asp Asp Asp Lys Glu Phe Gly Ser Ser Ser
            20                  25                  30

Arg Thr Pro Ser Asp Lys Pro Val Ala His Val Val Ala Asn Pro Gln
        35                  40                  45

Ala Glu Gly Gln Leu Gln Trp Leu Asn Arg Arg Ala Asn Ala Leu Leu
    50                  55                  60

Ala Asn Gly Val Glu Leu Arg Asp Asn Gln Leu Val Val Pro Ser Glu
65                  70                  75                  80

Gly Leu Tyr Leu Ile Tyr Ser Gln Val Leu Phe Lys Gly Gln Gly Cys
                85                  90                  95

Pro Ser Thr His Val Leu Leu Thr His Thr Ile Ser Arg Ile Ala Val
            100                 105                 110

Ser Tyr Gln Thr Lys Val Asn Leu Leu Ser Ala Ile Lys Ser Pro Cys
        115                 120                 125

Gln Arg Glu Thr Pro Glu Gly Ala Glu Ala Lys Pro Trp Tyr Glu Pro
    130                 135                 140

Ile Tyr Leu Gly Gly Val Phe Gln Leu Glu Lys Gly Asp Arg Leu Ser
145                 150                 155                 160

Ala Glu Ile Asn Arg Pro Asp Tyr Leu Asp Phe Ala Glu Ser Gly Gln
                165                 170                 175

Val Tyr Phe Gly Ile Ile Ala Leu Gly Gly Gly Ser Gly Gly Gly Ser
            180                 185                 190

Gly Gly Gly Ser Gly Gly Gly Ser Ser Ser Arg Thr Pro Ser Asp
        195                 200                 205

Lys Pro Val Ala His Val Val Ala Asn Pro Gln Ala Glu Gly Gln Leu
    210                 215                 220

Gln Trp Leu Asn Arg Arg Ala Asn Ala Leu Leu Ala Asn Gly Val Glu
225                 230                 235                 240

Leu Arg Asp Asn Gln Leu Val Val Pro Ser Glu Gly Leu Tyr Leu Ile
                245                 250                 255

Tyr Ser Gln Val Leu Phe Lys Gly Gln Gly Cys Pro Ser Thr His Val
            260                 265                 270
```

```
Leu Leu Thr His Thr Ile Ser Arg Ile Ala Val Ser Tyr Gln Thr Lys
            275                 280                 285

Val Asn Leu Leu Ser Ala Ile Lys Ser Pro Cys Gln Arg Glu Thr Pro
        290                 295                 300

Glu Gly Ala Glu Ala Lys Pro Trp Tyr Glu Pro Ile Tyr Leu Gly Gly
305                 310                 315                 320

Val Phe Gln Leu Glu Lys Gly Asp Arg Leu Ser Ala Glu Ile Asn Arg
                325                 330                 335

Pro Asp Tyr Leu Asp Phe Ala Glu Ser Gly Gln Val Tyr Phe Gly Ile
            340                 345                 350

Ile Ala Leu Gly Gly Gly Ser Gly Gly Gly Ser Gly Gly Gly Ser Gly
        355                 360                 365

Gly Gly Ser Ser Ser Arg Thr Pro Ser Asp Lys Pro Val Ala His
370                 375                 380

Val Val Ala Asn Pro Gln Ala Glu Gly Gln Leu Gln Trp Leu Asn Arg
385                 390                 395                 400

Arg Ala Asn Ala Leu Leu Ala Asn Gly Val Glu Leu Arg Asp Asn Gln
                405                 410                 415

Leu Val Val Pro Ser Glu Gly Leu Tyr Leu Ile Tyr Ser Gln Val Leu
            420                 425                 430

Phe Lys Gly Gln Gly Cys Pro Ser Thr His Val Leu Leu Thr His Thr
        435                 440                 445

Ile Ser Arg Ile Ala Val Ser Tyr Gln Thr Lys Val Asn Leu Leu Ser
    450                 455                 460

Ala Ile Lys Ser Pro Cys Gln Arg Glu Thr Pro Glu Gly Ala Glu Ala
465                 470                 475                 480

Lys Pro Trp Tyr Glu Pro Ile Tyr Leu Gly Gly Val Phe Gln Leu Glu
                485                 490                 495

Lys Gly Asp Arg Leu Ser Ala Glu Ile Asn Arg Pro Asp Tyr Leu Asp
            500                 505                 510

Phe Ala Glu Ser Gly Gln Val Tyr Phe Gly Ile Ile Ala Leu
        515                 520                 525

<210> SEQ ID NO 35
<211> LENGTH: 2253
<212> TYPE: DNA
<213> ORGANISM: Artificial Sequence
<220> FEATURE:
<223> OTHER INFORMATION: Description of Artificial Sequence:
      scFasL-AMAIZe sequence
<220> FEATURE:
<221> NAME/KEY: CDS
<222> LOCATION: (1)..(2250)

<400> SEQUENCE: 35 atg gac tgg acc tgg cgc gtg ttt tgc ctg ctc gcc gtg gct cct ggg      48
Met Asp Trp Thr Trp Arg Val Phe Cys Leu Leu Ala Val Ala Pro Gly
1               5                   10                  15 gcc cac agc cag gta cag ctg gtg cag tct ggg gga ggc atg gta gag      96
Ala His Ser Gln Val Gln Leu Val Gln Ser Gly Gly Gly Met Val Glu
            20                  25                  30 cct ggg ggg tcc ctt aga ctc tcc tgt gca gcc tct gga ttc act ttc     144
Pro Gly Gly Ser Leu Arg Leu Ser Cys Ala Ala Ser Gly Phe Thr Phe
        35                  40                  45 agt aat gcc tgg atg agc tgg gtc cgc cag gct cca ggg aag ggg ctg     192
Ser Asn Ala Trp Met Ser Trp Val Arg Gln Ala Pro Gly Lys Gly Leu
    50                  55                  60 gag tgg gtt ggc cgt ata aaa agc aaa gct ggt ggt ggg aca gca gag     240
Glu Trp Val Gly Arg Ile Lys Ser Lys Ala Gly Gly Gly Thr Ala Glu
```

-continued

```
Glu Trp Val Gly Arg Ile Lys Ser Lys Ala Gly Gly Thr Ala Glu
65              70              75              80 tac gct gca ccc gtg aaa ggc aga ttc acc atc tca aga gat gat tca    288
Tyr Ala Ala Pro Val Lys Gly Arg Phe Thr Ile Ser Arg Asp Asp Ser
                85              90              95 caa aac acg ctg tat ctg caa atg aac agc ctg aaa acc gac gac aca    336
Gln Asn Thr Leu Tyr Leu Gln Met Asn Ser Leu Lys Thr Asp Asp Thr
            100             105             110 gcc gtg tat tac tgt acc aca cat gtc tac ggt gcc ccc cgg aac tgg    384
Ala Val Tyr Tyr Cys Thr Thr His Val Tyr Gly Ala Pro Arg Asn Trp
            115             120             125 ggc cag gga tcc ctg gtc acc gtc tcc tca gcc tcc acc aag ggc cca    432
Gly Gln Gly Ser Leu Val Thr Val Ser Ser Ala Ser Thr Lys Gly Pro
130             135             140 aag ctt gaa gaa ggt gaa ttt tca gaa gca cgc gta cag tct gtg ttg    480
Lys Leu Glu Glu Gly Glu Phe Ser Glu Ala Arg Val Gln Ser Val Leu
145             150             155             160 act cag ccg ccc tca gtg tct gcg gcc cca gga cag aag gtc acc atc    528
Thr Gln Pro Pro Ser Val Ser Ala Ala Pro Gly Gln Lys Val Thr Ile
                165             170             175 tcc tgc tct gga agc agc tcc aac att gga aat aat tat gtc tcc tgg    576
Ser Cys Ser Gly Ser Ser Ser Asn Ile Gly Asn Asn Tyr Val Ser Trp
            180             185             190 tac gtt caa ctc cca gga aca gcc ccc aaa ctc ctc att tat gac aat    624
Tyr Val Gln Leu Pro Gly Thr Ala Pro Lys Leu Leu Ile Tyr Asp Asn
            195             200             205 aat aag cga ttc tca gga gtt cct gac cga ttc tct ggc tcc aag tct    672
Asn Lys Arg Phe Ser Gly Val Pro Asp Arg Phe Ser Gly Ser Lys Ser
210             215             220 ggc acg tca gcc acc ctg ggc atc acc ggg ctc cag act ggg gac gag    720
Gly Thr Ser Ala Thr Leu Gly Ile Thr Gly Leu Gln Thr Gly Asp Glu
225             230             235             240 gcc gat tat tac tgc gga gca tgg gat ggc agc ctg cgt gaa gcg gta    768
Ala Asp Tyr Tyr Cys Gly Ala Trp Asp Gly Ser Leu Arg Glu Ala Val
                245             250             255 ttc ggc gga ggg acc aag gtc acc gtc cta ggt gcg gcc gca gtt gag    816
Phe Gly Gly Gly Thr Lys Val Thr Val Leu Gly Ala Ala Ala Val Glu
            260             265             270 ctc gag gcg gcc gcg gat tac aaa gac gat gac gat aaa gaa ttc acg    864
Leu Glu Ala Ala Ala Asp Tyr Lys Asp Asp Asp Asp Lys Glu Phe Thr
275             280             285 cgt gaa aaa aag gag ctg agg aaa gtg gcc cat tta aca ggc aag tcc    912
Arg Glu Lys Lys Glu Leu Arg Lys Val Ala His Leu Thr Gly Lys Ser
290             295             300 aac tca agg tcc atg cct ctg gaa tgg gaa gac acc tat gga att gtc    960
Asn Ser Arg Ser Met Pro Leu Glu Trp Glu Asp Thr Tyr Gly Ile Val
305             310             315             320 ctg ctt tct gga gtg aag tat aag aag ggt ggc ctt gtg atc aat gaa    1008
Leu Leu Ser Gly Val Lys Tyr Lys Lys Gly Gly Leu Val Ile Asn Glu
                325             330             335 act ggg ctg tac ttt gta tat tcc aaa gta tac ttc cgg ggt caa tct    1056
Thr Gly Leu Tyr Phe Val Tyr Ser Lys Val Tyr Phe Arg Gly Gln Ser
            340             345             350 tgc aac aac ctg ccc ctg agc cac aag gtc tac atg agg aac tct aag    1104
Cys Asn Asn Leu Pro Leu Ser His Lys Val Tyr Met Arg Asn Ser Lys
            355             360             365 tat ccc cag gat ctg gtg atg atg gag ggg aag atg atg agc tac tgc    1152
Tyr Pro Gln Asp Leu Val Met Met Glu Gly Lys Met Met Ser Tyr Cys
370             375             380
```

```
act act ggg cag atg tgg gcc cgc agc agc tac ctg ggg gca gtg ttc            1200
Thr Thr Gly Gln Met Trp Ala Arg Ser Ser Tyr Leu Gly Ala Val Phe
385                 390                 395                 400 aat ctt acc agt gct gat cat tta tat gtc aac gta tct gag ctc tct            1248
Asn Leu Thr Ser Ala Asp His Leu Tyr Val Asn Val Ser Glu Leu Ser
            405                 410                 415 ctg gtc aat ttt gag gaa tct cag acg ttt ttc ggc tta tat aag ctc            1296
Leu Val Asn Phe Glu Glu Ser Gln Thr Phe Phe Gly Leu Tyr Lys Leu
        420                 425                 430 ggt ggc ggt tct ggt ggc ggt tct ggt ggc ggt tct ggt ggc gga tca            1344
Gly Gly Gly Ser Gly Gly Gly Ser Gly Gly Gly Ser Gly Gly Gly Ser
            435                 440                 445 gaa aaa aag gag ctg agg aaa gtg gcc cat tta aca ggc aag tcc aac            1392
Glu Lys Lys Glu Leu Arg Lys Val Ala His Leu Thr Gly Lys Ser Asn
        450                 455                 460 tca agg tcc atg cct ctg gaa tgg gaa gac acc tat gga att gtc ctg            1440
Ser Arg Ser Met Pro Leu Glu Trp Glu Asp Thr Tyr Gly Ile Val Leu
465                 470                 475                 480 ctt tct gga gtg aag tat aag aag ggt ggc ctt gtg atc aat gaa act            1488
Leu Ser Gly Val Lys Tyr Lys Lys Gly Gly Leu Val Ile Asn Glu Thr
            485                 490                 495 ggg ctg tac ttt gta tat tcc aaa gta tac ttc cgg ggt caa tct tgc            1536
Gly Leu Tyr Phe Val Tyr Ser Lys Val Tyr Phe Arg Gly Gln Ser Cys
        500                 505                 510 aac aac ctg ccc ctg agc cac aag gtc tac atg agg aac tct aag tat            1584
Asn Asn Leu Pro Leu Ser His Lys Val Tyr Met Arg Asn Ser Lys Tyr
            515                 520                 525 ccc cag gat ctg gtg atg atg gag ggg aag atg atg agc tac tgc act            1632
Pro Gln Asp Leu Val Met Met Glu Gly Lys Met Met Ser Tyr Cys Thr
530                 535                 540 act ggg cag atg tgg gcc cgc agc agc tac ctg ggg gca gtg ttc aat            1680
Thr Gly Gln Met Trp Ala Arg Ser Ser Tyr Leu Gly Ala Val Phe Asn
545                 550                 555                 560 ctt acc agt gct gat cat tta tat gtc aac gta tct gag ctc tct ctg            1728
Leu Thr Ser Ala Asp His Leu Tyr Val Asn Val Ser Glu Leu Ser Leu
            565                 570                 575 gtc aat ttt gag gaa tct cag acg ttt ttc ggc tta tat aag ctc ggt            1776
Val Asn Phe Glu Glu Ser Gln Thr Phe Phe Gly Leu Tyr Lys Leu Gly
        580                 585                 590 ggc ggt tct ggt ggc ggt tct ggt ggc ggt tct ggt ggc gga tcc gaa            1824
Gly Gly Ser Gly Gly Gly Ser Gly Gly Gly Ser Gly Gly Gly Ser Glu
            595                 600                 605 aaa aag gag ctg agg aaa gtg gcc cat tta aca ggc aag tcc aac tca            1872
Lys Lys Glu Leu Arg Lys Val Ala His Leu Thr Gly Lys Ser Asn Ser
610                 615                 620 agg tcc atg cct ctg gaa tgg gaa gac acc tat gga att gtc ctg ctt            1920
Arg Ser Met Pro Leu Glu Trp Glu Asp Thr Tyr Gly Ile Val Leu Leu
625                 630                 635                 640 tct gga gtg aag tat aag aag ggt ggc ctt gtg atc aat gaa act ggg            1968
Ser Gly Val Lys Tyr Lys Lys Gly Gly Leu Val Ile Asn Glu Thr Gly
            645                 650                 655 ctg tac ttt gta tat tcc aaa gta tac ttc cgg ggt caa tct tgc aac            2016
Leu Tyr Phe Val Tyr Ser Lys Val Tyr Phe Arg Gly Gln Ser Cys Asn
        660                 665                 670 aac ctg ccc ctg agc cac aag gtc tac atg agg aac tct aag tat ccc            2064
Asn Leu Pro Leu Ser His Lys Val Tyr Met Arg Asn Ser Lys Tyr Pro
            675                 680                 685 cag gat ctg gtg atg atg gag ggg aag atg atg agc tac tgc act act            2112
Gln Asp Leu Val Met Met Glu Gly Lys Met Met Ser Tyr Cys Thr Thr
690                 695                 700
```

```
ggg cag atg tgg gcc cgc agc agc tac ctg ggg gca gtg ttc aat ctt    2160
Gly Gln Met Trp Ala Arg Ser Ser Tyr Leu Gly Ala Val Phe Asn Leu
705             710                 715                 720 acc agt gct gat cat tta tat gtc aac gta tct gag ctc tct ctg gtc    2208
Thr Ser Ala Asp His Leu Tyr Val Asn Val Ser Glu Leu Ser Leu Val
                725                 730                 735 aat ttt gag gaa tct cag acg ttt ttc ggc tta tat aag ctc tga        2253
Asn Phe Glu Glu Ser Gln Thr Phe Phe Gly Leu Tyr Lys Leu
            740                 745                 750

<210> SEQ ID NO 36
<211> LENGTH: 750
<212> TYPE: PRT
<213> ORGANISM: Artificial Sequence
<220> FEATURE:
<223> OTHER INFORMATION: Description of Artificial Sequence:
      scFasL-AMAIZe peptide sequence

<400> SEQUENCE: 36
```

Met Asp Trp Thr Trp Arg Val Phe Cys Leu Leu Ala Val Ala Pro Gly
1               5                   10                  15

Ala His Ser Gln Val Gln Leu Val Gln Ser Gly Gly Gly Met Val Glu
            20                  25                  30

Pro Gly Gly Ser Leu Arg Leu Ser Cys Ala Ala Ser Gly Phe Thr Phe
        35                  40                  45

Ser Asn Ala Trp Met Ser Trp Val Arg Gln Ala Pro Gly Lys Gly Leu
    50                  55                  60

Glu Trp Val Gly Arg Ile Lys Ser Lys Ala Gly Gly Gly Thr Ala Glu
65                  70                  75                  80

Tyr Ala Ala Pro Val Lys Gly Arg Phe Thr Ile Ser Arg Asp Asp Ser
                85                  90                  95

Gln Asn Thr Leu Tyr Leu Gln Met Asn Ser Leu Lys Thr Asp Asp Thr
            100                 105                 110

Ala Val Tyr Tyr Cys Thr Thr His Val Tyr Gly Ala Pro Arg Asn Trp
        115                 120                 125

Gly Gln Gly Ser Leu Val Thr Val Ser Ser Ala Ser Thr Lys Gly Pro
    130                 135                 140

Lys Leu Glu Glu Gly Glu Phe Ser Glu Ala Arg Val Gln Ser Val Leu
145                 150                 155                 160

Thr Gln Pro Pro Ser Val Ser Ala Ala Pro Gly Gln Lys Val Thr Ile
                165                 170                 175

Ser Cys Ser Gly Ser Ser Ser Asn Ile Gly Asn Asn Tyr Val Ser Trp
            180                 185                 190

Tyr Val Gln Leu Pro Gly Thr Ala Pro Lys Leu Leu Ile Tyr Asp Asn
        195                 200                 205

Asn Lys Arg Phe Ser Gly Val Pro Asp Arg Phe Ser Gly Ser Lys Ser
    210                 215                 220

Gly Thr Ser Ala Thr Leu Gly Ile Thr Gly Leu Gln Thr Gly Asp Glu
225                 230                 235                 240

Ala Asp Tyr Tyr Cys Gly Ala Trp Asp Gly Ser Leu Arg Glu Ala Val
                245                 250                 255

Phe Gly Gly Gly Thr Lys Val Thr Leu Gly Ala Ala Ala Val Glu
            260                 265                 270

Leu Glu Ala Ala Ala Asp Tyr Lys Asp Asp Asp Lys Glu Phe Thr
        275                 280                 285

Arg Glu Lys Lys Glu Leu Arg Lys Val Ala His Leu Thr Gly Lys Ser

```
            290                 295                 300
Asn Ser Arg Ser Met Pro Leu Glu Trp Glu Asp Thr Tyr Gly Ile Val
305                 310                 315                 320

Leu Leu Ser Gly Val Lys Tyr Lys Gly Gly Leu Val Ile Asn Glu
                325                 330                 335

Thr Gly Leu Tyr Phe Val Tyr Ser Lys Val Tyr Phe Arg Gly Gln Ser
                340                 345                 350

Cys Asn Asn Leu Pro Leu Ser His Lys Val Tyr Met Arg Asn Ser Lys
                355                 360                 365

Tyr Pro Gln Asp Leu Val Met Met Glu Gly Lys Met Met Ser Tyr Cys
370                 375                 380

Thr Thr Gly Gln Met Trp Ala Arg Ser Ser Tyr Leu Gly Ala Val Phe
385                 390                 395                 400

Asn Leu Thr Ser Ala Asp His Leu Tyr Val Asn Val Ser Glu Leu Ser
                405                 410                 415

Leu Val Asn Phe Glu Glu Ser Gln Thr Phe Phe Gly Leu Tyr Lys Leu
                420                 425                 430

Gly Gly Gly Ser Gly Gly Gly Ser Gly Gly Gly Ser Gly Gly Gly Ser
                435                 440                 445

Glu Lys Lys Glu Leu Arg Lys Val Ala His Leu Thr Gly Lys Ser Asn
                450                 455                 460

Ser Arg Ser Met Pro Leu Glu Trp Glu Asp Thr Tyr Gly Ile Val Leu
465                 470                 475                 480

Leu Ser Gly Val Lys Tyr Lys Gly Gly Leu Val Ile Asn Glu Thr
                485                 490                 495

Gly Leu Tyr Phe Val Tyr Ser Lys Val Tyr Phe Arg Gly Gln Ser Cys
                500                 505                 510

Asn Asn Leu Pro Leu Ser His Lys Val Tyr Met Arg Asn Ser Lys Tyr
                515                 520                 525

Pro Gln Asp Leu Val Met Met Glu Gly Lys Met Met Ser Tyr Cys Thr
530                 535                 540

Thr Gly Gln Met Trp Ala Arg Ser Ser Tyr Leu Gly Ala Val Phe Asn
545                 550                 555                 560

Leu Thr Ser Ala Asp His Leu Tyr Val Asn Val Ser Glu Leu Ser Leu
                565                 570                 575

Val Asn Phe Glu Glu Ser Gln Thr Phe Phe Gly Leu Tyr Lys Leu Gly
                580                 585                 590

Gly Gly Ser Gly Gly Gly Ser Gly Gly Gly Ser Gly Gly Gly Ser Glu
                595                 600                 605

Lys Lys Glu Leu Arg Lys Val Ala His Leu Thr Gly Lys Ser Asn Ser
                610                 615                 620

Arg Ser Met Pro Leu Glu Trp Glu Asp Thr Tyr Gly Ile Val Leu Leu
625                 630                 635                 640

Ser Gly Val Lys Tyr Lys Lys Gly Gly Leu Val Ile Asn Glu Thr Gly
                645                 650                 655

Leu Tyr Phe Val Tyr Ser Lys Val Tyr Phe Arg Gly Gln Ser Cys Asn
                660                 665                 670

Asn Leu Pro Leu Ser His Lys Val Tyr Met Arg Asn Ser Lys Tyr Pro
                675                 680                 685

Gln Asp Leu Val Met Met Glu Gly Lys Met Met Ser Tyr Cys Thr Thr
                690                 695                 700

Gly Gln Met Trp Ala Arg Ser Ser Tyr Leu Gly Ala Val Phe Asn Leu
705                 710                 715                 720
```

```
Thr Ser Ala Asp His Leu Tyr Val Asn Val Ser Glu Leu Ser Leu Val
            725                 730                 735

Asn Phe Glu Glu Ser Gln Thr Phe Phe Gly Leu Tyr Lys Leu
        740                 745                 750

<210> SEQ ID NO 37
<211> LENGTH: 2646
<212> TYPE: DNA
<213> ORGANISM: Artificial Sequence
<220> FEATURE:
<223> OTHER INFORMATION: Description of Artificial Sequence:
      scTRAIL-AMAIZe sequence
<220> FEATURE:
<221> NAME/KEY: CDS
<222> LOCATION: (1)..(2643)

<400> SEQUENCE: 37 atg gac tgg acc tgg cgc gtg ttt tgc ctg ctc gcc gtg gct cct ggg      48
Met Asp Trp Thr Trp Arg Val Phe Cys Leu Leu Ala Val Ala Pro Gly
 1               5                  10                  15 gcc cac agc cag gta cag ctg gtg cag tct ggg gga ggc atg gta gag      96
Ala His Ser Gln Val Gln Leu Val Gln Ser Gly Gly Gly Met Val Glu
             20                  25                  30 cct ggg ggg tcc ctt aga ctc tcc tgt gca gcc tct gga ttc act ttc     144
Pro Gly Gly Ser Leu Arg Leu Ser Cys Ala Ala Ser Gly Phe Thr Phe
         35                  40                  45 agt aat gcc tgg atg agc tgg gtc cgc cag gct cca ggg aag ggg ctg     192
Ser Asn Ala Trp Met Ser Trp Val Arg Gln Ala Pro Gly Lys Gly Leu
     50                  55                  60 gag tgg gtt ggc cgt ata aaa agc aaa gct ggt ggt ggg aca gca gag     240
Glu Trp Val Gly Arg Ile Lys Ser Lys Ala Gly Gly Gly Thr Ala Glu
 65                  70                  75                  80 tac gct gca ccc gtg aaa ggc aga ttc acc atc tca aga gat gat tca     288
Tyr Ala Ala Pro Val Lys Gly Arg Phe Thr Ile Ser Arg Asp Asp Ser
                 85                  90                  95 caa aac acg ctg tat ctg caa atg aac agc ctg aaa acc gac gac aca     336
Gln Asn Thr Leu Tyr Leu Gln Met Asn Ser Leu Lys Thr Asp Asp Thr
            100                 105                 110 gcc gtg tat tac tgt acc aca cat gtc tac ggt gcc ccc cgg aac tgg     384
Ala Val Tyr Tyr Cys Thr Thr His Val Tyr Gly Ala Pro Arg Asn Trp
        115                 120                 125 ggc cag gga tcc ctg gtc acc gtc tcc tca gcc tcc acc aag ggc cca     432
Gly Gln Gly Ser Leu Val Thr Val Ser Ser Ala Ser Thr Lys Gly Pro
    130                 135                 140 aag ctt gaa gaa ggt gaa ttt tca gaa gca cgc gta cag tct gtg ttg     480
Lys Leu Glu Glu Gly Glu Phe Ser Glu Ala Arg Val Gln Ser Val Leu
145                 150                 155                 160 act cag ccg ccc tca gtg tct gcg gcc cca gga cag aag gtc acc atc     528
Thr Gln Pro Pro Ser Val Ser Ala Ala Pro Gly Gln Lys Val Thr Ile
                165                 170                 175 tcc tgc tct gga agc agc tcc aac att gga aat aat tat gtc tcc tgg     576
Ser Cys Ser Gly Ser Ser Ser Asn Ile Gly Asn Asn Tyr Val Ser Trp
            180                 185                 190 tac gtt caa ctc cca gga aca gcc ccc aaa ctc ctc att tat gac aat     624
Tyr Val Gln Leu Pro Gly Thr Ala Pro Lys Leu Leu Ile Tyr Asp Asn
        195                 200                 205 aat aag cga ttc tca gga gtt cct gac cga ttc tct ggc tcc aag tct     672
Asn Lys Arg Phe Ser Gly Val Pro Asp Arg Phe Ser Gly Ser Lys Ser
    210                 215                 220 ggc acg tca gcc acc ctg ggc atc acc ggg ctc cag act ggg gac gag     720
Gly Thr Ser Ala Thr Leu Gly Ile Thr Gly Leu Gln Thr Gly Asp Glu
```

```
                225                 230                 235                 240
gcc gat tat tac tgc gga gca tgg gat ggc agc ctg cgt gaa gcg gta    768
Ala Asp Tyr Tyr Cys Gly Ala Trp Asp Gly Ser Leu Arg Glu Ala Val
                    245                 250                 255 ttc ggc gga ggg acc aag gtc acc gtc cta ggt gcg gcc gca gtt gag    816
Phe Gly Gly Gly Thr Lys Val Thr Val Leu Gly Ala Ala Ala Val Glu
            260                 265                 270 ctc gag gcg gcc gcg gat tac aaa gac gat gac gat aaa gaa ttc gga    864
Leu Glu Ala Ala Ala Asp Tyr Lys Asp Asp Asp Asp Lys Glu Phe Gly
        275                 280                 285 acc tct gag gaa acc att tct aca gtt caa gaa aag caa caa aat att    912
Thr Ser Glu Glu Thr Ile Ser Thr Val Gln Glu Lys Gln Gln Asn Ile
    290                 295                 300 tct ccc cta gtg aga gaa aga ggt cct cag aga gta gca gct cac ata    960
Ser Pro Leu Val Arg Glu Arg Gly Pro Gln Arg Val Ala Ala His Ile
305                 310                 315                 320 act ggg acc aga gga aga agc aac aca ttg tct tct cca aac tcc aag   1008
Thr Gly Thr Arg Gly Arg Ser Asn Thr Leu Ser Ser Pro Asn Ser Lys
                325                 330                 335 aat gaa aag gct ctg ggc cgc aaa ata aac tcc tgg gaa tca tca agg   1056
Asn Glu Lys Ala Leu Gly Arg Lys Ile Asn Ser Trp Glu Ser Ser Arg
            340                 345                 350 agt ggg cat tca ttc ctg agc aac ttg cac ttg agg aat ggt gaa ctg   1104
Ser Gly His Ser Phe Leu Ser Asn Leu His Leu Arg Asn Gly Glu Leu
        355                 360                 365 gtc atc cat gaa aaa ggg ttt tac tac atc tat tcc caa aca tac ttt   1152
Val Ile His Glu Lys Gly Phe Tyr Tyr Ile Tyr Ser Gln Thr Tyr Phe
    370                 375                 380 cga ttt cag gag gaa ata aaa gaa aac aca aag aac gac aaa caa atg   1200
Arg Phe Gln Glu Glu Ile Lys Glu Asn Thr Lys Asn Asp Lys Gln Met
385                 390                 395                 400 gtc caa tat att tac aaa tac aca agt tat cct gac cct ata ttg ttg   1248
Val Gln Tyr Ile Tyr Lys Tyr Thr Ser Tyr Pro Asp Pro Ile Leu Leu
                405                 410                 415 atg aaa agt gct aga aat agt tgt tgg tct aaa gat gca gaa tat gga   1296
Met Lys Ser Ala Arg Asn Ser Cys Trp Ser Lys Asp Ala Glu Tyr Gly
            420                 425                 430 ctc tat tcc atc tat caa ggg gga ata ttt gag ctt aag gaa aat gac   1344
Leu Tyr Ser Ile Tyr Gln Gly Gly Ile Phe Glu Leu Lys Glu Asn Asp
        435                 440                 445 aga att ttt gtt tct gta aca aat gag cac ttg ata gac atg gac cat   1392
Arg Ile Phe Val Ser Val Thr Asn Glu His Leu Ile Asp Met Asp His
    450                 455                 460 gaa gcc agt ttt ttc ggg gcc ttt tta gtt ggc ggt ggc ggt tct ggt   1440
Glu Ala Ser Phe Phe Gly Ala Phe Leu Val Gly Gly Gly Gly Ser Gly
465                 470                 475                 480 ggc ggt tct ggt ggc ggt tct ggt ggc gga tca acc tct gag gaa acc   1488
Gly Gly Ser Gly Gly Gly Ser Gly Gly Gly Ser Thr Ser Glu Glu Thr
                485                 490                 495 att tct aca gtt caa gaa aag caa caa aat att tct ccc cta gtg aga   1536
Ile Ser Thr Val Gln Glu Lys Gln Gln Asn Ile Ser Pro Leu Val Arg
            500                 505                 510 gaa aga ggt cct cag aga gta gca gct cac ata act ggg acc aga gga   1584
Glu Arg Gly Pro Gln Arg Val Ala Ala His Ile Thr Gly Thr Arg Gly
        515                 520                 525 aga agc aac aca ttg tct tct cca aac tcc aag aat gaa aag gct ctg   1632
Arg Ser Asn Thr Leu Ser Ser Pro Asn Ser Lys Asn Glu Lys Ala Leu
    530                 535                 540 ggc cgc aaa ata aac tcc tgg gaa tca tca agg agt ggg cat tca ttc   1680
```

-continued

| | |
|---|---|
| Gly Arg Lys Ile Asn Ser Trp Glu Ser Ser Arg Ser Gly His Ser Phe<br>545                    550                    555                    560 | |
| ctg agc aac ttg cac ttg agg aat ggt gaa ctg gtc atc cat gaa aaa<br>Leu Ser Asn Leu His Leu Arg Asn Gly Glu Leu Val Ile His Glu Lys<br>                    565                    570                    575 | 1728 |
| ggg ttt tac tac atc tat tcc caa aca tac ttt cga ttt cag gag gaa<br>Gly Phe Tyr Tyr Ile Tyr Ser Gln Thr Tyr Phe Arg Phe Gln Glu Glu<br>                580                    585                    590 | 1776 |
| ata aaa gaa aac aca aag aac gac aaa caa atg gtc caa tat att tac<br>Ile Lys Glu Asn Thr Lys Asn Asp Lys Gln Met Val Gln Tyr Ile Tyr<br>595                    600                    605 | 1824 |
| aaa tac aca agt tat cct gac cct ata ttg ttg atg aaa agt gct aga<br>Lys Tyr Thr Ser Tyr Pro Asp Pro Ile Leu Leu Met Lys Ser Ala Arg<br>          610                    615                    620 | 1872 |
| aat agt tgt tgg tct aaa gat gca gaa tat gga ctc tat tcc atc tat<br>Asn Ser Cys Trp Ser Lys Asp Ala Glu Tyr Gly Leu Tyr Ser Ile Tyr<br>625                    630                    635                    640 | 1920 |
| caa ggg gga ata ttt gag ctt aag gaa aat gac aga att ttt gtt tct<br>Gln Gly Gly Ile Phe Glu Leu Lys Glu Asn Asp Arg Ile Phe Val Ser<br>                    645                    650                    655 | 1968 |
| gta aca aat gag cac ttg ata gac atg gac cat gaa gcc agt ttt ttc<br>Val Thr Asn Glu His Leu Ile Asp Met Asp His Glu Ala Ser Phe Phe<br>                660                    665                    670 | 2016 |
| ggg gcc ttt tta gtt ggc ggt ggc ggt tct ggt ggc ggt tct ggt ggc<br>Gly Ala Phe Leu Val Gly Gly Gly Gly Ser Gly Gly Gly Ser Gly Gly<br>          675                    680                    685 | 2064 |
| ggt tct ggt ggc gga tcc acc tct gag gaa acc att tct aca gtt caa<br>Gly Ser Gly Gly Gly Ser Thr Ser Glu Glu Thr Ile Ser Thr Val Gln<br>690                    695                    700 | 2112 |
| gaa aag caa caa aat att tct ccc cta gtg aga gaa aga ggt cct cag<br>Glu Lys Gln Gln Asn Ile Ser Pro Leu Val Arg Glu Arg Gly Pro Gln<br>705                    710                    715                    720 | 2160 |
| aga gta gca gct cac ata act ggg acc aga gga aga agc aac aca ttg<br>Arg Val Ala Ala His Ile Thr Gly Thr Arg Gly Arg Ser Asn Thr Leu<br>                725                    730                    735 | 2208 |
| tct tct cca aac tcc aag aat gaa aag gct ctg ggc cgc aaa ata aac<br>Ser Ser Pro Asn Ser Lys Asn Glu Lys Ala Leu Gly Arg Lys Ile Asn<br>                    740                    745                    750 | 2256 |
| tcc tgg gaa tca tca agg agt ggg cat tca ttc ctg agc aac ttg cac<br>Ser Trp Glu Ser Ser Arg Ser Gly His Ser Phe Leu Ser Asn Leu His<br>          755                    760                    765 | 2304 |
| ttg agg aat ggt gaa ctg gtc atc cat gaa aaa ggg ttt tac tac atc<br>Leu Arg Asn Gly Glu Leu Val Ile His Glu Lys Gly Phe Tyr Tyr Ile<br>770                    775                    780 | 2352 |
| tat tcc caa aca tac ttt cga ttt cag gag gaa ata aaa gaa aac aca<br>Tyr Ser Gln Thr Tyr Phe Arg Phe Gln Glu Glu Ile Lys Glu Asn Thr<br>785                    790                    795                    800 | 2400 |
| aag aac gac aaa caa atg gtc caa tat att tac aaa tac aca agt tat<br>Lys Asn Asp Lys Gln Met Val Gln Tyr Ile Tyr Lys Tyr Thr Ser Tyr<br>                805                    810                    815 | 2448 |
| cct gac cct ata ttg ttg atg aaa agt gct aga aat agt tgt tgg tct<br>Pro Asp Pro Ile Leu Leu Met Lys Ser Ala Arg Asn Ser Cys Trp Ser<br>                    820                    825                    830 | 2496 |
| aaa gat gca gaa tat gga ctc tat tcc atc tat caa ggg gga ata ttt<br>Lys Asp Ala Glu Tyr Gly Leu Tyr Ser Ile Tyr Gln Gly Gly Ile Phe<br>          835                    840                    845 | 2544 |
| gag ctt aag gaa aat gac aga att ttt gtt tct gta aca aat gag cac<br>Glu Leu Lys Glu Asn Asp Arg Ile Phe Val Ser Val Thr Asn Glu His<br>850                    855                    860 | 2592 |

```
ttg ata gac atg gac cat gaa gcc agt ttt ttc ggg gcc ttt tta gtt    2640
Leu Ile Asp Met Asp His Glu Ala Ser Phe Phe Gly Ala Phe Leu Val
865                 870                 875                 880 ggc tga                                                             2646
Gly
```

<210> SEQ ID NO 38
<211> LENGTH: 881
<212> TYPE: PRT
<213> ORGANISM: Artificial Sequence
<220> FEATURE:
<223> OTHER INFORMATION: Description of Artificial Sequence:
      scTRAIL-AMAIZe peptide sequence

<400> SEQUENCE: 38

```
Met Asp Trp Thr Trp Arg Val Phe Cys Leu Leu Ala Val Ala Pro Gly
1               5                   10                  15

Ala His Ser Gln Val Gln Leu Val Gln Ser Gly Gly Gly Met Val Glu
            20                  25                  30

Pro Gly Gly Ser Leu Arg Leu Ser Cys Ala Ala Ser Gly Phe Thr Phe
        35                  40                  45

Ser Asn Ala Trp Met Ser Trp Val Arg Gln Ala Pro Gly Lys Gly Leu
    50                  55                  60

Glu Trp Val Gly Arg Ile Lys Ser Lys Ala Gly Gly Gly Thr Ala Glu
65                  70                  75                  80

Tyr Ala Ala Pro Val Lys Gly Arg Phe Thr Ile Ser Arg Asp Asp Ser
                85                  90                  95

Gln Asn Thr Leu Tyr Leu Gln Met Asn Ser Leu Lys Thr Asp Asp Thr
            100                 105                 110

Ala Val Tyr Tyr Cys Thr Thr His Val Tyr Gly Ala Pro Arg Asn Trp
        115                 120                 125

Gly Gln Gly Ser Leu Val Thr Val Ser Ser Ala Ser Thr Lys Gly Pro
    130                 135                 140

Lys Leu Glu Glu Gly Glu Phe Ser Glu Ala Arg Val Gln Ser Val Leu
145                 150                 155                 160

Thr Gln Pro Pro Ser Val Ser Ala Ala Pro Gly Gln Lys Val Thr Ile
                165                 170                 175

Ser Cys Ser Gly Ser Ser Ser Asn Ile Gly Asn Asn Tyr Val Ser Trp
            180                 185                 190

Tyr Val Gln Leu Pro Gly Thr Ala Pro Lys Leu Leu Ile Tyr Asp Asn
        195                 200                 205

Asn Lys Arg Phe Ser Gly Val Pro Asp Arg Phe Ser Gly Ser Lys Ser
    210                 215                 220

Gly Thr Ser Ala Thr Leu Gly Ile Thr Gly Leu Gln Thr Gly Asp Glu
225                 230                 235                 240

Ala Asp Tyr Tyr Cys Gly Ala Trp Asp Gly Ser Leu Arg Glu Ala Val
                245                 250                 255

Phe Gly Gly Gly Thr Lys Val Thr Val Leu Gly Ala Ala Ala Val Glu
            260                 265                 270

Leu Glu Ala Ala Ala Asp Tyr Lys Asp Asp Asp Lys Glu Phe Gly
        275                 280                 285

Thr Ser Glu Glu Thr Ile Ser Thr Val Gln Glu Lys Gln Gln Asn Ile
    290                 295                 300

Ser Pro Leu Val Arg Glu Arg Gly Pro Gln Arg Val Ala Ala His Ile
305                 310                 315                 320

Thr Gly Thr Arg Gly Arg Ser Asn Thr Leu Ser Ser Pro Asn Ser Lys
```

```
                    325                 330                 335
Asn Glu Lys Ala Leu Gly Arg Lys Ile Asn Ser Trp Glu Ser Ser Arg
                340                 345                 350

Ser Gly His Ser Phe Leu Ser Asn Leu His Leu Arg Asn Gly Glu Leu
                355                 360                 365

Val Ile His Glu Lys Gly Phe Tyr Tyr Ile Tyr Ser Gln Thr Tyr Phe
            370                 375                 380

Arg Phe Gln Glu Glu Ile Lys Glu Asn Thr Lys Asn Asp Lys Gln Met
385                 390                 395                 400

Val Gln Tyr Ile Tyr Lys Tyr Thr Ser Tyr Pro Asp Pro Ile Leu Leu
                405                 410                 415

Met Lys Ser Ala Arg Asn Ser Cys Trp Ser Lys Asp Ala Glu Tyr Gly
                420                 425                 430

Leu Tyr Ser Ile Tyr Gln Gly Gly Ile Phe Glu Leu Lys Glu Asn Asp
                435                 440                 445

Arg Ile Phe Val Ser Val Thr Asn Glu His Leu Ile Asp Met Asp His
            450                 455                 460

Glu Ala Ser Phe Phe Gly Ala Phe Leu Val Gly Gly Gly Ser Gly
465                 470                 475                 480

Gly Gly Ser Gly Gly Gly Ser Gly Gly Gly Ser Thr Ser Glu Glu Thr
                485                 490                 495

Ile Ser Thr Val Gln Glu Lys Gln Gln Asn Ile Ser Pro Leu Val Arg
            500                 505                 510

Glu Arg Gly Pro Gln Arg Val Ala Ala His Ile Thr Gly Thr Arg Gly
                515                 520                 525

Arg Ser Asn Thr Leu Ser Ser Pro Asn Ser Lys Asn Glu Lys Ala Leu
                530                 535                 540

Gly Arg Lys Ile Asn Ser Trp Glu Ser Ser Arg Ser Gly His Ser Phe
545                 550                 555                 560

Leu Ser Asn Leu His Leu Arg Asn Gly Glu Leu Val Ile His Glu Lys
                565                 570                 575

Gly Phe Tyr Tyr Ile Tyr Ser Gln Thr Tyr Phe Arg Phe Gln Glu Glu
                580                 585                 590

Ile Lys Glu Asn Thr Lys Asn Asp Lys Gln Met Val Gln Tyr Ile Tyr
                595                 600                 605

Lys Tyr Thr Ser Tyr Pro Asp Pro Ile Leu Leu Met Lys Ser Ala Arg
            610                 615                 620

Asn Ser Cys Trp Ser Lys Asp Ala Glu Tyr Gly Leu Tyr Ser Ile Tyr
625                 630                 635                 640

Gln Gly Gly Ile Phe Glu Leu Lys Glu Asn Asp Arg Ile Phe Val Ser
                645                 650                 655

Val Thr Asn Glu His Leu Ile Asp Met Asp His Glu Ala Ser Phe Phe
                660                 665                 670

Gly Ala Phe Leu Val Gly Gly Gly Ser Gly Gly Gly Ser Gly Gly Gly
            675                 680                 685

Gly Ser Gly Gly Gly Ser Thr Ser Glu Glu Thr Ile Ser Thr Val Gln
            690                 695                 700

Glu Lys Gln Gln Asn Ile Ser Pro Leu Val Arg Glu Arg Gly Pro Gln
705                 710                 715                 720

Arg Val Ala Ala His Ile Thr Gly Thr Arg Gly Arg Ser Asn Thr Leu
                725                 730                 735

Ser Ser Pro Asn Ser Lys Asn Glu Lys Ala Leu Gly Arg Lys Ile Asn
                740                 745                 750
```

```
Ser Trp Glu Ser Ser Arg Ser Gly His Ser Phe Leu Ser Asn Leu His
        755                 760                 765

Leu Arg Asn Gly Glu Leu Val Ile His Glu Lys Gly Phe Tyr Tyr Ile
770                 775                 780

Tyr Ser Gln Thr Tyr Phe Arg Phe Gln Glu Glu Ile Lys Glu Asn Thr
785                 790                 795                 800

Lys Asn Asp Lys Gln Met Val Gln Tyr Ile Tyr Lys Tyr Thr Ser Tyr
                805                 810                 815

Pro Asp Pro Ile Leu Leu Met Lys Ser Ala Arg Asn Ser Cys Trp Ser
                820                 825                 830

Lys Asp Ala Glu Tyr Gly Leu Tyr Ser Ile Tyr Gln Gly Gly Ile Phe
                835                 840                 845

Glu Leu Lys Glu Asn Asp Arg Ile Phe Val Ser Val Thr Asn Glu His
            850                 855                 860

Leu Ile Asp Met Asp His Glu Ala Ser Phe Phe Gly Ala Phe Leu Val
865                 870                 875                 880

Gly

<210> SEQ ID NO 39
<211> LENGTH: 2358
<212> TYPE: DNA
<213> ORGANISM: Artificial Sequence
<220> FEATURE:
<223> OTHER INFORMATION: Description of Artificial Sequence:
      scTNF-AMAIZe sequence
<220> FEATURE:
<221> NAME/KEY: CDS
<222> LOCATION: (1)..(2355)

<400> SEQUENCE: 39 atg gac tgg acc tgg cgc gtg ttt tgc ctg ctc gcc gtg gct cct ggg      48
Met Asp Trp Thr Trp Arg Val Phe Cys Leu Leu Ala Val Ala Pro Gly
1               5                   10                  15 gcc cac agc cag gta cag ctg gtg cag tct ggg gga ggc atg gta gag      96
Ala His Ser Gln Val Gln Leu Val Gln Ser Gly Gly Gly Met Val Glu -continued

|  |  |
|---|---|
| act cag ccg ccc tca gtg tct gcg gcc cca gga cag aag gtc acc atc<br>Thr Gln Pro Pro Ser Val Ser Ala Ala Pro Gly Gln Lys Val Thr Ile<br>145                      150                      155                      160 | 528 |
| tcc tgc tct gga agc agc tcc aac att gga aat aat tat gtc tcc tgg<br>Ser Cys Ser Gly Ser Ser Ser Asn Ile Gly Asn Asn Tyr Val Ser Trp<br>                180                      185                      190 | 576 |
| tac gtt caa ctc cca gga aca gcc ccc aaa ctc ctc att tat gac aat<br>Tyr Val Gln Leu Pro Gly Thr Ala Pro Lys Leu Leu Ile Tyr Asp Asn<br>            195                      200                      205 | 624 |
| aat aag cga ttc tca gga gtt cct gac cga ttc tct ggc tcc aag tct<br>Asn Lys Arg Phe Ser Gly Val Pro Asp Arg Phe Ser Gly Ser Lys Ser<br>210                      215                      220 | 672 |
| ggc acg tca gcc acc ctg ggc atc acc ggg ctc cag act ggg gac gag<br>Gly Thr Ser Ala Thr Leu Gly Ile Thr Gly Leu Gln Thr Gly Asp Glu<br>225                      230                      235                      240 | 720 |
| gcc gat tat tac tgc gga gca tgg gat ggc agc ctg cgt gaa gcg gta<br>Ala Asp Tyr Tyr Cys Gly Ala Trp Asp Gly Ser Leu Arg Glu Ala Val<br>                245                      250                      255 | 768 |
| ttc ggc gga ggg acc aag gtc acc gtc cta ggt gcg gcc gca gtt gag<br>Phe Gly Gly Gly Thr Lys Val Thr Val Leu Gly Ala Ala Ala Val Glu<br>            260                      265                      270 | 816 |
| ctc gag gcg gcc gcg gat tac aaa gac gat gac gat aaa gaa ttc gga<br>Leu Glu Ala Ala Ala Asp Tyr Lys Asp Asp Asp Asp Lys Glu Phe Gly<br>275                      280                      285 | 864 |
| tca tct tct cga acc ccg agt gac aag cct gta gcc cat gtt gta gca<br>Ser Ser Ser Arg Thr Pro Ser Asp Lys Pro Val Ala His Val Val Ala<br>290                      295                      300 | 912 |
| aac cct caa gct gag ggg cag ctc cag tgg ctg aac cgc cgg gcc aat<br>Asn Pro Gln Ala Glu Gly Gln Leu Gln Trp Leu Asn Arg Arg Ala Asn<br>305                      310                      315                      320 | 960 |
| gcc ctc ctg gcc aat ggc gtg gag ctg aga gat aac cag ctg gtg gtg<br>Ala Leu Leu Ala Asn Gly Val Glu Leu Arg Asp Asn Gln Leu Val Val<br>                325                      330                      335 | 1008 |
| cca tca gag ggc ctg tac ctc atc tac tcc cag gtc ctc ttc aag ggc<br>Pro Ser Glu Gly Leu Tyr Leu Ile Tyr Ser Gln Val Leu Phe Lys Gly<br>            340                      345                      350 | 1056 |
| caa ggc tgc ccc tcc acc cat gtg ctc ctc acc cac acc atc agc cgc<br>Gln Gly Cys Pro Ser Thr His Val Leu Leu Thr His Thr Ile Ser Arg<br>            355                      360                      365 | 1104 |
| atc gcc gtc tcc tac cag acc aag gtc aac ctc ctc tct gcc atc aag<br>Ile Ala Val Ser Tyr Gln Thr Lys Val Asn Leu Leu Ser Ala Ile Lys<br>370                      375                      380 | 1152 |
| agc ccc tgc cag agg gag acc cca gag ggg gct gag gcc aag ccc tgg<br>Ser Pro Cys Gln Arg Glu Thr Pro Glu Gly Ala Glu Ala Lys Pro Trp<br>385                      390                      395                      400 | 1200 |
| tat gag ccc atc tat ctg gga ggg gtc ttc cag ctg gag aag ggt gac<br>Tyr Glu Pro Ile Tyr Leu Gly Gly Val Phe Gln Leu Glu Lys Gly Asp<br>                405                      410                      415 | 1248 |
| cga ctc agc gct gag atc aat cgg ccc gac tat ctc gac ttt gcc gag<br>Arg Leu Ser Ala Glu Ile Asn Arg Pro Asp Tyr Leu Asp Phe Ala Glu<br>            420                      425                      430 | 1296 |
| tct ggg cag gtc tac ttt ggg atc att gcc ctg ggt ggc ggt tct ggt<br>Ser Gly Gln Val Tyr Phe Gly Ile Ile Ala Leu Gly Gly Gly Ser Gly<br>            435                      440                      445 | 1344 |
| ggc ggt tct ggt ggc ggt tct ggt gga gga tca tca tct tct cga acc<br>Gly Gly Ser Gly Gly Gly Ser Gly Gly Gly Ser Ser Ser Ser Arg Thr<br>450                      455                      460 | 1392 |
| ccg agt gac aag cct gta gcc cat gtt gta gca aac cct caa gct gag | 1440 |

```
                Pro Ser Asp Lys Pro Val Ala His Val Val Ala Asn Pro Gln Ala Glu
                465                 470                 475                 480 ggg cag ctc cag tgg ctg aac cgc cgg gcc aat gcc ctc ctg gcc aat              1488
Gly Gln Leu Gln Trp Leu Asn Arg Arg Ala Asn Ala Leu Leu Ala Asn
                    485                 490                 495 ggc gtg gag ctg aga gat aac cag ctg gtg gtg cca tca gag ggc ctg              1536
Gly Val Glu Leu Arg Asp Asn Gln Leu Val Val Pro Ser Glu Gly Leu
            500                 505                 510 tac ctc atc tac tcc cag gtc ctc ttc aag ggc caa ggc tgc ccc tcc              1584
Tyr Leu Ile Tyr Ser Gln Val Leu Phe Lys Gly Gln Gly Cys Pro Ser
        515                 520                 525 acc cat gtg ctc ctc acc cac acc atc agc cgc atc gcc gtc tcc tac              1632
Thr His Val Leu Leu Thr His Thr Ile Ser Arg Ile Ala Val Ser Tyr
    530                 535                 540 cag acc aag gtc aac ctc ctc tct gcc atc aag agc ccc tgc cag agg              1680
Gln Thr Lys Val Asn Leu Leu Ser Ala Ile Lys Ser Pro Cys Gln Arg
545                 550                 555                 560 gag acc cca gag ggg gct gag gcc aag ccc tgg tat gag ccc atc tat              1728
Glu Thr Pro Glu Gly Ala Glu Ala Lys Pro Trp Tyr Glu Pro Ile Tyr
                565                 570                 575 ctg gga ggg gtc ttc cag ctg gag aag ggt gac cga ctc agc gct gag              1776
Leu Gly Gly Val Phe Gln Leu Glu Lys Gly Asp Arg Leu Ser Ala Glu
            580                 585                 590 atc aat cgg ccc gac tat ctc gac ttt gcc gag tct ggg cag gtc tac              1824
Ile Asn Arg Pro Asp Tyr Leu Asp Phe Ala Glu Ser Gly Gln Val Tyr
        595                 600                 605 ttt ggg atc att gcc ctg ggt ggc ggt tct ggt ggc ggt tct ggt ggc              1872
Phe Gly Ile Ile Ala Leu Gly Gly Gly Ser Gly Gly Gly Ser Gly Gly
    610                 615                 620 ggt tct ggt ggc gga tca tca tct tct cga acc ccg agt gac aag cct              1920
Gly Ser Gly Gly Gly Ser Ser Ser Ser Arg Thr Pro Ser Asp Lys Pro
625                 630                 635                 640 gta gcc cat gtt gta gca aac cct caa gct gag ggg cag ctc cag tgg              1968
Val Ala His Val Val Ala Asn Pro Gln Ala Glu Gly Gln Leu Gln Trp
                645                 650                 655 ctg aac cgc cgg gcc aat gcc ctc ctg gcc aat ggc gtg gag ctg aga              2016
Leu Asn Arg Arg Ala Asn Ala Leu Leu Ala Asn Gly Val Glu Leu Arg
            660                 665                 670 gat aac cag ctg gtg gtg cca tca gag ggc ctg tac ctc atc tac tcc              2064
Asp Asn Gln Leu Val Val Pro Ser Glu Gly Leu Tyr Leu Ile Tyr Ser
        675                 680                 685 cag gtc ctc ttc aag ggc caa ggc tgc ccc tcc acc cat gtg ctc ctc              2112
Gln Val Leu Phe Lys Gly Gln Gly Cys Pro Ser Thr His Val Leu Leu
    690                 695                 700 acc cac acc atc agc cgc atc gcc gtc tcc tac cag acc aag gtc aac              2160
Thr His Thr Ile Ser Arg Ile Ala Val Ser Tyr Gln Thr Lys Val Asn
705                 710                 715                 720 ctc ctc tct gcc atc aag agc ccc tgc cag agg gag acc cca gag ggg              2208
Leu Leu Ser Ala Ile Lys Ser Pro Cys Gln Arg Glu Thr Pro Glu Gly
                725                 730                 735 gct gag gcc aag ccc tgg tat gag ccc atc tat ctg gga ggg gtc ttc              2256
Ala Glu Ala Lys Pro Trp Tyr Glu Pro Ile Tyr Leu Gly Gly Val Phe
            740                 745                 750 cag ctg gag aag ggt gac cga ctc agc gct gag atc aat cgg ccc gac              2304
Gln Leu Glu Lys Gly Asp Arg Leu Ser Ala Glu Ile Asn Arg Pro Asp
        755                 760                 765 tat ctc gac ttt gcc gag tct ggg cag gtc tac ttt ggg atc att gcc              2352
Tyr Leu Asp Phe Ala Glu Ser Gly Gln Val Tyr Phe Gly Ile Ile Ala
    770                 775                 780
```

```
ctg tga                                                    2358
Leu
785
```

<210> SEQ ID NO 40
<211> LENGTH: 785
<212> TYPE: PRT
<213> ORGANISM: Artificial Sequence
<220> FEATURE:
<223> OTHER INFORMATION: Description of Artificial Sequence: TNF-AMAIZe peptide sequence

```
                340              345              350
Gln Gly Cys Pro Ser Thr His Val Leu Leu Thr His Thr Ile Ser Arg
            355              360              365
Ile Ala Val Ser Tyr Gln Thr Lys Val Asn Leu Leu Ser Ala Ile Lys
        370              375              380
Ser Pro Cys Gln Arg Glu Thr Pro Glu Gly Ala Glu Ala Lys Pro Trp
385              390              395              400
Tyr Glu Pro Ile Tyr Leu Gly Gly Val Phe Gln Leu Glu Lys Gly Asp
                405              410              415
Arg Leu Ser Ala Glu Ile Asn Arg Pro Asp Tyr Leu Asp Phe Ala Glu
            420              425              430
Ser Gly Gln Val Tyr Phe Gly Ile Ile Ala Leu Gly Gly Ser Gly
        435              440              445
Gly Gly Ser Gly Gly Gly Ser Gly Gly Gly Ser Ser Ser Arg Thr
    450              455              460
Pro Ser Asp Lys Pro Val Ala His Val Val Ala Asn Pro Gln Ala Glu
465              470              475              480
Gly Gln Leu Gln Trp Leu Asn Arg Arg Ala Asn Ala Leu Leu Ala Asn
                485              490              495
Gly Val Glu Leu Arg Asp Asn Gln Leu Val Val Pro Ser Glu Gly Leu
            500              505              510
Tyr Leu Ile Tyr Ser Gln Val Leu Phe Lys Gly Gln Gly Cys Pro Ser
        515              520              525
Thr His Val Leu Leu Thr His Thr Ile Ser Arg Ile Ala Val Ser Tyr
    530              535              540
Gln Thr Lys Val Asn Leu Leu Ser Ala Ile Lys Ser Pro Cys Gln Arg
545              550              555              560
Glu Thr Pro Glu Gly Ala Glu Ala Lys Pro Trp Tyr Glu Pro Ile Tyr
                565              570              575
Leu Gly Gly Val Phe Gln Leu Glu Lys Gly Asp Arg Leu Ser Ala Glu
            580              585              590
Ile Asn Arg Pro Asp Tyr Leu Asp Phe Ala Glu Ser Gly Gln Val Tyr
        595              600              605
Phe Gly Ile Ile Ala Leu Gly Gly Ser Gly Gly Gly Ser Gly Gly
    610              615              620
Gly Ser Gly Gly Gly Ser Ser Ser Arg Thr Pro Ser Asp Lys Pro
625              630              635              640
Val Ala His Val Val Ala Asn Pro Gln Ala Glu Gly Gln Leu Gln Trp
                645              650              655
Leu Asn Arg Arg Ala Asn Ala Leu Leu Ala Asn Gly Val Glu Leu Arg
            660              665              670
Asp Asn Gln Leu Val Val Pro Ser Glu Gly Leu Tyr Leu Ile Tyr Ser
        675              680              685
Gln Val Leu Phe Lys Gly Gln Gly Cys Pro Ser Thr His Val Leu Leu
    690              695              700
Thr His Thr Ile Ser Arg Ile Ala Val Ser Tyr Gln Thr Lys Val Asn
705              710              715              720
Leu Leu Ser Ala Ile Lys Ser Pro Cys Gln Arg Glu Thr Pro Glu Gly
                725              730              735
Ala Glu Ala Lys Pro Trp Tyr Glu Pro Ile Tyr Leu Gly Gly Val Phe
            740              745              750
Gln Leu Glu Lys Gly Asp Arg Leu Ser Ala Glu Ile Asn Arg Pro Asp
        755              760              765
```

```
Tyr Leu Asp Phe Ala Glu Ser Gly Gln Val Tyr Phe Gly Ile Ile Ala
    770                 775                 780
Leu
785

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Peptide
      linker sequence

<400> SEQUENCE: 41

Gly Gly Gly Ser
1
```

RECOMBINANT POLYPEPTIDES OF THE MEMBERS OF THE TNF LIGAND FAMILY AND USE THEREOF

This application is the National Phase of International Application PCT/EP2005/003158 filed Mar. 24, 2005 which designated the U.S. and that International Application was published under PCT Article 21(2) in English, and claims priority to German Application Serial No. 10 2004 014 983.6, filed Mar. 26, 2004

The present invention relates to polypeptides, which comprise at least three monomers of a member of the TNF ligand family as component A and at least two peptide linkers as component B, whereby the peptide linkers link the monomers of the member of the TNF ligand family to one another. Furthermore, the present invention relates to the use of these polypeptides for the treatment of diseases and for the preparation of a medication or vaccine. Moreover, the invention relates to methods for preparing and isolating these polypeptides and to the nucleic acids coding for the polypeptides, to vectors containing these nucleic acids, to host cells transfected with these vectors, and pharmaceutical compositions, containing these objects of the invention. Finally, the invention relates to methods for the extracorporeal manipulation, depletion, and/or removal of components present in body fluids, e.g., by apheresis.

Members of the TNF ligand family are proinflammatory cytokines. Cytokines in general and members of the TNF ligand family in particular play a important role in the stimulation and coordination of the innate immune system and the humoral (antibody-mediated) immune response, the induction of apoptosis, synthesis of bone, formation of anlagen for hair growth, tooth growth, and sweat gland development, the anlage for lymph nodes, and many more (Aggarwal, B. B. (2003), Nat. Rev. Immunol. 3, 745-756). Defective regulation of members of the TNF ligand family, on the contrary, can lead to numerous pathological conditions. These include, for example, septic shock, autoimmune diseases, such as rheumatoid arthritis, or neurodegenerative diseases. The tumor necrosis factor (TNF) is the eponymous and arguably the most important member of this large cytokine family.

Members of the TNF ligand family exert their action in their biologically active form as homotrimers (Banner, D. W. et al., (1993) Cell 73, 431-445). Many trimeric structures and also aggregations of a higher order (e.g., oligomers or multimers of trimers) of proteins are encountered in nature. Examples are the cartilage matrix protein (CMP), a connective tissue protein (Beck et al. (1996), J Mol Biol 256, 909-923), proteins from the collagen family, such as the Clq family, which includes Clq, collagen α1 (X), α2 (VII), the hibernation protein, ACRP30, the inner ear protein, cellebrin [sic, cerebellin ?], and multimerin (Kishore and Reid, (1999), Immunopharmacol. 42, 15-21), and proteins of the collectin family, such as the lung surfactant protein A (SP-A) and the mannose binding protein (MBP) (Epstein et al. (1996), Current Opinion in Immunology, Vol 8 No. 1, 29-35).

The assembly of proteins into a trimer occurs at the surfaces of these proteins, which trimerize in solution due to interactions, such as hydrophobic interactions, hydrogen bridge formation, covalent bonds (e.g., disulfide bridges), and/or Coulomb forces, but also due to structural motifs, i.e., characteristic amino acid sequences that bring about the formation of intermolecular supersecondary structures. In the case of members of the TNF ligand family, the three monomers in the homotrimeric structure are held together noncovalently by hydrophobic bonds. In their activated form, they in turn activate their opposite members of the TNF receptor family, which have no enzymatic activity as such. For example, TNF as a member of the TNF ligand family binds to the two membrane receptors TNFR1 and TNFR2 and mediates the trimerization of receptors or the activation of receptors already in trimer form but signal-inactive. The complex formation of receptors initiates a signal cascade, which is accompanied, inter alia, by an association of cytoplasmic adapter proteins (Wajant, H. et al (2003), Cell Death Differ, 10, 45-65). The trimeric structure of TNFR1 and TNFR2 forms in such a way that the receptors each bind in the interspace between two of the three TNF monomers of the TNF homotrimers (Banner et al. (1993), supra). It clear from this that both TNF and the other members of the TNF ligand family are biologically active only in their structure as homotrimers.

Because of their function, the members of the TNF ligand family or their membrane receptors can be used variously for the treatment of numerous diseases, such as infectious and inflammatory diseases, metabolic diseases, diseases based on defective regulation of apoptosis, neurodegenerative diseases, and many other diseases. Their use in the treatment of cancer diseases plays an especially important role, because members of the TNF ligand family are usually substances exhibiting antitumor activity. To be noted in particular in this regard are TNF itself (Eggernont, A. M. and ten Hagen, T. L. (2003), Curr. Oncol. Rep. 5, 79-80), TRAIL (TNF-related apoptosis-inducing ligand), also called Apo 2L (Weley et al. (1995), Immunity 6: 673-682; Petti et al. (1996) J Biol Chem 271: 12687-12689), and FasL. In vivo studies, however, showed severe systemic adverse effects of TNF and agonists of the Fas receptor and in vitro studies also indicate similar toxic effects for certain TRAIL preparations (Jo et al. (2000) Nat Med 6: 564-567, Ichikawa et al. (2001) Nat Med 7: 954-960; Ogasawara et al. (1993) Nature 364: 806-809). For example, agonistic antibodies to Fas, the FasL receptor, exhibited an extremely hepatotoxic effect (Ogasawara et al. (1993), supra). For this reason, in the case of Fas-activating ligands/agonists, clinical use has been ruled out thus far for reasons of safety. Because of the considerable importance of TNF, TRAIL, FasL, and other TNF ligand family members in this field and the adverse effects associated with their administration in the form of clinical systemic dosing, however, several approaches were pursued to minimize these adverse effects. (Eggermont, A. M. and ten Hagen, T. L. (2003), Curr. Oncol. Rep. 5, 79-80.)

Thus, for example, WO 02/22680 describes fusion proteins, which enable a directed and tissue-specific or cell-specific effect of cytokines by fusion of the cytokine with an antigen-binding antibody. The result achieved in this way is that the cytokines exert no effect on tissues or cells not coming into contact with these fusion proteins and that adverse effects on these tissues or cells are reduced.

DE 102 47 755 discloses an antibody-independent system, which also enables a directed and tissue-specific or cell-specific action of the cytokines. This refers to fusion proteins, in which the activation of the protein segment, contained therein, with biological function occurs via its binding to a cell-surface molecule binding domain, which represents another protein segment of the fusion protein. Apart from a reduction of adverse effects on non-target tissue, it is also possible to use this system advantageously for cell-surface molecules on the target cells, for which no antibodies or antibodies with a too low specificity are available.

Apart from the noted adverse effects, however, it is also very problematic that the active homotrimers of the members of the TNF ligand family dissociate in dilutions, and this means in physiologically meaningful concentrations as well.

This dissociation is in fact basically reversible, but the protein rapidly loses its bioactivity, because it denatures. It is assumed that this denaturation occurs via the step of unstable monomers (Smith, R. A. and Baglioni, C. (1987), J. Biol. Chem. 262, 6951-6954; Narhi, L. O. and Arakawa, T. (1987), Biochem. Biophys. Res. Commun. 147, 740-746).

Because of similar observations with TRAIL, which is especially labile, efforts were made to achieve a stability of the protein by addition of a leucine zipper as a trimerization module (Cha, S. S. et al., (1999), Immunity 11, 253-261). In its native state, TRAIL is stabilized by a zinc ion, which sits in the center of the trimeric ligand, and which is coordinated by cysteine residues (Hymowitz, S. G. et al. (2000), Biochemistry 39, 633-640). It can be a disadvantage here, however, that the addition of the leucine zipper not only achieves increased stability, but could also have a detrimental effect on other properties, e.g., structural properties such as structural changes, activity rates, or physiological properties.

There is a need, therefore, to increase the stability of active cytokines, particularly members of the TNF ligand family, without detrimentally affecting their native properties by a change in their structure, and without these substances exhibiting potent cytotoxic or other adverse effects in therapeutic applications.

No systems that achieve this are known in the related art, i.e., by which the members of the TNF ligand family are provided in an active and stable form, said members which are suitable for therapeutic application without the aforementioned disadvantages by themselves or as biologically active components of complex fusion proteins.

SUMMARY OF THE INVENTION

The object of the present invention is to provide a system by which the stability of the members of the TNF ligand family is increased.

This object is attained by the embodiments of the present invention as characterized in the claims. This object is attained in particular by the subject of claim 1, namely, by the provision of a polypeptide, which comprises at least three components A and at least two components B, whereby each component A is a monomer of a member of the TNF ligand family or a functional fragment, and/or a functional variant thereof and each component B is a peptide linker.

The present invention is based on the knowledge that naturally occurring soluble cytokine members of the TNF ligand family exhibit their full bioactivity only as homotrimers, but, on the other hand, tend to denature via dissociation of their monomers.

It is therefore imperative to prevent this dissociation of the homotrimers into monomers. This is achieved according to the invention in that at least three monomers of a member of the TNF ligand family, particularly TNF, were bound covalently to one another via their C terminals and N terminals by means of short peptide linkers to form a "single-chain" molecule ("sc" hereafter), particularly to form an scTNF. According to the invention, therefore, the entire molecule (at least three monomers of a member of the TNF ligand family with the two peptide linkers) consists of a single protein strand, so that dissociation into monomers can no longer occur. It was demonstrated according to the invention that such molecules of the invention exhibit very low loss of their bioactivity in comparison to their corresponding soluble wild-type members of the TNF ligand family. In contrast, it was not only demonstrated according to the invention that the polypeptides of the present invention have the same (qualitative) activities as their corresponding soluble wild-type member of the TNF ligand family, but also that because of their considerably higher stability they still exhibit bioactivities at a time when the soluble wild-type member of the TNF ligand family has already lost its activity, i.e., is disassociated or denatured (reference on this point is made to the various stability tests described hereafter, which are described in the examples and in the figures).

A "soluble wild-type member of the TNF ligand family" is to be understood as a soluble extracellular segment of a membrane-associated member of the TNF ligand family. The expressions "wild type", "wt", "soluble," and "s" (for "soluble") are used hereafter synonymously with the term "soluble wild type." These can be in particular soluble wild-type TNF (as a member of the TNF ligand family), for which accordingly the synonymous terms "wild-type TNF," "wtTNF", soluble TNF, and "sTNF" are used hereafter.

A component A within the meaning of the invention is a monomer of a member of the TNF ligand family or a functional fragment or a functional variant thereof. A "monomer" is to be understood as the smallest protein unit or polypeptide unit that can be separated from an oligomeric protein without breaking the covalent bonds.

A polypeptide or a component A or a fragment or a variant thereof is functional within the meaning of the invention, provided it exhibits its biological activity or function, particularly its binding property to an interaction partner, e.g., a membrane-associated receptor, and also its trimerization property. In the case of functional fragments and the functional variants of the invention, these biological functions can in fact be changed, e.g., with respect to their specificity or selectivity, but with retention of the basic biological function.

Numerous methods for measuring the biological activity of a protein, polypeptide, or molecule are known from the related art, for example, protein assays, which use labeled substrates, substrate analyses by chromatographic methods, such as HPLC or thin-layer chromatography, spectrophotometric methods, etc. (see, e.g., Maniatis et al. (2001) Molecular Cloning: A Laboratory Manual, Cold Spring Harbor Laboratory Press, Cold Spring Harbor, N.Y.).

A fragment within the meaning of the invention is to be understood as both a fragment of a monomer of a member of the TNF ligand family and a fragment of a polypeptide or protein of the present invention. These can be N-terminally, C-terminally, or intrasequentially shortened amino acid sequences of the monomer, polypeptide, or protein. In particular, the intrasequential shortenings of the polypeptide or protein may be shortenings of the sequence of one or more of the three monomers, which in turn can occur N-terminally, C-terminally, or intrasequentially.

In an especially preferred embodiment of the invention, the fragment of a monomer represents its extracellular domain, which corresponds to the entire extracellular domain of the soluble wild-type member of the TNF ligand family or a segment thereof. In particular, the fragment represents a monomer of its extracellular domain, which corresponds either to the soluble wild-type TNF (amino acids 77-233) or the entire extracellular domain (amino acids 53-233).

The preparation of such fragments of the invention is well known from the related art and can be performed by a person skilled in the art with use of standard methods (see, e.g., Maniatis et al. (2001), Molecular Cloning: Laboratory Manual, Cold Spring Harbor Laboratory Press). In general, the fragments of the monomers, polypeptides, or proteins can be prepared by modification of the DNA sequence, coding for the native monomer, polypeptide, or protein, followed by a transformation of this DNA sequence in a suitable host, and expression of this modified DNA sequence, provided that the modification of the DNA does not disrupt the functional activities of the monomer, polypeptide, or protein.

The identification of a fragment of the invention can occur either by testing its functionality by measuring its biological activity, as described above, or based on a sequencing of the fragment and a subsequent comparison of the obtained sequence with the native sequence. The sequencing can occur using standard methods, which are well-known and numerous in the related art.

In particular, monomers, polypeptides, or proteins, or fragments thereof that have sequence differences relative to the corresponding native sequences are designated as variants of biologically active monomers, polypeptides, or proteins, or fragments thereof, or a component A within the meaning of the invention. These sequence deviations can be one or more insertion(s), deletion(s), and/or substitution(s) of amino acids, whereby there is a sequence homology of at least 60%, preferably 70%, more preferably 80%, also more preferably 85%, even more preferably 90%, and most preferably 97%.

To determine the percentage identity of two nucleic acid or amino acid sequences, the sequences can be aligned in order to be compared subsequently with one another. To this end, e.g., gaps can be introduced into the sequence of the first amino acid or nucleic acid sequence and the amino acids or nucleotides compared at the corresponding position of the second amino acid or nucleic acid sequence. If a position in the first amino acid sequence is occupied by the same amino acid or the same nucleotide, as is the case at a position in the second sequence, then both sequences are identical at this position. The percentage identity between two sequences is a function of the number of identical positions divided by the sequences.

The determination of the percentage identity of two sequences can be performed using a mathematical algorithm. A preferred, but not limiting example of a mathematical algorithm, which can be used for comparing two sequences, is the algorithm of Karlin et al. (1993), PNAS USA, 90:5873-5877. This type of algorithm is integrated into the NBLAST program, which can identify the sequences that have a desired identity to the sequences of the present invention. To obtain a gapped alignment, as described above, the "gapped BLAST" program can be used, as described in Altschul et al. (1997), Nucleic Acids Res, 25:3389-3402.

Biologically active, therefore functional, variants of monomers, polypeptides, or proteins, or fragments thereof within the meaning of the invention can preferably have selective receptor binding properties, whereby the variant can be optimized, e.g., with respect to their specific bioactivity or other properties, particularly their stability.

The term variants includes particularly amino acid sequences with conservative substitution compared with physiological sequences. Conservative substitutions are substitutions in which amino acids stemming from the same class are exchanged. In particular, there are amino acids with aliphatic side chains, positively or negatively charged side chains, aromatic groups in the side chains, or amino acids whose side chains may contain hydrogen bridges, for example, side chains with a hydroxy function. This means that, for example, an amino acid with a polar side chain is replaced by another amino acid with a likewise polar side chain or, for example, an amino acid characterized by a hydrophobic side chain is substituted by another amino acid with a likewise hydrophobic side chain (e.g., serine (threonine) by threonine (serine) or leucine (isoleucine) by isoleucine (leucine)). Insertions and substitutions are possible particularly at sequence positions that cause no change in the three-dimensional structure or affect the binding region. A change in a three-dimensional structure by insertion(s) or deletion(s) can be easily checked, for example, with the use of CD spectra (circular dichroism spectra) (Urry, 1985, Absorption, Circular Dichroism and ORD of Polypeptides, in: Modern Physical Methods in Biochemistry, Neuberger et al. (eds.), Elsevier, Amsterdam).

Suitable methods for the preparation of variants, e.g., of monomers, polypeptides, or proteins, or fragments thereof with amino acid sequences that have substitutions compared with the native sequences, are disclosed, for example, in the publications U.S. Pat. No. 4,737,462, U.S. Pat. No. 4,588,585, U.S. Pat. No. 4,959,314, U.S. Pat. No. 5,116,943, U.S. Pat. No. 4,879,111, and U.S. Pat. No. 5,017,691. The preparation of variants in general is also described particularly by Maniatis et al, (2001), Molecular Cloning: A Laboratory Manual, Cold Spring Harbor Laboratory Press). In this case, codons can be omitted, added, or replaced. Variants can also be particularly proteins or polypeptides that are stabilized to escape physiological degradation, for example, by stabilization of the protein backbone by substitution of amide-like bonds, for example, also by the use of β-amino acids.

Variants within the meaning of the invention can also be prepared by introducing changes into the nucleic acids, coding for the variants, such as, for example, insertions, deletions, and/or substitutions in one or more nucleotides. Numerous methods for this type of changes in nucleic acid sequences are known in the related art. One of the most frequently used techniques is oligonucleotide-directed, site-specific mutagenesis (see Comack B., Current Protocols in Molecular Biology, 8.01-8.5.9, Ausubel F. et al., 1991 edition). An oligonucleotide whose sequence has a specific mutation is synthesized in this technique. This oligonucleotide is then hybridized with a template that contains the wild-type nucleic acid sequence. A single-stranded template is used preferentially in this technique. After annealing of oligonucleotide and template, a DNA-dependent DNA polymerase is used to synthesize the second strand of the oligonucleotide, which is complementary to the template-DNA strand. A heteroduplex molecule is obtained as a result, which contains a mispairing formed due to the aforementioned mutation in the oligonucleotide. The oligonucleotide sequence is then introduced into a suitable plasmid, this is introduced into a host cell, and the oligonucleotide DNA is replicated in this host cell. This technique produces nucleic acid sequences with selective changes (mutations), which can be used for preparing variants according to the invention.

Components A covered by the polypeptides of the invention can be identical or different; i.e., components A can be monomers of the same member of the TNF ligand family or different members of the TNF ligand family. For example, three different components A can be three monomers of three different members of the TNF ligand family or two monomers of the same member of the TNF ligand family and one monomer of another member of the TNF ligand family. This applies accordingly to more than three components A. For example, a polypeptide of the invention can contain 4, 5, 6, or more components A, which form a tetramer, pentamer, hexamer, etc. It is also especially preferred for the polypeptide of the invention to contain an integer multiple of a trimer, as previously described, of component A, e.g., two, three, four, or more trimers arranged one after another. Components A present in the polypeptides of the invention can be separated by linkers from one another (see below). If, as described above, two, three, four, or more trimers of components A are arranged one after another, the linkers binding the different trimers to one another can be longer, if necessary, than the linkers binding components A in a single trimer to one another.

Components A of the invention can stem from the same or different organisms. These can be vertebrates, particularly mammals, for example, the mouse, rat, pig, and primarily humans.

In a preferred embodiment of the invention, components A of the polypeptide of the invention are in each case a monomer of one of the members of the TNF ligand family or a functional fragment or a functional variant thereof, selected from the group consisting of FasL (GenBank Accession No. NM_000639), TRAIL (TNF-Related Apoptosis-Inducing Ligand; GenBank Accession No. NM_003810), also called Apo2L, TNF (tumor necrosis factor; GenBank Accession No. NM_000594), LT alpha (GenBank Accession No. NM_000595), lymphotoxin beta (GenBank Accession No. NM 002341), NGF (GenBank Accession No. NM_002506), CD30L (CD153; GenBank Accession No. NM_001244), CD40L (CD 154; GenBank Accession No. NM_00074), OX40L (GenBank Accession No. NM_003326), RANKL (GenBank Accession No. NM_003701), TWEAKL (GenBank Accession No. NM_003809), LTalpha, LTbeta, LIGHT (GenBank Accession No. NM_003807), CD27L (GenBank Accession No. NM_001252), 4-1BBL (GenBank Accession No. NM_003811), GITRL (GenBank Accession No. NM_005092), APRIL (GenBank Accession No. NM_172089), EDA (GenBank Accession No. NM_001399), VEGI (GenBank Accession No. NM_005118), and BAFF (GenBank Accession No. NM_006573).

In an especially preferred embodiment, component A, as defined above, of the polypeptide of the invention is a monomer of one of the members of the TNF ligand family, which is resistant to the processing enzyme TACE. TACE is a member of the ADAM protease family and represents the physiological TNF-specific processing enzyme of TNF found naturally in the cell membrane. TNF is typically cleaved from the cell membrane and released into the environment. A TACE-resistant component A of the invention preferably lacks the Ala-Val cleavage site (e.g., AA 76-77 in scTNF according to the SWISS-PROT nomenclature for human TNF, No. P)1375). The cleavage site can be removed in this case according to the invention by deletion of one or both relevant amino acids Ala or Val. Alternatively or in addition, according to the invention, the recognition sequence for TACE (e.g., AA 77-88 in scTNF according to the SWISS-PROT nomenclature for human TNF, No. PO1375) may be totally or partially deleted. This occurs preferably by deletion of two, three, four, or more amino acids, for example, all amino acids of the TACE recognition sequence. For scTNF, for example, the TACE-resistant sequence is in the region of amino acids 89-233 (AA 89-233) of scTNF according to the SWISS-PROT nomenclature for human TNF, No. PO1375. One such deletion in component A prevents a potential cleavage of component A, e.g., scTNF, by TACE near the linkage sites of components A in the area of the linkers (component B, see below), and thereby increases the in vivo stability of the polypeptides of the invention. If necessary, the shortening of the sequence, arising due to the deletion, can be compensated by an appropriate lengthening of the linkers. The deletion of the component A sequence, described as an example for scTNF, can be used for each of the aforementioned components A. If the TACE sequence is not to be removed or to be only partially removed, care must be taken preferably that during use of additional components B or C (see below) in the polypeptides of the invention, the TACE recognition sequence and the TACE cleavage site are not restored.

In another especially preferred embodiment, components A of the polypeptide of the invention, as defined above, are modified in such a way that the polypeptides of the invention can couple covalently to surfaces. This coupling occurs preferably to planar surfaces or to spherical particles, such as, e.g., to magnetic particles (magnetic beads), or to nanoparticles/niicroparticles, preferably as a cell-mimetic, therapeutic reagent with properties similar to membrane-bound TNF. For coupling, a coupling group, preferably the SH group of a cysteine residue, is introduced in the N-terminal region of at least one component A of the polypeptide of the invention. (Other preferred coupling groups of the invention are described further below). This can occur especially preferably by the introduction of a cysteine residue in the form of an addition and/or substitution at the desired position. The coupling group can occur at any position of the N-terminal region of component A, preferably near the N terminus. Especially preferably, the coupling group is located in a region of the first 1-15 N-terminal amino acids, and more greatly preferred in a region of the first 1-10 N-terminal amino acids. For example, the modification in a prokaryotically expressed scTNF can be introduced after an initial methionine (position 2) of the amino acid sequence or in a eukaryotically expressed scTNF directly after the cleaved leader sequence; these therefore represent the N-terminal amino acids of component A. Alternatively, in a tag used according to the invention, for example, a His tag, a Flag tag (see, e.g., FIG. 18), a coupling group is introduced according to the invention, e.g., resulting in a CysHis tag with a cysteine at amino acid position 9. Another alternative consists of the introduction of a coupling group in one or both components B (linkers) of the polypeptide of the invention.

Preferably, in a polypeptide of the invention, only the component A situated at the N terminus or the tag situated farther N-terminally is provided/modified with a coupling group as described above. In another embodiment, in the case of a polypeptide of the invention, which contains 3 components A, for example, 2 or 3 of components A modified in each case with a coupling group, so that the entire molecule (the polypeptide of the invention) can be coupled via 2 or 3 covalent bonds to a matrix suitable therefor. The coupling of the polypeptide of the invention via one or more coupling groups of all components A of a polypeptide of the invention preferably does not negatively impact the function of the individual components A, e.g., of TNF, but rather enables improvement of the immobilization, for example, of scTNF, on the surface and/or particle. As previously stated, e.g., in scTNF and also in scFasL and scTRAIL or other members of the TNF family in the sc form, each of polypeptides of the invention contains preferably the subunits necessary for the biological function (components A) in a functionally relevant arrangement. As taught by the invention, it is possible to produce surfaces or particles with, e.g., coupled TNF homotrimers or heterotrimers or -multimers, by coupling of a polypeptide of the invention to a surface/particle. The coupled TNF homotrimers or heterotrimers or -multimers are immobilized stably and bioactively on these surfaces/particles. The functionally relevant trimer state of components A is stabilized by components B by the single-chain principle of the invention; this assures that after covalent coupling to a surface/particle, dissociation of individual components A is ruled out and therefore loss of biological activity is prevented.

A preferred property of this type of polypeptide coupled to surfaces or particles according to the invention is their biomimetic activity, which corresponds to that of the natural, membrane-associated ligands of the TNF family. For example, an immobilized scTNF of the invention achieves a high affinity for TNFR2 and thereby a high signal capacity.

Polypeptides of the invention, which contain components A modified with a coupling group, as described above, and become/are coupled to a surface and/or particle, as taught by the invention, can be used for detection, as well as for manipulation, depletion, and/or removal of binding partners of members of the TNF ligand family, as well as compounds associated therewith. Of paramount interest thereby are methods for the extracorporeal manipulation, depletion, and/or removal of components present in body fluids, e.g., by apheresis.

The following statements on the subjects of the invention relate particularly to the TNF ligand family member TNF, but they can be applied to all other members of the TNF ligand family.

The polypeptides of the present invention comprise, apart from the described components A (monomers of at least one member of the TNF ligand family), at least two components B, whereby component B has the property of a peptide linker.

Any peptide sequence expressible in a biological system is conceivable as a peptide linker within the meaning of the invention. In the polypeptide constructs of the invention, peptide linkers turned out to be, for example, a flexible compound, which, however, preferably does not negatively influence the intrinsic trimerization properties of the particular member of the TNF ligand family. Preferably, linkers are chosen with properties, particularly flexibility and length, that are capable of stabilizing the spontaneously formed homotrimers of these specific ligands (derivatives).

In a preferred embodiment of the invention, component B accordingly is a peptide linker consisting of 2 to 30, preferably between 4 and 16, and especially preferably between 4 and 12 amino acids, which preferably contain repetitive glycine-serine structures, very preferably Gly-Gly-Gly-Ser modules (GGGS modules) SEQ. ID NO: 41) in a repetitive arrangement.

Preferably, the peptide linkers of the invention are therefore peptide linkers rich in glycine (G); i.e., the amino acid sequence of a peptide linker has a high proportion of glycine, preferably from 60 to 80%, especially preferably 75%.

In especially preferred embodiments of the invention, the peptide linker (component B) comprises the amino acid sequence GGGSGGGSGGGS, also called (GGGS)$_3$ (SEQ. ID NO: 2) or L$_{short}$, or the amino acid sequence GGGSGGGSGGGSGGS [sic], also called (GGGS)$_4$ (SEQ. ID NO: 3) or L$_{long}$. The peptide linkers according to the invention are designated, inter alia, as L1 and L2, so that designations such as L1$_{short}$, L2$_{short}$, L1$_{long}$, and/or L2$_{long}$ result. It is possible to use two different linkers to stabilize a trimer molecule.

Preferably, the peptide linkers according to the invention, therefore components B, in each case link together two of the at least three components A. This linkage occurs covalently via the C terminus of a component A and the N terminus of another component A. According to the invention, the polypeptide represents a single-chain molecule (also called an sc molecule). This means that all components A and components B, which comprise the polypeptide of the invention, are located on a single polypeptide strand or protein strand.

In a preferred embodiment of the invention, components A and components B form a trimeric protein structure. Preferably, this is a homotrimeric protein structure, but the invention also comprises heterotrimeric protein structures.

The formation of this trimeric protein structure is preferably effected by component B and/or enhanced by it. Because component B, which leads to trimerization, or component B, which enhances trimerization, of the polypeptide of the invention substantially should not form any higher aggregates, component B should typically not have any cysteine residues, which can form an intermolecular disulfide bridge. Preferably, component B in a polypeptide of the invention therefore has no cysteine residue or only such cysteine residues, which have an intramolecular disulfide bridge, therefore in the polypeptide itself of the invention, in order to avoid the formation of a covalent bond with the at least one cysteine residue of a fusion protein of another trimer under oxidizing conditions.

The sequences of native polypeptides or fragments of these native polypeptides, which are used as peptide linkers of the invention, can also be present in the form of biologically active functional variants of the same within the meaning of this invention and according to the above definition.

Components B of the invention can be identical or different naturally occurring peptide sequences. They can stem from the same or different organisms. The organisms can be vertebrates, particularly mammals, for example, the mouse, rat, pig, and primarily humans.

The polypeptide of the invention can have additional sequence segments apart from components A and B. Preferred in this regard are so-called tag sequences, for example, at least one Flag tag, therefore the amino acid sequence DYKDDDDK (SEQ. ID NO: 1), and/or, for example, at least one His tag (containing several consecutive histidines, for example, at least 5) and/or other tag or antigen sequences. An especially preferred additional sequence segment is a leader peptide sequence. Preferably, this leader peptide sequence represents a signal for the secretion of the polypeptide or protein in eukaryotic cells. This leader peptide sequence is preferably located N-terminally.

In another embodiment of the invention, a polypeptide of the invention comprises another component C, whereby this component is characterized by a specific interaction with a complementary cell surface molecule ("antigen"). The principle of action of the polypeptide constructs of the invention, such as, for example, constructs of the invention with the apoptosis inducer TRAIL or FasL as component A is particularly applicable for all members of the TNF ligand family that are active as a membrane molecule for specific receptors exclusively or to a particularly good extent. Apart from TRAIL (TNFSF10), FasL (TNFSF6), and TNF (TNFSF2), these include, for example, also the immunomodulators CD40L (TNFSF5) and CD30L (TNFSF8). Component C thereby has a "targeting" function. Accordingly, component C is an antibody fragment, preferably a single-chain antibody fragment, the so-called scFv, or an antibody derivative which recognizes a specific target molecule on the cell surface. In another embodiment, component C is not an antibody-associated protein or peptide, which, in analogy to an antibody-antigen interaction or a receptor-ligand interaction, also selectively recognizes a specific target molecule on the cell surface. In an especially preferred embodiment, the present invention comprises a polypeptide of the invention, as described above, as component A at least one member of the scTNF family, as defined above, e.g., scTNF, and as component C an antibody fragment, as described above, e.g., scFv. Smaller polypeptides of the invention are formed thereby with a "targeting domain" in each case. Such smaller polypeptides of the invention are advantageously less susceptible to, e.g., aggregation.

Preferably, component C is an antigen-binding antibody fragment or an antigen-binding antibody derivative from a mammal, particularly of murine or human origin, or a humanized antibody fragment or a humanized antibody derivative, e.g., of mammalian origin. In the case of derivatization and/or humanizing, component C typically consists of a single-chain Fv derivative, prepared according to the related art, murine component C, humanized by CDR grafting, or component C is of completely human origin which was transformed accordingly to an scFv derivative.

In another preferred embodiment, component C is a protein ligand or peptide ligand, which as a monomer enters into a specific bond at a membrane receptor.

In another preferred embodiment, component C is a protein or peptide with specificity for cell surface molecules, which is particularly a cytokine receptor, a growth factor receptor, an integrin, or cell adhesion molecule. It is especially preferred that it is a cytokine receptor, which is selected from the group of the TNFR gene family.

Component C of a polypeptide of the invention preferably exhibits specificity for an antigen selectively or predominantly expressed in tumor tissue. This type of tumor antigen can be expressed in general in the malignant cells themselves or also in the nonmalignant part of the tumor, the stromal cells or the tumor endothelium. Such antigens of nonmalignant tissue parts of a solid tumor (carcinoma) are genetically invariant, on the one hand, but on the other, they occur in the most different tumor entities and are thereby universal tumor markers. Examples of such ligands for tumor association, against which a component C of the polypeptide of the invention can be directed, are the VEGFR or the VEGFR/VEGF complex and the integrin $a_v\beta_2$ and the vibronectin isoform $\beta$ Fn as largely selective target structures of the tumor endothelium and the fibroblast activation protein (as a selective marker of the tumor stroma). All aforementioned examples can be effectively covered by specific scFv, which is why such scFv ("single-chain Fv") are especially suitable as component C of a polypeptide of the invention. Galectin as well is regarded hereby as a tumor marker, against which component C is directed.

Accordingly, antibody fragments in different antibodies formats, for example, scFv, particularly scFv40, are particularly preferred as component C.

In another embodiment of the present invention, the polypeptide via its component C recognizes as a specific target molecule a cell membrane-associated receptor of a member of the TNF ligand family, preferably different from the TNF ligand family member of component A. Examples, which do not represent a definitive enumeration of such possible ligands, are TNFSF1 (LTalpha), TNFSF2 (TNF), TNFSF3 (LTbeta), TNFSF4 (OX40L), TNFSF5 (CD40L), TNFSF6 (FasL), TNFSF7 (CD27L), TNFSF8 (CD30L), TNFSF9 (4-1BBL), TNFSF10 (TRAIL), TNFSF11 (RANKL), TNFSF12 (TWEAKL), TNFSF13 (APRIL), TNFSF143B (BLYS), TNFSF14 (LIGHT), TNFSF15 (VEGI), TNFSF16 (CD30L), and TNFSF18 (AITRL), and EDA, which or whose functional fragments or functional variants of the native sequence or the fragments may also be used as component A in a polypeptide construct of the invention. In particular, in this regard, all membrane-associated type II proteins (C terminus extracellular), the functional fragments or functional variants thereof, which cause a trimeric organization of their subunits as a requirement for biological activity, are also disclosed.

Another subject of the present invention is a nucleic acid, which codes for a polypeptide of the invention. This also comprises nucleic acid constructs, which contain a sequence segment coding for a polypeptide of the invention or one or more additional sequence segments. Such additional sequence segments can be, for example, sequences coding for a leader peptide, which is present as a signal for the secretion of the polypeptide or protein according to the invention in eukaryotic cells, or codes for an scFv40, i.e., the sequence of the single-chain (scFv) antibody fragment 40, which is specific for the tumor stroma antigen FAP, or for an "Antibody Mediated Apoptosis Inducing Cytokine" (AMAIZe), or for a HIS/Flag tag, a peptide sequence for the affinity purification of the expressed proteins or polypeptides. This list is provided only as an example and is not definitive.

Other sequences, which may be covered by the nucleic acid sequence, are also noncoding sequences, such as noncoding 3' and 5' sequences, including, e.g., regulatory sequences.

The nucleic acid sequences of the present invention can also be fused with nucleic acid sequences, which, for example, code for a marker sequence or code for a sequence, which codes for a polypeptide, which, for example, facilitates the isolation or purification of the polypeptide of the invention. Representative sequences, for example, include those coding for a glutathione-S transferase (GST) fusion protein, a polyhistidine (e.g., HIS 6), hemagglutinin, or HSV tag. This enumeration is by no means limiting, however.

Nucleic acids of the present invention may be DNA or RNA, particularly mRNA. The nucleic acid molecules can be double- or single-stranded. Single-stranded RNA or DNA can be either the coding (sense) or the noncoding (antisense) strand.

The nucleic acids according to the invention can be present preferably isolated. This means that the nucleic acid molecule for the nucleic acid sequence is not flanked by nucleic acid sequences, which normally flank the gene or the nucleic acid sequences (as in genomic sequences) and/or which were completely or partially purified (such as, for example, in a DNA or RNA library). For example, an isolated nucleic acid of the invention can be isolated in relation to the cellular milieu in which it occurs naturally.

In a preferred embodiment, the nucleic acid comprises one of the nucleic acid sequences presented in FIGS. 19 through 26 or consist of one of these nucleic acid sequences.

According to the invention, functional fragments or functional variants of the nucleic acids or nucleic acid constructs of the invention are also covered, to which the previous statements on the terms functional, fragment, and variant accordingly apply.

The preparation of nucleic acids, nucleic acid constructs, or functional fragments, or functional variants thereof of the invention can be carried out by means of standard methods, which are known to the person skilled in the art (see, e.g., Maniatis et al. (2001), supra). The PCR technique is used particularly in this regard. The sequence of synthesized nucleic acids according to the invention can be determined using sequencing or hybridization methods, which are also familiar to the person skilled in the art.

The invention also comprises gene products of the nucleic acids of the invention. Preferably, the gene product codes for a polypeptide of the amino acid sequences shown in FIGS. 19 through 26. A gene product of the present invention relates not only to the transcript (mRNA) but also to polypeptides or proteins, preferably in purified form. Alleles, functional fragments, or functional variants of such gene products are also included. The aforementioned definitions of these terms apply accordingly to functional fragments or functional variants of the gene products.

Another subject of the present invention is a vector, which contains the nucleic acid coding for a polypeptide of the invention. Preferably, the vectors of the invention are expression vectors, i.e., vectors that have the ability to express and/or amplify the nucleic acids in a prokaryotic and/or eukaryotic cell. The present invention relates in particular to plasmid vectors, e.g., pBABEpuro, phages, or retroviral vectors, particularly also to all vector systems, which may be used in gene therapy, e.g., also adenoviral vector systems. Within the scope of the present invention, therefore, gene therapy methods with vectors or nucleic acids or nucleic acid constructs of the invention are also disclosed as treatment methods for the disclosed medical indications of the invention.

Vectors of the invention preferably have control sequences, which enable or enhance expression of the nucleic acid of the invention and regulate transcription. Such control sequences include, for example, polyadenylation signals, promoters, e.g., natural or synthetic promoters, enhancers to effect transcription, operator sequences to regulate transcription, silencers for tissue-specific transcription, sequences coding for suitable ribosome binding sites on mRNA, sequences stabilizing mRNA, and sequences regulating the termination of transcription and/or translation. This represents only an exemplary enumeration of possible control sequences. Other possible control sequences are well known in the related art and are described, for example, by Goeddel (1990), Gene Expression Technology: Methods in Enzymology 185, Academic Press, San Diego, Calif. The control sequences can be modified, e.g., by deletion, addition, or substitution of one or more nucleic acids, to potentiate their control function.

Numerous different promoters for different organisms are known in particular. For example, a preferred promoter for vectors which are used in *Bacillus subtilis* is the AprE promoter; a preferred vector used in *E. coli* is the T7/Lac promoter; a preferred promoter used in *Saccharomyces cerevisiae* is PGK1; a preferred promoter used in *Aspergillus niger* is glaA; and a preferred promoter used in *Trichoderma reesei* (*reesei*) is cbhI. Promoters, which are suitable for use in prokaryotic host cells, include, e.g., beta-lactamase (vector pGX2907 [ATCC39344], which contains the replicon and the beta-lactamase gene), lactose promoter systems (Chang et al. (1978), Nature (London, 275: 615); Goeddel et al. (1979), Nature (London), 281: 544), alkaline phosphatase, the tryptophan (trp) promoter system (vector pATH1 [ATCC37695]), and hybrid promoters, such as the tac promoter (isolated from the plasmid pDR540 [ATCC37282]). However, other bacterial promoters, whose nucleotide sequences are generally known, enable a skilled person to ligate these with a nucleic acid of the invention, whereby linkers or adapters may also be used, to produce the desired restriction sites. Preferably, promoters which are used in bacterial systems also contain a Shine-Dalgarno sequence, which is functionally connected to the nucleic acid.

Suitable expression vectors can consist, for example, of segments of chromosomal, nonchromosomal, and synthetic DNA. Numerous derivatives of SV40 and bacterial plasmids are known for this purpose. Examples are plasmids from *E. coli*, such as colE1, pBK, pCR1, pBR322, pMb9, pUC19, and derivatives thereof, plasmids that can be used in a wide host range, such as RP4, and phage DNA, such as numerous derivatives of the lambda phage, e.g., NM989, and other DNA phages, e.g., M13, and filamentous single-stranded DNA phages, yeast plasmids, vectors, which are suitable for use in eukaryotic cells, and vectors, which consist of a combination of plasmid and phage DNA. Numerous expression techniques for use of the expression vectors of the invention are known in the related art. Such techniques are, for example, generally described in Maniatis et al. (2001), supra.

Another subject of the invention relates to a host cell, which contains the nucleic acid of the invention and/or a vector of the invention.

Host cells within the meaning of the invention are cells that are capable of functioning as host and expression vehicles for a nucleic acid or vector of the invention. These can be prokaryotic and eukaryotic host cells. Prokaryotic—bacterial—host cells are, for example, *Rhodothermus marinus*, *E. coli*, *Streptomyces*, *Pseudomonas*, *Bacillus*, *Serratia marcescens*, and *Salmonella thyphimurium*. Eukaryotic host cells comprise, for example, yeasts, such as *Saccharomyces cerevisiae*, *Pichia pastoris*, insect cells, such as Sfp, or mammalian cells, such as COS and CHO. These enumerations are by no means definitive. The selection of a suitable host cell depends on several factors, e.g., in the introduction of a vector into a host cell particularly on the employed vector of the invention.

A further subject of the invention relates to the preparation of a host cell of the invention, which comprises the following steps:
(a) Preparation of a nucleic acid of the invention or a vector of the invention,
(b) Introduction of the nucleic acid and/or vector according to step (a) into a cell.

The preparation of a nucleic acid or a vector can occur as taught by the invention by the already described standard methods and exemplary descriptions. The introduction of the nucleic acid of the invention or the vector of the invention into the host cell can occur with use of any suitable standard method. These include, for example, transformation, electroporation, transfection with the use of, e.g., calcium chloride, lipofection, infection, transduction, etc. Various standard methods are described, for example, in Maniatis et al. (2001), supra.

Another subject of the present invention is a method for preparing a polypeptide of the invention, whereby this method typically comprises the following steps: (a) culturing of a host cell of the invention under suitable conditions, (b) expression of the nucleic acid or nucleic acid construct of the invention under suitable conditions, and (c) isolation of the polypeptide from the host cell and/or culture supernatant.

Culturing a host cell means making it possible for the host cell to grow in a suitable culture medium, at a suitable pH, and at suitable temperatures. Such growth conditions depend on the host cells used in the specific case and are well known to the person skilled in the art. Instructions for culturing cells can also be found in Maniatis et al. (2001), supra.

The expression of the polypeptide can occur here typically according to the related art in suitable expression systems, preferably as a secreted product of stable transfectants, e.g., CHO-cells or other animal cells, such as Cos7 or SF9 (insect cells), or other eukaryotic cell systems, for example, *Pichia pastoris*. Preferably, the expressed polypeptides of the invention each have leader sequences suitable for secretion in the cell system. For this reason, the vectors used for expression according to the invention also contain coding segments, which code for a functional leader sequence, e.g., as described in Brocks et al. (Immunotechnology 3:173-184, 1997) for mammals and insect cells or during use of, for example, pPIC-Zalpha vectors (Invitrogen, Karlsruhe, Germany) for expression and secretion in the yeast *Pichia pastoris*.

The isolation of the polypeptide of the invention from the host cell can occur with use of standard methods, such as chromatography methods, precipitation methods, etc., which are suitable for purification of polypeptides and proteins (also see Maniatis et al. (2001), supra).

In another embodiment of the invention, the polypeptides, but optionally also nucleic acids, nucleic acid constructs, vectors, or host cells (combined here in the category of "substances of the invention") of the invention can also be used as a medication or for the preparation of medications for the treatment of diseases.

Provided these substances of the invention comprise a component C according to the invention (see above, an antibody fragment or another specifically binding protein/peptide), their use is appropriate particularly if the substances after binding of the polypeptide or fusion protein to a specific cell membrane-expressed target molecule exhibit the full biological effect via the appropriate receptor of the member of the TNF ligand family. By suitable selection of the specificity of the targeting component C, the activity of the substance of the invention is directed to the tissue to be treated, e.g., tumor tissue, and a therapeutic agent specifically optimized/intended for the particular indication/tumor entity can be prepared. A polypeptide of the invention is accumulated, e.g., during use as a tumor therapeutic agent, particularly for the treatment of solid tumors, but also of lymphatic tumors (benign or malignant), after in vivo administration by the targeting component C initially specifically in the tumor region by membrane markers formed by the tumor itself or the reactive tumor stroma/tumor vascular system and there presented to TNF-receptor-family-positive tumor cells or sensitive cells of the reactive tumor-supplying normal tissue, sensitive to a member of the TNF ligand family.

The use of substances of the invention, however, is always basically desirable for application in the therapeutic area, when the activation of a signal transduction chain, e.g., the signal cascades triggered by the TNF receptor family, for example, an apoptotic signal cascade, is to be triggered. Thus, the substances of the invention are used in the treatment or for the preparation of a medication for the treatment of all hyperproliferative diseases, for example, also for the targeted elimination of cells of the immune system in excessive immune responses, for example, in autoimmune diseases, such as, e.g., multiple sclerosis, rheumatoid arthritis, diabetes mellitus, and TEN, or in misdirected immune responses to foreign antigens, as can occur, e.g., in infectious diseases (bacterial (for example, caused by mycobacteria), viral, or protozoan). Also possible furthermore is the treatment of metabolic diseases or general hyperinflammatory conditions, particularly chronic inflammations, for example, also in allergies but also the treatment of rejection reactions of a patient's immune system to foreign tissue. In the aforementioned cases, the polypeptide of the invention must recognize, e.g., via a component C, a characteristic marker on the surface of the target cells, in which preferably an apoptotic signal cascade is to be triggered with the goal of cell death. In the case of treatment after transplantation of foreign tissue, therefore, for example, the body's own cells responsible for the rejection reaction in the transplantation patient's immune system serve as the target cells.

In general, the substances of the invention or medications are suitable for the treatment of cancer, particularly solid or lymphatic tumors, infectious diseases, metabolic diseases, inflammatory conditions, hyperproliferative diseases, autoimmune diseases, particularly rheumatoid/arthritic diseases, toxic epidermal necrolysis (TEN), multiple sclerosis, Hashimoto's thyroiditis, GVHD, viral hepatitis (HBV, HCV), alcohol-induced hepatitis, rejection reactions in liver transplantation, diseases based on hyperapoptotic reactions, and degenerative diseases, particularly neurodegenerative diseases.

Recombinant protein is preferably administered to the patient to be treated during use of the substances of the invention as a medication for the treatment of the aforementioned diseases. Alternatively, cells are removed from the patient for transfection; these are transfected in vitro with the (expression) vectors of the invention, cultured, and then given to the patient as a retransplant. The transfection is preferably performed with nucleic acids, nucleic acid constructs, or (expression) vectors, which couple the expression to a regulatable promoter. The transfected autotransplant, for example, can be injected locally, depending on the specific disease and the specific target cells. Local administration is preferred, for example, in the case of tumor therapy. In this case, tumor cells are removed from the patient, transfected in vitro, and then, provided this is possible, injected directly into the tumor, for example, for the treatment of skin tumors (e.g., melanomas), and tumors of the nervous system (e.g., glioblastomas).

Other subjects of the present invention relate to the use of the substances of the invention both for the preparation of a vaccine for active or passive immunization against infectious diseases, particularly against viral infectious diseases, and also for the preparation of a vaccine for vaccination against German measles, measles, poliomyelitis, rabies, tetanus, diphtheria, BCG, malaria, yellow fever, HIV, or influenza.

Substances of the invention can also be used for in vitro diagnosis.

Another subject of the present invention relates to methods for extracorporeal (ex vivo) manipulation, depletion, and/or removal of components present in body fluids, such as, e.g., binding partners of a component A, as defined above, or cells binding thereto or associated therewith. Such extracorporeal methods comprise preferably methods such as, e.g., apheresis, particularly the basic forms of apheresis, plasmapheresis and cytapheresis.

Plasmapheresis according to the invention includes extracorporeal manipulation, depletion, and/or removal of certain soluble or suspended components in the plasma fraction of blood, and the return of the thus treated blood to the patient. To do this, peripheral blood is removed from a patient preferably by means of a pheresis machine; anticoagulant agents are optionally added to the blood, and the blood is separated into its major components—solid (red blood cells, white blood cells, and platelets) and liquid fractions (plasma). After separation into these main components, the soluble or suspended blood components, present in the thus obtained plasma fraction, can be manipulated, depleted, and/or removed in another process step, for example, with use of the polypeptides of the invention. Next, the thus treated blood plasma together with the previously separated solid blood components can be combined and reinjected into the patient. The volume loss due to the plasmapheresis can be later replaced by isotonic saline solution in the method of the invention. Plasmapheresis as taught by the invention is preferably carried out with the use of methods such as therapeutic plasma exchange (TPE), immnunabsorption (IA), precipitation (HELP), differential membrane filtration, and other means. Plasma filtration columns are mentioned here as examples (see, e.g., U.S. Pat. No. 4,619,639, Asahi Medical Company, incorporated here by reference). Membrane filtration systems (MDF) with use of different particles and surfaces, for example, filters such as PlasmaFlo®OP-05(W)L and RheoFilter®AR2000 blood filters, can be used (manufactured by Asahi Medical Company, Ltd. of Japan). Alternatively, all suitable surfaces and particles can be used in the plasmapheresis methods of the invention.

In cytapheresis, as taught by the invention, in contrast to the previously described plasmapheresis, cellular components circulating in the blood and/or bound to bone marrow (red blood cells, white blood cells, stem cells, or platelets) or specific subpopulations of these cells are manipulated, depleted, and/or removed extracorporeally to achieve a clinical effect. Here as well, peripheral blood is taken from a patient by means of a pheresis machine. Anticoagulant agents are optionally then added to the blood and the blood is separated into its main components. Next, in the blood fraction containing the cell components, these cell components can be manipulated, depleted, and/or removed in another process step, preferably also with use of the polypeptides of the invention. In the end, the thus treated fraction can be reinjected into the patient. Preferably, in the cytapheresis of the invention, the separation of the blood into various fractions and optionally the separation of certain cell components in blood occur using methods such as centrifugation, differential membrane filtration, or other means. Furthermore, membrane filtration systems (MDF) with use of different particles and surfaces, for example, filters such as PlasmaFlo®OP-05(W)L and RheoFilter®AR2000 blood filters, can be used (manufactured by Asahi Medical Company, Ltd. of Japan).

In a third alternative of the invention, the aforementioned methods of plasmapheresis and cytapheresis can be combined, for example, to manipulate, deplete, and/or remove both soluble or suspended components in the plasma fraction of blood and cellular components circulating in blood and/or bound to bone marrow (red blood cells, white blood cells, stem cells, or platelets) or specific subpopulations of these cells in order to achieve a clinical effect. Such a combination of plasmapheresis and cytapheresis is preferably produced with use of the polypeptides of the invention.

In a preferred embodiment, the present invention relates to an (apheresis) method for extracorporeal manipulation, depletion, and/or removal of soluble, suspended, or cellular blood components comprising the following steps:

Optionally separation of the blood into one or more fractions with solid and/or liquid components;

Binding of soluble, suspended, or cellular blood components to a surface or particle coupled to a polypeptide of the invention; and Optionally separation of the bound soluble, suspended, or cellular blood components.

In a special embodiment of the apheresis method of the invention, blood can be optionally removed from a patient before the separation of the blood if necessary. Furthermore, the blood treated by the method of the invention or the thus treated blood fraction can be reinjected into the patient. To do this, it may be necessary to recombine the previously separated and possibly differently treated blood fractions with other untreated solid and/or liquid components of blood. The volume loss due to the method of the invention can be compensated by addition of appropriate fluids, e.g., by addition of an isotonic saline solution.

The step in the apheresis method of the invention for binding the soluble, suspended, or cellular blood components to a surface or particle coupled to a polypeptide of the invention can be carried out once or repeatedly as needed, in order to achieve a desired selectivity.

In the apheresis method of the invention, such surfaces and/or particles are used which were covalently coupled to the polypeptide of the invention, as defined above. To this end, the polypeptide of the invention is preferably covalently coupled to the surface and/or the particle via the coupling group(s) A present in the polypeptide.

Coupling of the polypeptides used according to the invention via the individual components A occurs preferably as described in DE 101 44 252 A1. The coupling of the polypeptides used according to the invention occurs thereby preferably to the surfaces or particles (carriers) via a bond between the first functional groups present on the carrier surface and in the polypeptide via the coupling groups present in components A. These coupling groups are preferably complementary to the functional groups of the carrier and can enter into affinity, preferably covalent bonds with these. Preferably, the functional group of component A is positioned within component A such that it is placed a suitable distance outside the domains, responsible for the biological activity, of the polypeptide of the invention. In this way, it is possible according to the invention to immobilize TNF directionally on the carrier and with retention of its biological activity. After the immobilization, the polypeptide of the invention is fixed preferably to the carrier's surface such that the three-dimensional structure of the domain(s) necessary for biological activity has not been altered compared with the non-immobilized polypeptide of the invention, and that the domain(s) during contact with cellular reaction partners is/are freely accessible for these.

In a preferred embodiment of the invention, the functional group of the carrier surface is selected from the group consisting of the amino group, carboxy group, epoxy group, maleimido group, alkylketone group, aldehyde group, hydrazine group, hydrazide group, thiol group, and thioester group.

According to the invention, the coupling groups of components A, to be immobilized, of the polypeptide of the invention are selected from a group, which contains the same species as for the functional group of the carrier surface. A surface/particle (=carrier), which can be used in the apheresis method of the invention, therefore, has on its surface a functional group, which is covalently linked to a coupling group of the polypeptide, to be immobilized, of the invention, whereby the coupling group of the polypeptide is a group different from the functional protein of the carrier. The two coupling groups and functional groups, binding together, must thereby be complementary to one another, that is, be capable of entering into a covalent bond with one another. If, for example, an amino group is used as the functional group of the carrier according to the invention, the coupling group of component A of the polypeptide of the invention is a carboxy group. If conversely a carboxy group is used as the functional group of the carrier according to the invention, the coupling group of component A of the polypeptide of the invention is an amino group as taught by the invention. If a thiol group is selected as the functional group of the carrier according to the invention, the complementary coupling group of component A of the polypeptide of the invention is a maleimido group as taught by the invention. If conversely a maleimido group is used as the functional group of the carrier, the complementary coupling group of component A of the polypeptide of the invention is a thiol group as taught by the invention. If an alkylketone group, particularly a methylketone or aldehyde group, is used as the functional group of the carrier according to the invention, the functional complementary coupling group of component A of the polypeptide of the invention is a hydrazine or hydrazide group. If conversely according to the invention a hydrazine or hydrazide group is used as the functional group of the carrier, the functional complementary coupling group of component A of the polypeptide of the invention is an alkylketone, particularly methylketone or aldehyde group, as taught by the invention. According to the invention, the functional group on the carrier surface is preferably a maleimido group, and in the coupling group of component A of the polypeptide of the invention, a thiol group.

The immobilization thereby occurs preferably directionally. In regard to the present invention, the term "immobilized directionally" or "directional immobilization" means that a polypeptide of the invention, particularly an scTNF member, is immobilized at a defined position within the scTNF member in such a way on a carrier that the three-dimensional structure of the domain(s) necessary for biological activity has not changed compared with the non-immobilized state and that this (these) TNF domain(s), for example, binding pockets for cellular reaction partners, during contact with cellular reaction partners is/are really accessible for these. "Immobilized directionally" also means that the coupling of the polypeptide of the invention on the carrier surface occurs in such a way that the immobilized protein during later use in a cellular and/or cell-like environment cannot be degraded or degraded only very slowly by protein-degrading enzymes. This means that an immobilized TNF molecule of the invention is aligned on the carrier surface in such a way that it offers as few sites of action as possible for proteases. In addition, the polypeptide of the invention before coupling can be made resistant to proteases by biomolecular methods, as described above, for example, for TNF members in the case of protease TACE.

The polypeptide of the invention via its coupled component(s) A retains its biological function and the ability to interact with other compounds/substances. If a polypeptide of the invention contains, for example, three components A (trimer), then typically each, two, or preferably only one of the three components A are bound covalently to the surface/particle.

For coupling of suitable surfaces and/or particles, all suitable surfaces and/or particles can be included to which the polypeptides of the invention can be coupled. In particular, culture plates or so-called microbeads, e.g., Dynabeads (Dynal Biotech GMBH), nanobeads, nanoparticles, or solid phases such as, for example, nylon wool, Sepharose, Sephadex, etc., are especially preferred. According to the invention, it is provided furthermore that the carrier systems used according to the invention are compact or hollow nanoparticles between 25 and 1000 nm in size. These consist either of organic or inorganic particle materials. The type of the material can be varied as taught by the invention according to the subsequent use, whereby the carrier of the nanoparticles consists preferably of biologically compatible and/or biologically degradable materials. In regard to the present invention, "nanoparticles" are understood to be furthermore binding matrixes, which comprise a carrier with a surface on which chemically reactive functional groups are arranged, which enter into affinity bonds, thus covalent and/or noncovalent bonds, with complementary functional groups of molecules to be bound, particularly the polypeptides of the invention, and in this way can stably fix the polypeptides of the invention on their surface. The carriers of the nanoparticles consist of chemically inert inorganic or organic materials and are less than 1 µm in size, preferably from 25 to 500 nm.

A special embodiment of the apheresis method of the invention comprises a biofunctionalized surface (planar or as particles), e.g., with the polypeptide of the invention scTNF, which was immobilized covalently and directionally on the surface in the previously described manner. This type of biofunctionalized surface, containing, for example, several immobilized scTNF molecules or variants thereof, makes possible a high affinity for the specific complementary binding partner, for example, TNFR1 and TNFR2. The receptors TNFR1 and particularly TNFR2 are found in highly elevated concentrations as processed, soluble molecules in the blood of tumor patients and in other diseases. The removal of TNFR from the blood of tumor patients demonstrably leads to clinically documented tumor regression, which is attributed to a reconstitution of the body's own defense (see, for example, Lentz M. R., (1999) Therapeutics Apheresis, Vol. 3, No. 1). An apheresis method with polypeptides of the invention, for example, scTNF, makes it possible that preferably both TNF receptors can be removed simultaneously and efficiently from samples. Another advantage of this method is the above-described fact that dissociation of individual components A of the polypeptide of the invention is not possible; i.e., neither an activity loss of the functionalized surface nor contamination of the treated blood with the associated substances is expected.

The apheresis method of the invention can be carried out as a continuous or discontinuous process. As a continuous process, the method of the invention is preferably carried out directly after the taking of blood or the fractionation of the removed blood and before the return of the blood to the patient without interim storage of the blood or the obtained blood fractions. In a discontinuous process, in contrast, the removed blood or the fractions of the removed blood can be stored after each step for a specific time period.

The temperature in the apheresis method of the invention is preferably 0 to 40° C. In a continuous process, the temperature is preferably 25 to 40° C., especially preferably in a range between 36° C. and 38° C. In a discontinuous process, the temperature can be between 0° C. and 40° C.

The apheresis method of the invention as described above is used preferably for diagnosis, therapy, and/or prophylaxis in diseases associated with members of the TNF ligand family, particularly in tumor diseases, particularly solid or lymphatic tumors, particularly solid and lymphatic tumors [sic]. The restoration of the homeostasis of the immune system with its humoral and cellular components is regarded as the key to the effectiveness of the apheresis method. In another application, the apheresis system of the invention can be used for this reason also in restoring the immune homeostasis in nonmalignant diseases. These include inflammatory diseases, arthritic and rheumatic diseases, or diseases of the immune system, as well as for the treatment [sic] of infectious diseases, metabolic diseases, inflammatory conditions, hyperproliferative diseases, autoimmune diseases, particularly rheumatoid/arthritic diseases, toxic epidermal necrolysis (TEN), multiple sclerosis, Hashimoto's thyroiditis, GVHD, viral hepatitis (HBV, HCV), alcohol-induced hepatitis, rejection reactions in liver transplantation, diseases based on hyperapoptotic reactions, and degenerative diseases, particularly neurodegenerative diseases.

Tumor diseases comprise in particular colon cancer, melanomas, renal carcinomas, lymphomas, acute myeloid leukemia (AML), acute lymphoid leukemia (ALL), chronic myeloid leukemia (CML), chronic lymphocytic leukemia (CLL), gastrointestinal tumors, lung carcinomas, gliomas, thyroid tumors, breast carcinomas, prostate tumors, hepatomas, various virus-induced tumors, such as, e.g., papilloma virus-induced cancer (e.g., cervical carcinoma), adenocarcinomas, herpes virus-induced tumors (e.g., Burkitt's lymphoma, EBV-induced B cell lymphoma), hepatitis B-induced tumors (hepatocellular carcinomas), HTLV-1 and HTLV-2 induced lymphomas, acoustic neurinoma, cervical cancer, lung cancer, throat cancer, anal carcinoma, glioblastoma, lymphomas, rectal cancer, astrocytoma, brain tumors, stomach cancer, retinoblastoma, basalioma, brain metastases, medulloblastomas, vaginal cancer, pancreatic cancer, testicular cancer, melanoma, thyroid cancer, bladder cancer, Hodgkin's syndrome, meningeomas, Schneeberg's disease, bronchogenic carcinoma, pituitary tumor, mycosis fungoides, esophageal cancer, breast cancer, carcinoids, neurinoma, spinocellular carcinoma, Burkitt's lymphoma, laryngeal cancer, kidney cancer, thymoma, uterine carcinoma, bone cancer, non-Hodgkin's lymphoma, urethral cancer, CUP syndrome, head-neck tumors, oligodendroglioma, vulvar cancer, intestinal cancer, colon cancer [sic], esophageal carcinoma, wart involvement, small bowel tumors, craniopharyngeomas, ovarian carcinoma, soft tissue tumors, ovarian cancer, liver cancer, pancreatic carcinoma, cervical carcinoma, endometrial carcinoma, liver metastases, penile cancer, tongue cancer, gallbladder cancer, leukemia, plasmocytoma, uterine cancer, lid tumor, prostate cancer, etc.

Arthritic diseases comprise particularly monarthritis, oligoarthritis, polyarthritis, acute arthritis (primarily septic, crystal-induced, reactive arthritis and acute arcoidosis), subacute arthritis, chronic arthritis (primarily rheumatoid arthritis, arthritis in seronegative spondylarthritis), infectious arthritis, para- or postinfectious arthritis, rheumatoid arthritis, juvenile chronic arthritis, arthritis in inflammatory connective tissue diseases and vasculitis, allergic arthritis, arthritis in conjunction with metabolic diseases and nutrition-induced disorders, arthritis in endocrine disturbances, arthritis in granulomatous diseases, arthritis in diseases of the hematopoietic system, arthritis in joint hemorrhaging due in blood coagulation disorders, neoplastic arthritis, paraneoplastic arthritis, (post-)traumatic arthritis, arthritis in diseases of the articular cartilage, arthritis in neuropathies, arthritis in pustular, abscessing, necrotizing dermatoses or dermatoses proceeding with tissue neutrophilia, arthritis in other extra-articular primary diseases, as well as allergic arthritis, chlamydia-induced arthritis, dysenteric arthritis, gonorrheal arthritis, arthritis mutilans, psoriatic arthritis, dry arthritis, syphilitic arthritis, tuberculous arthritis, uric arthritis, etc.

Another subject of the present invention is a pharmaceutical composition or a vaccine, containing the polypeptides of the invention, nucleic acid constructs of the invention, vectors of the invention, and/or host cells of the invention, as well as pharmaceutically compatible aids, additives, and/or carrier substances (e.g., also solubilizers). The pharmaceutical compositions or vaccines according to the invention are preferably used for the treatment of cancer diseases, particularly solid or lymphatic tumors, as well as for the treatment of infectious diseases, metabolic diseases, inflammatory conditions, hyperproliferative diseases, autoimmune diseases, particularly rheumatoid/arthritic diseases, toxic epidermal necrolysis (TEN), multiple sclerosis, Hashimoto's thyroiditis, GVHD, viral hepatitis (HBV, HCV), alcohol-induced hepatitis, rejection reactions in liver transplantation, diseases based on hyperapoptotic reactions, and degenerative diseases, particularly neurodegenerative diseases.

Therefore, according to the invention, a combination of substances of the invention with pharmaceutically acceptable carriers, aids, and/or additives is also disclosed. Appropriate production methods are disclosed in "Remington's Pharmaceutical Sciences" (Mack Pub. Co., Easton, Pa., 1980), which is part of the disclosure of the present invention. For parenteral administration, for example, sterile water, sterile saline solution, polyalkylene glycols, hydrogenated naphthalene, and particularly biocompatible lactide polymers, lactide/glycolide copolymers, or polyoxyethylene/polyoxypropylene copolymers may be considered as carrier materials. Pharmaceutical compositions of this type according to the invention may be used for all medical indications disclosed above. In addition, the compositions of the invention may contain fillers or substances, such as lactose, mannitol, substances for the covalent linking of polymers, such as, e.g., polyethylene glycol to inhibitors of the invention, complexing with metal ions or inclusion of materials in or on special preparations of polymer compounds, such as, e.g., polylactate, polyglycolic acid, hydrogel, or on liposomes, microemulsion, micelles, unilamellar or multilamellar vesicles, erythrocyte fragments, or spheroplasts. The specific embodiments of the compositions are selected depending on the physical behavior, for example, in regard to solubility, stability, bioavailability, or degradability. Controlled or constant release of the active components of the invention in the composition includes formulations based on lipophilic depots (e.g., fatty acids, waxes, or oils). Coatings of substances of the invention or compositions containing such substances, namely, coatings with polymers, are disclosed within the scope of the present invention (e.g., poloxamers or poloxamines). Furthermore, the substances or compositions of the invention may have protective coatings, e.g., protease inhibitors or permeability enhancers.

All administration routes known in the related art are disclosed basically within the scope of the present invention for the substances of the invention or the pharmaceutical compositions of the invention or vaccines; preferably the manufacture of a medication or a vaccine occurs for the treatment of the aforementioned diseases or disorders by the parenteral, i.e., for example, subcutaneous, intramuscular, or intravenous, oral, intranasal, intra-aural, transdermal, topical (e.g., via gels, ointments, lotions, creams, etc.), intraperitoneal, intrapulmonary (e.g., AERx® inhalation technology, commercially available from Aradigm or Inhance™ pulmonary delivery system, commercially available from Inhale Therapeutics), vaginal, rectal, or intraocular administration routes. Typically, pharmaceutical compositions of the invention are solid, liquid, or aerosol-like (e.g., spray), depending on the packaging or administration.

In a preferred embodiment, the therapeutically effective amount of a polypeptide of the invention is administered as needed to a patient. The precise dose typically depends on the purpose of the basic treatment and can be determined by a person skilled in the art with use of known methods from the related art. As is known from the related art, adjustments may be necessary, for example, in regard to the metabolic breakdown of the polypeptides of the invention, in regard to systemic versus local administration, as well as to the age, body weight, general state of health, gender, nutrition, time of administration, interaction of active ingredients, or the severity of the disease. Such adjustments can be made by a person skilled in the art by means of methods known in the related art.

In a preferred embodiment, a combination of polypeptides of the invention for use as adjuvant is disclosed. An adjuvant within the meaning of this invention is particularly a composition that causes no specific immune response to an immunogen, but is capable of enhancing the immune response to this immunogen. Stated differently, administration of the adjuvant alone causes no immune response to this immunogen, whereas administration together with this immunogen produces an immune response, which is greater than the immune response after administration of the immunogen alone. An adjuvant can contain in addition pharmaceutically acceptable carriers, aids, and/or additives or be administered with them, as is disclosed here for vaccines and pharmaceutical compositions. Furthermore, an adjuvant can be administered together with the vaccines or pharmaceutical compositions disclosed above.

It can be stated in summary that the invention provides a polypeptide, which has increased stability, as a result of which the entire molecule of a member of the TNF ligand family consists of a protein strand or polypeptide strand (e.g., scTNF), so that the monomers (components A) of the members of the TNF ligand family can no longer dissociate. scTNF, as well as the polypeptides of the invention, which relate to other members of the TNF ligand family, exhibits no qualitative differences in its bioactivity to the normal soluble sTNF (also wild-type TNF or wtTNF), but is more stable by far and therefore exhibits higher bioactivity, and thus is effective at lower concentrations. Like the normally soluble TNF (wtTNF), scTNF was able to trigger apoptosis in sensitive cells, to activate the transcription factor NF-κB, the receptor TNFR1 but not TNFR2, and in the presence of certain antibodies (e.g., 80M2) also to activate the receptor TNFR2. This applies to polypeptides of the invention, which relate to other members of the TNF ligand family. When the polypeptides of the invention are used with a coupling group to produce biofunctionalized surfaces and the use thereof, for example, for apheresis, no bleeding of the polypeptide of the invention or a return of harmful ligands into the system is observed.

Furthermore, the polypeptide of the invention, for example, scTNF, represents an ideal starting material for the preparation of new bifunctional molecules. On the one hand, the polypeptide of the invention, for example, scTNF, or functional fragments thereof can bind covalently to cell surfaces. According to the invention, this has the advantage that only a single covalent bond must be created for stable binding of the molecule. In a normal soluble wild-type member of the TNF ligand family, for example, soluble sTNF, all three monomers of the individual homotrimer must be covalently linked to the surface in order to obtain a stable construction, because otherwise the non-covalently bound monomers dissociate off. In this embodiment of the polypeptide of the invention, use in apheresis, e.g., with scTNF as a biofunctional active substance to remove TNF receptors from body fluids is especially advantageous.

This also applies to the preparation of fusion proteins. These are especially interesting in order to concentrate a member of the TNF ligand family, for example, TNF, with use of an antibody fragment fused to TNF, for example, scFv, at a specific desired location in the body (so-called "targeting" strategies). In normal soluble TNF (wtTNF), this type of fusion protein must consist of homotrimeric TNF, in which each of the at least three monomers carries the antibody moiety, as a result of which large and unstable molecules form, which in turn dissociate into their monomers and/or tend to aggregate and thereby can be inactivated. A fusion protein derived from scTNF is linked with only one molecule of the antibody, so that the entire fusion protein in turn consists of a single, stable protein strand or polypeptide strand. The descriptions for TNF above can be applied to all members of the TNF ligand family.

It is also possible by means of the present invention, due to the covalent linkage of the monomers (components A) of the polypeptide of the invention, to introduce selectively and stably mutations in only one or also two or more of the at least three monomers (components A). Thus, e.g., point mutations are known, which force receptor selectivity; i.e., for example, in the case of TNF, binding still occurs only at one of the two TNF receptors (TNFR1 and TNFR2). It is possible according to the invention to produce for the first time, e.g., TNF mutants, which are capable of selectively binding a molecule of TNFR1 and two molecules TNFR2 simultaneously; i.e., heteromeric receptor complexes would result. In this way it is possible for the first time to prepare heteromeric, stable, single-chain members of the TNF ligand family, which selectively bind and activate only one of several possible receptors.

Of course, the explanatory statements made above as examples in regard to TNF can be applied to the other members of the TNF ligand family.

The present invention will be illustrated in greater detail by means of the following figures:

FIGS. 1-3 show the results of different biological cytotoxicity tests, in which the properties, particularly the specificity, of different scTNF variants were compared with those of classic soluble wild-type TNF, i.e., the soluble extracellular domain of human TNF (NCBI gi:25952111, 17.09 kDa, as a monomer of the soluble form, abbreviated TNFhum or sTNF, AA 79-181).

Both transfected mouse fibroblasts and human Kym1 cells were used for these tests. Exemplary results of the analyses are presented, whereby scTNF variants were tested with peptide linkers of different length between the individual TNF modules (i.e., TNF monomers). The peptide linkers in each case consist of the threefold or fourfold amino acid repetitions GGGS (or also GlyGlyGly-Ser (SEQ. ID NO: 41) (designated as "single-chain TNF3x" or "single-chain TNF4x" or as "scTNF3x" or "scTNF4x").

In another test batch, the effect of neutralizing TNF-specific antibodies on the cytotoxicity of wild-type TNF (TNFhum) or scTNF was tested. Freshly prepared dilutions of soluble human TNF (TNFhum) or the above-described scTNF variants with threefold (3x) or fourfold (4x) glycine-serine peptide linkers (scTNF3x: GGGS-GGGS-GGGS (SEQ. ID NO: 2)/scTNF4x: GGGS-GGGS-GGGS-GGGS (SEQ. ID NO: 3)) were used. Concentration series with 1:3 dilutions in the presence and absence of neutralizing TNF-specific antibodies (αTNF-AB) [1 µg/mL] were used. The above-described control bacterial lysate was used as the negative control. It is evident as the result that the cytotoxic effect of soluble human wild-type TNF or scTNF can be abolished by neutralizing TNF-specific antibodies (see the top three curves in the diagram), namely, within a broad concentration range (0.03-10 ng/mL). No differences were found between the reaction of scTNF with 3x and scTNF with 4x peptide linkers.

Figure 2:
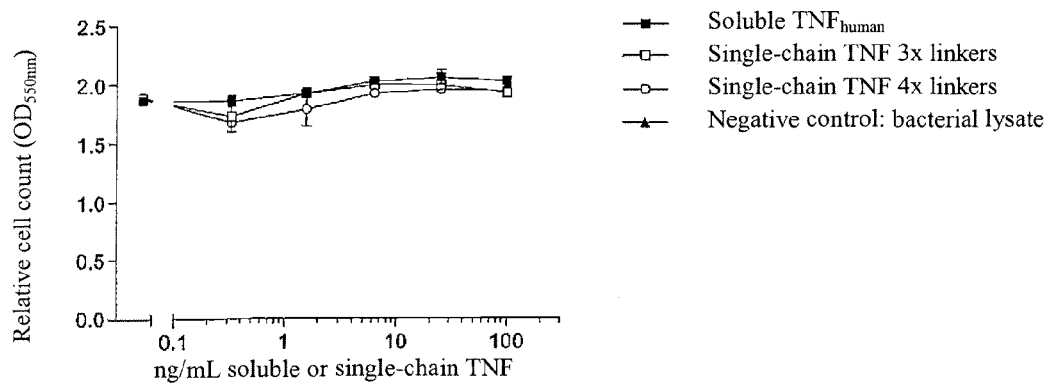

FIG. 2 shows the result of a cytotoxicity test in which the effect of sTNF and scTNF variants on TNFR2-receptor chimera (TNFR2-Fas) expressing cells was studied. In this test batch, mouse fibroblasts were used which stably express receptor chimeras consisting of TNFR2 and Fas (TNFR2-Fas, whereby the extracellular part stems from TNFR2 and the intracellular part from the Fas-receptor) (MF TNFR2-Fas cells). MF TNFR2-Fas cells (like the wild-type TNFR2) can only be activated by an adequate TNFR2 stimulus, for example, by membrane-associated TNF, but not by soluble TNF. Result: As expected, both the soluble human TNF (TN- Fhuman) and the scTNF variants with the 3x and 4x peptide linkers (scTNF3x, scTNF4x) had no toxic effect on the MF TNFR2-Fas cells. In other words, sTNF and the scTNF variants are equally incapable of activating TNFR2-chimera (TNFR2-Fas) expressing cells; i.e., they cause no cell death in these cells. The control bacterial lysate used as the negative control (as described above) as expected also had no toxic effect.

Figure 1:
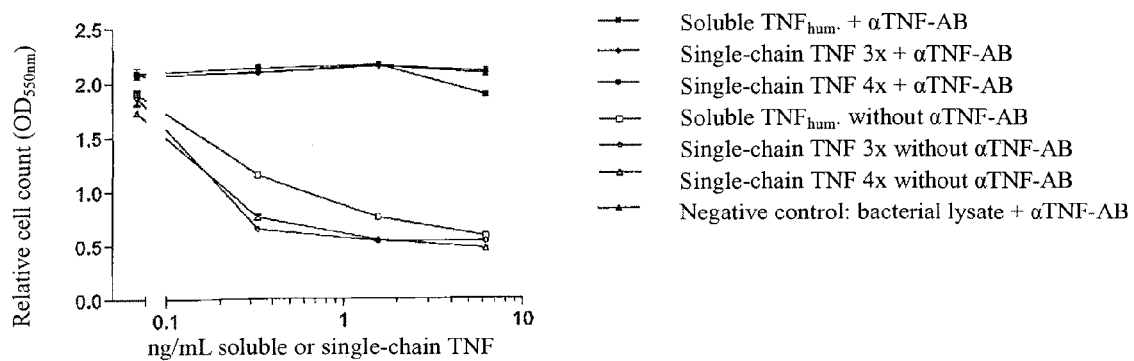
FIG. 1 shows the result of a typical cytotoxicity test of TNF. Mouse fibroblasts (MF) from TNFR1/TNFR2 double-knockout mice, which stably express TNFR1 receptor chimeras (TNFR1-Fas) (MF TNFR1-Fas cells) were used as target cells. Such cells express a hybrid molecule, which consists extracellularly of the corresponding part of TNFR1 and thereby binds TNF, and intracellularly has the highly apoptotically acting intracellular domain of the Fas-receptor. These MF TNFR1-Fas cells can be activated by TNFR1-specific stimuli, but mediate a Fas-specific death signal. The surviving cell count was quantified after 24 hours by absorption with staining with a dye. A control bacterial lysate was used as a negative control, which was a non-scTNF expressing bacterial lysate, which was processed identically to the recombinant scTNF proteins. It can be stated as a result that both the conventional human soluble TNF (TNFhum) and the recombinant scTNF variants led to cell death. A comparable dose-dependent cytotoxic effect of TNFhum or scTNF is evident (see the bottom three curves in the diagram), whereby the specific activity of the scTNF is at least equivalent, if not even higher, than that of the wild-type TNF. As expected, the negative control shows no toxic effect.
Figure 3:
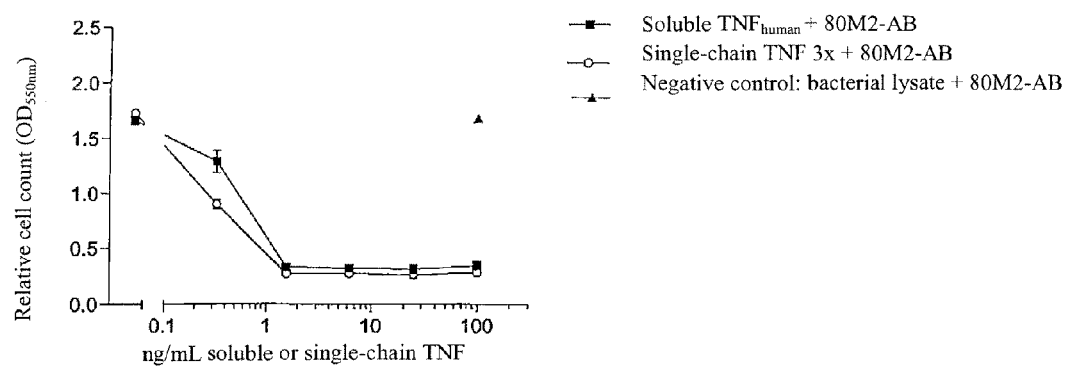

FIG. 3 shows the result of a cytotoxicity test in which the effect of soluble human wild-type TNF and an scTNF variant in combination with a special TNFR2-specific antibody, 80M2, on TNFR2-chimera (TNFR2-Fas) expressing cells was studied. The test batch corresponds that from FIG. 2 with the difference that the soluble wild-type TNF or the scTNF with 3x peptide linkers (scTNF3x) was given together with the antibody 80M2. The antibody 80M2 is known for conferring the special signal capacity of membrane-bound TNF on normal soluble TNF. The result shows that both the soluble wild-type TNF and scTNF in combination with the antibody 80M2 achieve a strong cytotoxic effect via the TNFR2-Fas receptor chimeras. The reason for this is that soluble TNF in combination with certain TNFR2-specific antibodies, such as, e.g., 80M2, can exhibit the activity of membrane-bound TNF. MF TNFR2-Fas cells die after incubation with soluble TNF or scTNF in the presence of such a ligand-receptor complex-stabilizing antibody (80M2-AB). In other words, in the presence of this antibody, soluble TNF and scTNF have a similar toxic effect in the MF TNFR2/FAS cells, as this otherwise can occur only with membrane-associated TNF. The control bacterial lysate used as the negative control (as described above in FIG. 1) as expected had no toxic effect.

FIGS. 4-10 show the results of different stability tests, which demonstrate that the scTNF variants of the invention due to their structure have a vastly better stability than soluble wild-type TNF.

sTNF or the scTNF variants were incubated in a serum-containing culture medium at concentrations of 3.0 to 0.01 ng/mL at 37° C. and 5% $CO_2$ for different time periods.

After this, the functionality of the sTNF or scTNF variants (scTNF3x, scTNF4x) was tested in the cytotoxicity tests based on MF TNFR1-Fas cells and Kym1 cells. For this cytotoxicity test, 1:3 dilutions were used starting with a 3.0 ng/mL TNF sample. A control bacterial lysate, which was employed in the cytotoxicity tests described above, was used as the negative control (non-scTNF expressing bacterial lysate, which was processed identically to the recombinant scTNF proteins).

Figure 4:
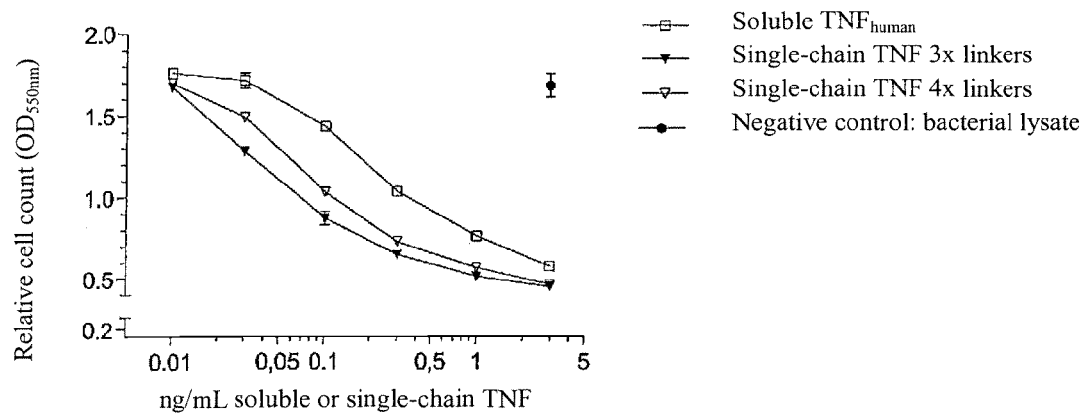

FIG. 4 shows the bioactivity of the employed molecules BEFORE the stability test in mouse fibroblasts MF TNFR1-Fas cells. Soluble human wild-type TNF (TNFhuman) and scTNF dilutions (freshly prepared) were used and diluted out on the cells. Both the soluble control TNF and the scTNF variants after incubation with MF led to their cell death. The control bacterial lysate as expected had no toxic effect. The $ED_{50}$ values (half-maximal effective concentration) were about 0.2 ng/mL for the soluble human wild-type TNF and 0.1 ng/mL for the two employed different scTNF variants. The control bacterial lysate used as the negative control as expected had no toxic effect.

Figure 5:
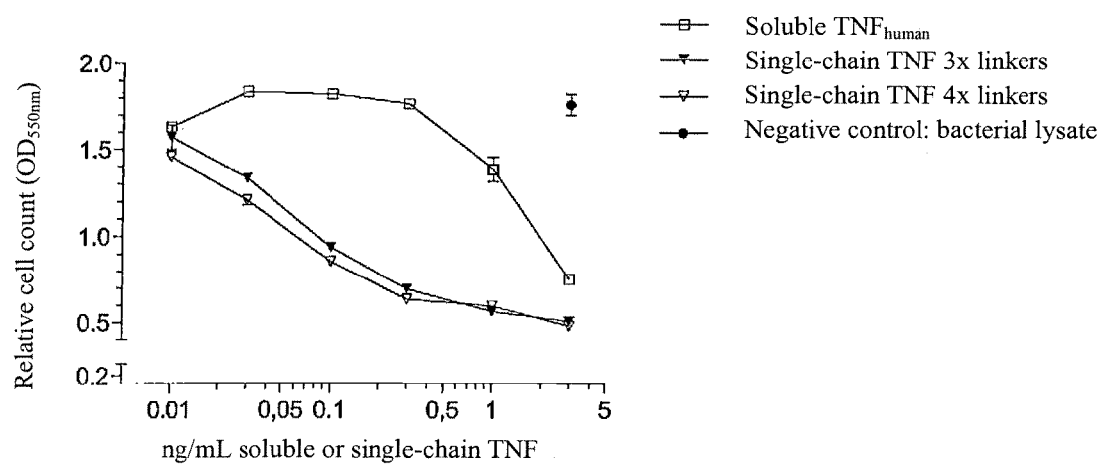

FIG. 5 shows the result of a stability test with mouse fibroblasts MF TNFR1-Fas cells. The wild-type TNF and scTNF dilutions, shown in FIG. 5, were hereby incubated for 8 days in a cell incubator before the test in order to be able to evaluate the stability of the samples. A clear decline in the bioactivity of the soluble wild-type TNF (TNFhuman) was measured after 8 days at 37° C., whereas the activity of both scTNF variants (scTNF3x, scTNF4x; see above for explanation) remained unchanged. An $ED_{50}$ value of about 2 ng/mL (used freshly prepared: 0.2 ng/mL, cf. FIG. 4) was obtained for the wild-type TNF. The scTNF variants with $ED_{50}$ values of about 0.1 ng/mL remained as active as the freshly used samples (cf. FIG. 4). The control bacterial lysate used as the negative control as expected had no toxic effect.

Figure 6:
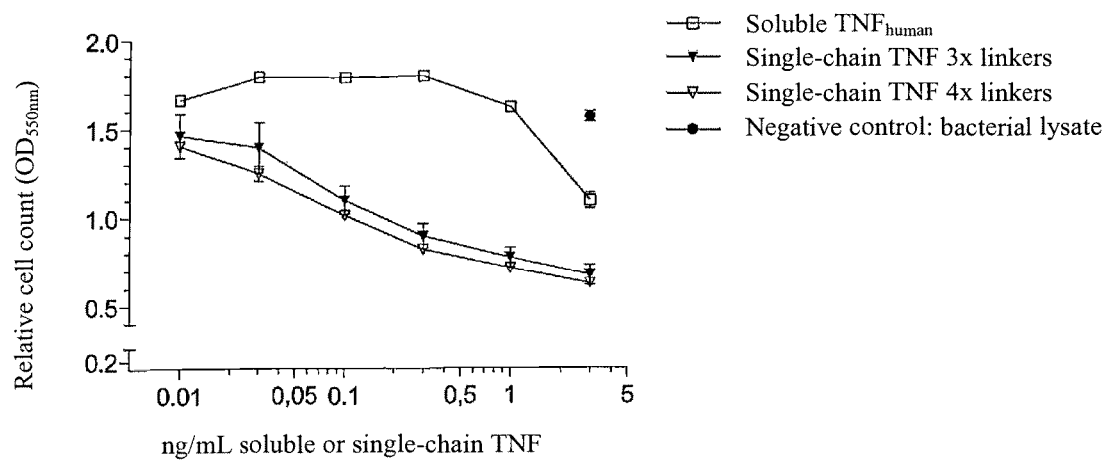

FIG. 6 shows the result of a stability test with mouse fibroblasts MF TNFR1-Fas cells. The wild-type TNF and scTNF solutions were now incubated as explained in FIG. 5 for 14 days in a cell incubator. A clear further decline in the bioactivity of the wild-type TNF was measured after 14 days at 37° C., whereas the activity of the scTNF variants remained approximately the same. An $ED_{50}$ value of about 2.8 ng/mL (freshly prepared 0.2 ng/mL, cf. FIG. 4) was obtained for sTNF; the scTNF variants with 0.13 ng/mL remained virtually as active as the freshly used samples (0.1 ng/mL, cf. FIG. 4). The control bacterial lysate used as the negative control as expected had no toxic effect.

Figure 7:
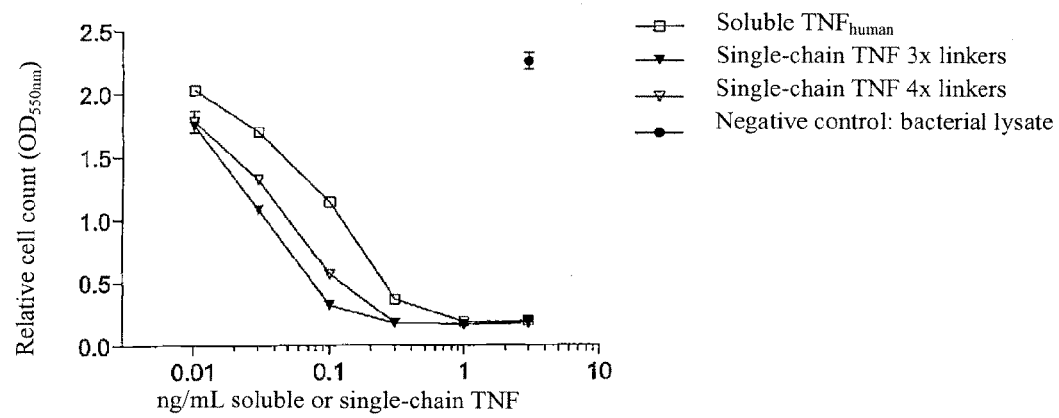

FIG. 7 shows the result of a stability test with the human cell line Kym1. Kym1 cells express normal human wild-type TNF receptors and also react cytotoxically to TNF. The experiment was performed similar to the stability tests with mouse fibroblasts according to FIGS. 4-6: Soluble wild-type TNF or the scTNF variants (scTNF3x, scTNF4x) were incubated in a serum-containing medium at concentrations of 3.0 to 0.01 ng/mL at 37° C. and 5% $CO_2$ for different time periods. Next, the functionality of the soluble sTNF or the scTNF variants was tested in cytotoxicity tests on Kym1 cells. Starting with a 3.0 ng/mL TNF samples, 1:3 dilutions were used for the test. The above-described control bacterial lysate was used as the negative control. Wild-type TNF and scTNF dilutions were freshly prepared and used. The result shows that both wild-type TNF and the scTNF variants possessed high cytotoxic activity. The $ED_{50}$ values are about 0.1 ng/mL for the wild-type TNF and about 0.06 ng/mL for the scTNF variants. The control bacterial lysate used as the negative control as expected had no toxic effect.

Figure 8:
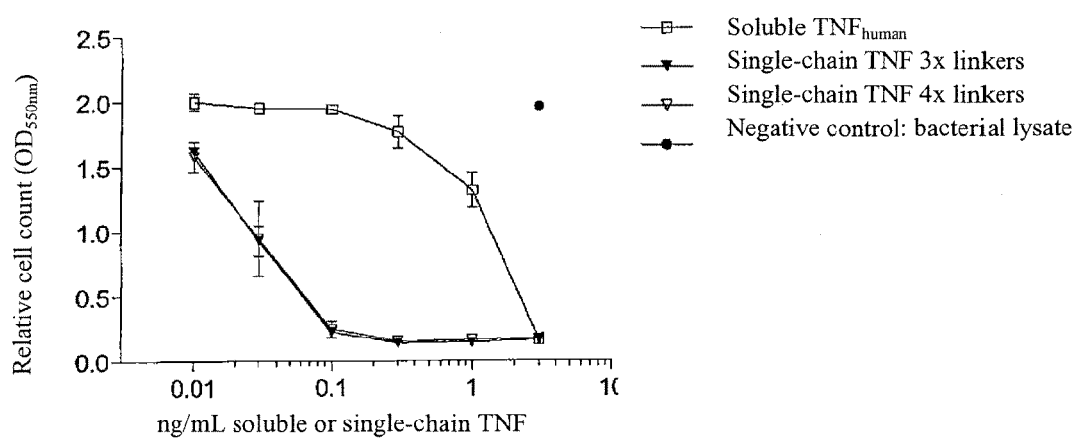

FIG. 8 shows the result of a stability test with the human cell line Kym1. The wild-type TNF and scTNF solutions were hereby incubated for 16 days in a cell incubator. Next, the Kym1 cell cytotoxicity test was performed. A clear decline in the activity of the sTNF was measured after 16 days at 37° C., whereas the toxicity, i.e., the bioactivity, of the scTNF variants remained approximately the same. An $ED_{50}$ value of about 1.2 ng/mL was obtained for the wild-type TNF. The scTNF variants with 0.06 ng/mL remained as active as the freshly used samples. The control bacterial lysate used as the negative control as expected had no toxic effect.

Figure 9:
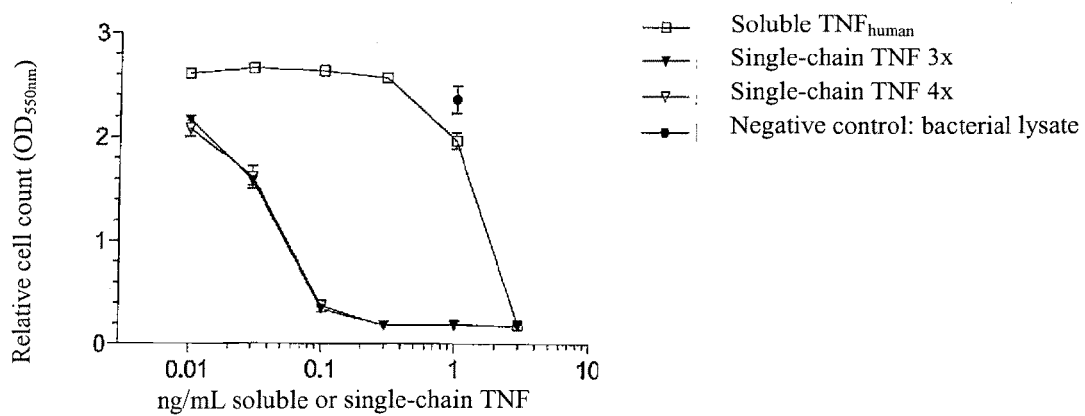

FIG. 9 shows the result of a stability test with the human cell line Kym1. sTNF and scTNF solutions were hereby incubated for 22 days in a cell incubator. A clear further decline in the activity of sTNF was measured after 22 days at 37° C. The scTNF variants continued to be stable. The control bacterial lysate used as the negative control as expected had no toxic effect.

The following Table 1 shows the results data from the stability tests according to FIGS. 7 and 9 as a comparison:

TABLE 1

| | Comparison of the $ED_{50}$ values from FIGS. 7 + 9 | | |
|---|---|---|---|
| | $ED_{50}$ freshly titrated (FIG. 7) | $ED_{50}$ after 22 days (FIG. 9) | Loss of activity |
| sTNF | 0.1 ng/mL | 1.50 ng/mL | >90% |
| scTNF | 0.06 ng/mL | 0.07 ng/mL | Barely detectable |

Figure 10:
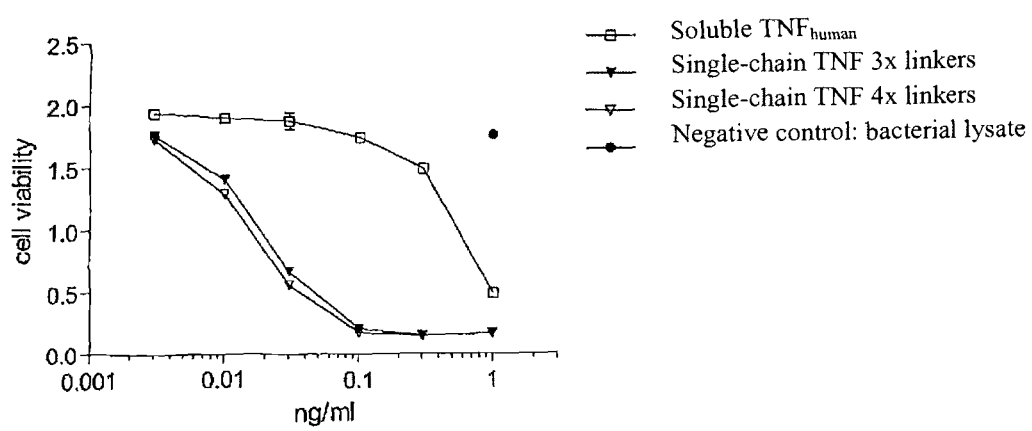

FIG. 10 shows the result of a stability test with the human cell line Kym1. Dilutions of 3 ng/mL were titrated out after 16 days at 37° C. In contrast to the previous FIGS. 4-9, in this test a titration curve was prepared starting with a 3 ng/mL TNF dilution stored for 16 days, whereas in the previous shown titration curves the particular dilutions were prepared and then stored for the indicated time period. It can be demonstrated that a comparison of the data from FIG. 8 (similar test with 16 days of incubation) and FIG. 10 shows no major differences. The control bacterial lysate used as the negative control as expected had no toxic effect.

Figure 11:
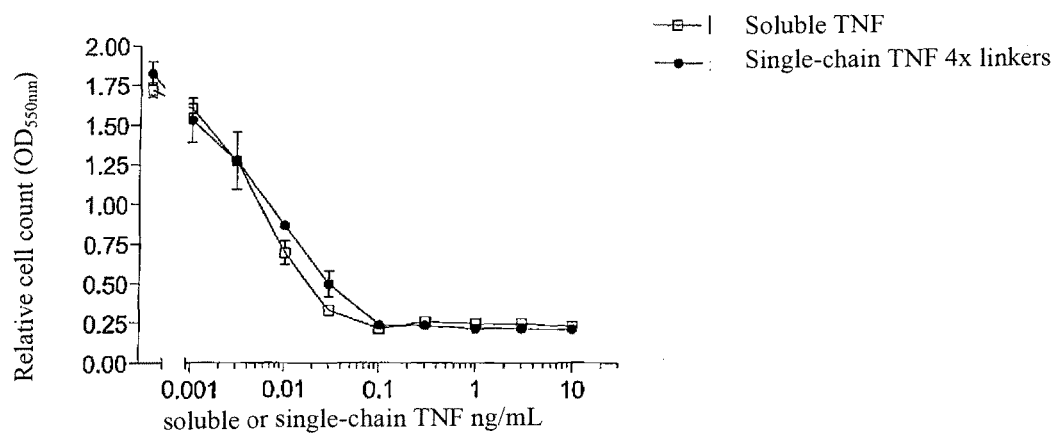

FIG. 11 shows the result of a stability test in human serum. To test the stability of wild-type TNF and scTNF in human serum, in a first test batch the soluble wild-type TNF and the scTNF4x variant were diluted in 100% serum and freshly titrated out. An $ED_{50}$ value of 0.004 ng/mL was measured as the result for the wild-type TNF and an $ED_{50}$ value of 0.007 ng/mL for the scTNF variant.

Figure 12:
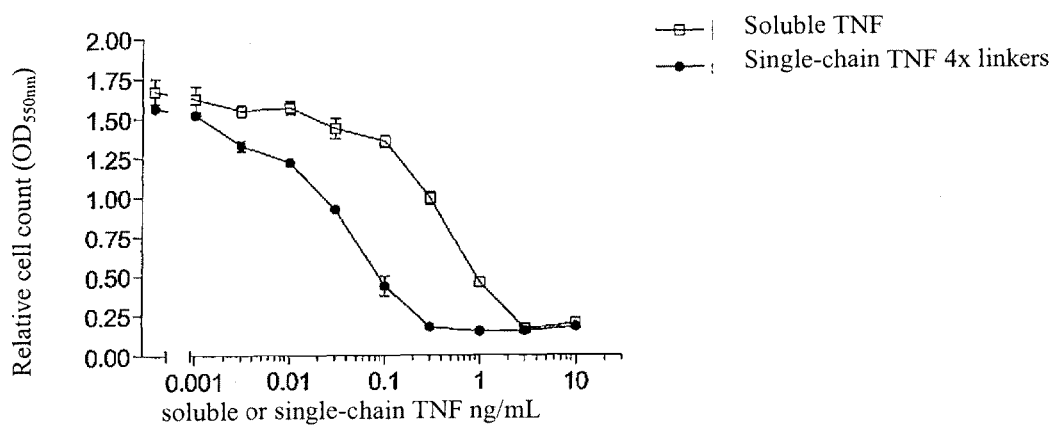

FIG. 12 shows the result of a stability test in human serum. To test the stability of wild-type TNF and scTNF in human serum, in another test batch, wild-type TNF and the scTNF4x variant were stored for 8 days at 37° C. in 100% fresh serum that was not heat-inactivated, and then titrated out in Kym1 cells. An $ED_{50}$ value of 0.40 ng/mL was measured as the result for wild-type TNF and an $ED_{50}$ value of 0.03 ng/mL for the scTNF variant. The effects of the 8-day storage in 100% serum were as follows: In comparison with freshly titrated out scTNF, scTNF stored for 8 days exhibited a loss of activity by a factor of about 4.3, whereas for the soluble sTNF there was a dramatic loss of activity by a factor of 100 during storage in 100% serum. The scTNF of the invention, in comparison with sTNF, accordingly exhibited a much higher bioactivity after an 8-day incubation in serum and thereby proved to be very stable in human serum at physiological temperatures.

In the following Table 2, the data of the results from FIGS. 11 and 12 are once again presented for clarification.

TABLE 2

Comparison of the $ED_{50}$ values from FIGS. 11 + 12

| | $ED_{50}$ freshly titrated (FIG. 11) | $ED_{50}$ after 8 days (FIG. 12) | Loss of activity |
|---|---|---|---|
| Soluble TNF | 0.004 ng/mL | 0.40 ng/mL | 100-fold |
| Single-chain TNF | 0.007 ng/mL | 0.03 ng/mL | 4.3-fold |

Figure 13:
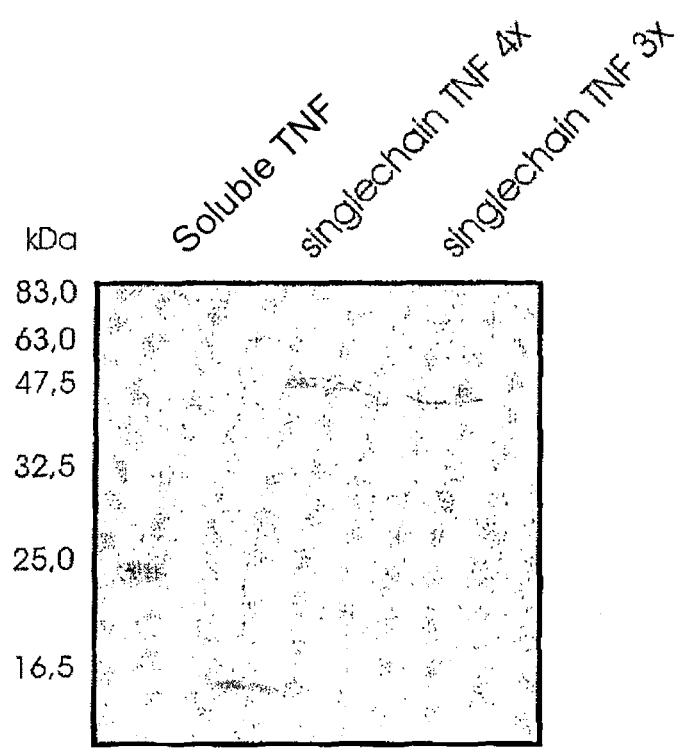

FIG. 13 shows the result of an analysis by polyacrylamide gel electrophoresis under reducing and denaturing conditions. A silver gel of a purified wild-type TNF and the purified scTNF variants, scTNF3x and scTNF4x, is shown. The samples were each incubated with β-mercaptoethanol (final 5%) at 95° C. for 5 minutes. About 500 ng of sTNF and scTNF4x and about 150 ng of scTNF3x per lane were applied to the silver gel. The result of the silver gel of the scTNF variants separated in 15% SDS-PAGE shows that both scTNF variants under reducing conditions as well had a molecular weight of about 50 kDa, which agrees with their structure. It can also be stated that the different amounts of the applied proteins scTNF3x and scTNF4x had no effect on the result. This confirms the stability of the proteins or polypeptides of the invention under reducing and denaturing conditions. The result for sTNF, in contrast, shows that the protein breaks down into its monomers of about 17 kDa.

Figure 14:
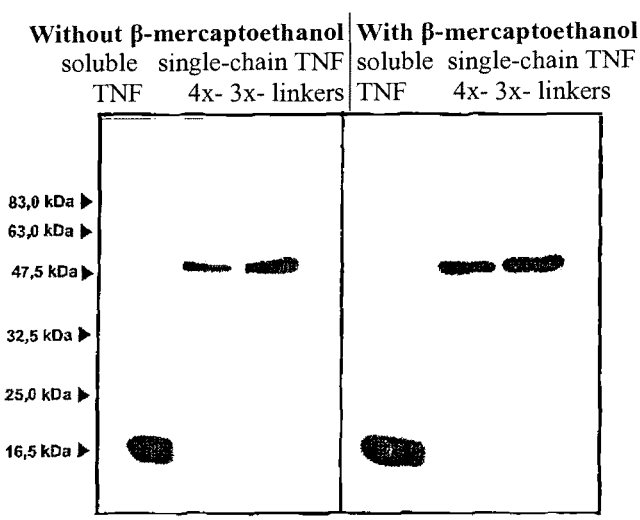

FIG. 14 shows the result of a stability test under reducing and denaturing conditions. In this test, a Western Blot of samples, separated in 15% SDS-PAGE, of wild-type TNF and the scTNF variants scTNF3x and scTNF4x was performed. Two parallel batches were carried out in which the samples in one batch were each incubated with β-mercaptoethanol (final 5%) at 95° C. for 5 minutes, whereas no β-mercaptoethanol incubation occurred in the other batch. The detection after the electrophoresis run was performed with an anti-TNF antibody. It is evident as a result that the antibody specifically detected the protein of both scTNF variants in clear bands at about 50 kDa. For the wild-type TNF, the protein was specifically detected at about 17 kDa. This again confirms the stability of the scTNF3x and scTNF4x variants of the invention under reducing and denaturing conditions and also coincides as expected with the results from FIG. 13.

Figure 15:
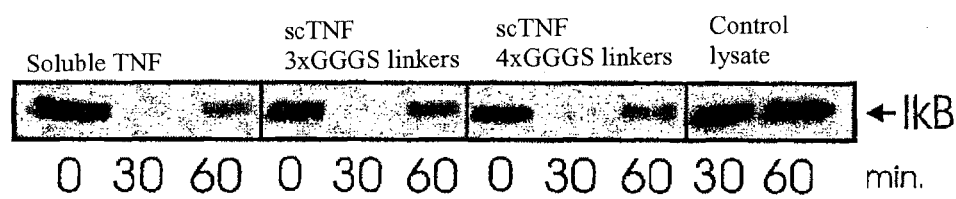

FIG. 15 shows the result of an IkappaB degradation assay. IkappaB (I-κB) is an inhibitor of the transcription factor nuclear factor kappa B (NF-κB), and as is generally known is caused to degrade after addition of TNF, as a result of which NF-κB is activated. To determine the degradation of I-κB, cell lysates were prepared 0, 30, and 60 minutes after stimulation with 10 ng/mL each of wild-type TNF, scTNF3x, and scTNF4x and then analyzed using the Western Blot assay with I-κB-specific antibodies. The result shows that the transient degradation of I-κB of both wild-type TNF and the two scTNF variants was induced, whereby the reaction behavior of the scTNF variants corresponds to that of the wild-type TNF. The control bacterial lysate used as the negative control (as described above, a non-scTNF expressing bacterial lysate, which was processed identically to the recombinant scTNF-proteins) as expected had no effect on the I-κB degradation.

Figure 16:
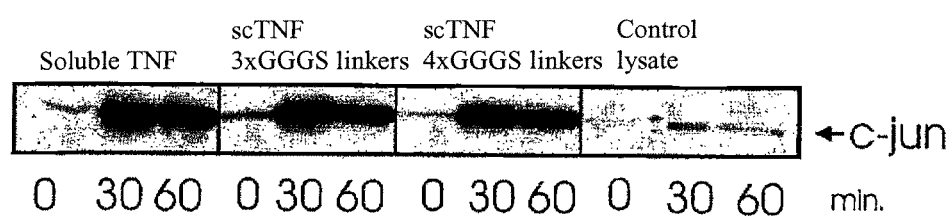

FIG. 16 shows the result of a JNK assay. JNK (c-jun N-terminal kinase) is a stress-induced kinase, which as is known is very highly activated by TNF. After stimulation of Kym-1 cells for 0, 30, or 60 minutes with 10 ng/mL each of wild-type TNF, scTNF3x, and scTNF4x, cell lysates were prepared and the JNK activity was determined by immunoprecipitation of JNK with JNK-specific antibodies and subsequent kinase assay with GST c-Jun as the substrate. The control bacterial lysate used as the negative control (as described above) as expected did not activate JNK kinase. The result shows that both scTNF variants and wild-type TNF activated JNK, whereby the reaction behavior of the scTNF variants corresponded to that of the wild-type TNF.

Figure 17:
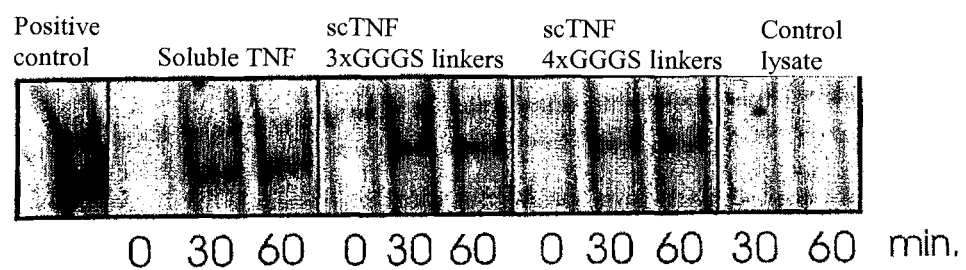

FIG. 17 shows the result of an Electrophoretic Mobility Shift Assay (EMSA). Another typical test to determine the activity of TNF is the translocation of the transcription factor NF-κB into the cell nucleus after induction of the I-κB degradation. For this purpose, cell nucleus preparations of non-stimulated KYM-1 control cells (zero minutes of stimulation) or of stimulated cells (30 and 60 minutes of stimulation) were made. The stimulation of the cells occurred in each case with wild-type TNF, scTNF3x, and scTNF4x. The transcription factor NF-κB, translocated into the cell nucleus, was detected with the use of NF-κB-specific, radioactively labeled oligo-nucleotides. The result shows that NF-κB was translocated into the cell nucleus. The reaction behavior of the scTNF variants corresponds to that of the wild-type TNF.

Figure 18:
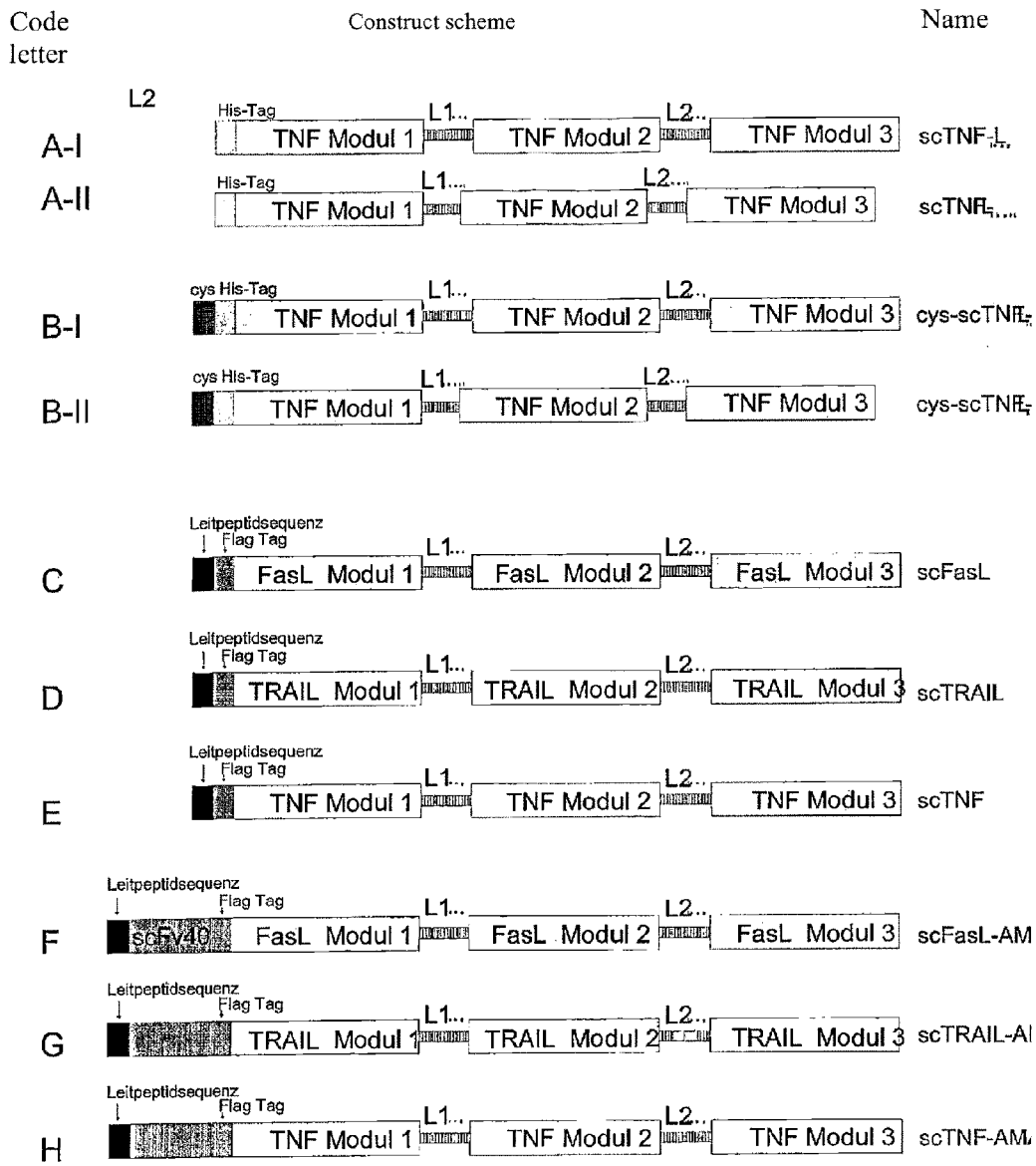

FIG. 18 shows an exemplary construct scheme of the polypeptides of the invention, presented for TNF (as a member of the TNF ligand family). The designations have the following meanings:

Constructs AI/AII and BI/II have an optimized codon usage for the expression of proteins in *E. coli*, and represent molecules which are each linked with Gly-Gly-Gly-Ser-3x linker or 4x linker (SEQ. ID NOs: 2 and 3). All molecules have a histidine tag N-terminally for easier purification; the molecules BI/BII in addition have a short amino acid chain with a cysteine residue for directional covalent linkage.

Constructs C to H are suitable for expression of the proteins in eukaryotic cells; they have the appropriate leader peptide sequences N-terminally.

sc=is the abbreviation for single chain, cys=designates an N-terminal peptide linker with internal cysteine for covalent coupling, $L1_{long}$ or $L2_{long}$=designates linker 1 or 2, each with the amino acid sequence (GGGS-GGGS-GGGS-GGGS-GGGS or $(GGGS)_4$ (SEQ. ID NO: 3), $L1_{short}$ or $L2_{short}$=designates linker 1 or 2, each with the amino acid sequence GGGS-GGGS-GGGS or $(GGGS)_3$ (SEQ. ID NO: 2), Leader peptide sequence=is the amino acid sequence for the secretion of the protein from eukaryotic (host) cells.

scFv10=stands for the sequence of the single-chain (scFv) antibody fragment 40, specific for the tumor stroma antigen FAP, AMAIZe=is the abbreviation for "Antibody-Mediated Apoptosis-Inducing Cytokines" and His/Flag tag=stands for the peptide sequence for an affinity purification of the expressed proteins.

FIGS. 19A and 19B shows the nucleic acid sequence and the corresponding amino acid sequence of scTNF-$L_{short}$ (construct A-II) (SEQ. ID NOs: 25 and 26)

Features of Construct A-II
- His tag peptide sequence for affinity purification of the formed protein: amino acids (abbreviated as "AA" below in FIGS. 19 through 26) AA 5-10, nucleotide (abbreviated as "NT" in FIGS. 19 through 26 below) NT 13-30
- Sequence of the human TNF module1 (extracellular domain, AA 79-181, of the natural human TNF molecule, sequence with optimized *E. coli* codon usage): AA 11-169, NT 31-507
- Sequence of the $(GGGS)_3$-linker1: (SEQ. ID NO: 2) AA 170-181, NT 508-543
- Sequence of the human TNF module2 (extracellular domain, AA 79-181, of the natural human TNF molecule, sequence with optimized *E. coli* codon usage): AA 182-335, NT 544-1005
- Sequence of the $(GGGS)_3$-linker2: (SEQ. ID NO: 2) AA 336-347, NT 1006-1041
- Sequence of the human TNF module3 (extracellular domain, AA 79-181, of the natural human TNF molecule, sequence with optimized *E. coli* codon usage): AA 348-501, NT 1042-1503
- Stop codon: NT 1504-1506

FIGS. 20A and 20B shows the nucleic acid sequence and the corresponding amino acid sequence of cys-scTNF-$L_{short}$ (construct B-II) (SEQ. ID NOs: 27 and 28)

Features of Construct B-II
- Amino acid cysteine for covalent coupling: AA 9, NT 25-27
- His tag peptide sequence for affinity purification of the formed protein: AA 15-20, NT 43-60
- Sequence of the human TNF module1 (extracellular domain of the natural human TNF molecule, sequence with optimized *E. coli* codon usage): AA 21-181, NT 61-543
- Sequence of the $(GGGS)_3$-linker1: (SEQ. ID NO: 2) AA 182-193, NT 544-579
- Sequence of the human TNF module2 (extracellular domain of the natural human TNF molecule, sequence with optimized *E. coli* codon usage): AA 194-347, NT 580-1041
- Sequence of the $(GGGS)_3$-linker2: (SEQ. ID NO: 2) AA 348-359, NT 1042-1077
- Sequence of the human TNF module3 (extracellular domain of the natural human TNF molecule, sequence with optimized *E. coli* codon usage): AA 360-513, NT 1078-1539
- Stop codon: NT 1540-1542

FIGS. 21A and 21B shows the nucleic acid sequence and the corresponding amino acid sequence of scFasL (construct C) (SEQ. ID NOs: 29 and 30)

Features of Construct C
- Leader peptide sequence for secretion of the protein in eukaryotic cells: AA 1-15, NT 1-45
- Flag tag peptide sequence for affinity purification of the formed protein: AA 19-26, NT 55-78
- Sequence of the human FasL module1 (extracellular domain, AA 139-281, of the natural human FasL molecule): AA 30-173, NT, 90-519
- Sequence of the $(GGGS)_4$-linker1: (SEQ. ID NO: 3) AA 174-189, NT 520-567
- Sequence of the human FasL module2 (extracellular domain, AA 139-281, of the natural human FasL molecule): AA 190-332, NT 568-996
- Sequence of the $(GGGS)_4$-linker2: (SEQ. ID NO: 3) AA 333-348, NT 997-1044
- Sequence of the human FasL module3 (extracellular domain, AA 139-281, of the natural human FasL molecule): AA 349-491, NT 1045-1473
- Stop codon: NT 1474-1476

FIGS. 22A, 22B and 22C shows the nucleic acid sequence and the corresponding amino acid sequence of scTRAIL (construct D) (SEQ. ID NOs: 31 and 32)

Features of Construct D
- Leader peptide sequence for secretion of the protein in eukaryotic cells: AA 1-15, NT 1-45
- Flag tag peptide sequence for affinity purification of the formed protein: AA 19-26, NT 55-78
- Sequence of the human TRAIL module1 (extracellular domain, AA 95-281, of the natural human TRAIL molecule): AA 30-216, NT 88-648
- Sequence of the $(GGGS)_4$-linker1: (SEQ. ID NO: 3) AA 217-232, NT 649-696
- Sequence of the human TRAIL module2 (extracellular domain, AA 95-281, of the natural human TRAIL molecule): AA 233-419, NT 697-1257
- Sequence of the $(GGGS)_4$-linker2: (SEQ. ID NO: 3) AA 420-435, NT 1258-1305
- Sequence of the human TRAIL module3 (extracellular domain, AA 95-281, of the natural human TRAIL molecule): AA 436-622, NT 1306-1866
- Stop codon: NT 1861-1863

FIGS. 23A and 23B shows the nucleic acid sequence and the corresponding amino acid sequence of scTNF (construct E) (SEQ. ID NOs: 33 and 34)

Features of Construct E
- Leader peptide sequence for secretion of the protein in eukaryotic cells: AA 1-15, NT 1-45
- Flag tag peptide sequence for affinity purification of the formed protein: AA 19-26, NT 55-78
- Sequence of the human TNF module1 (extracellular domain of the natural human TNF molecule): AA 30-184, NT 88-552
- Sequence of the $(GGGS)_4$-linker1: (SEQ. ID NO: 3) AA 85-200, NT 553-600
- Sequence of the human TNF module2 (extracellular domain of the natural human TNF molecule): AA 201-355, NT 601-1065
- Sequence of the $(GGGS)_4$-linker2: (SEQ. ID NO: 3) AA 356-371, NT 1066-1113

Figure 27:
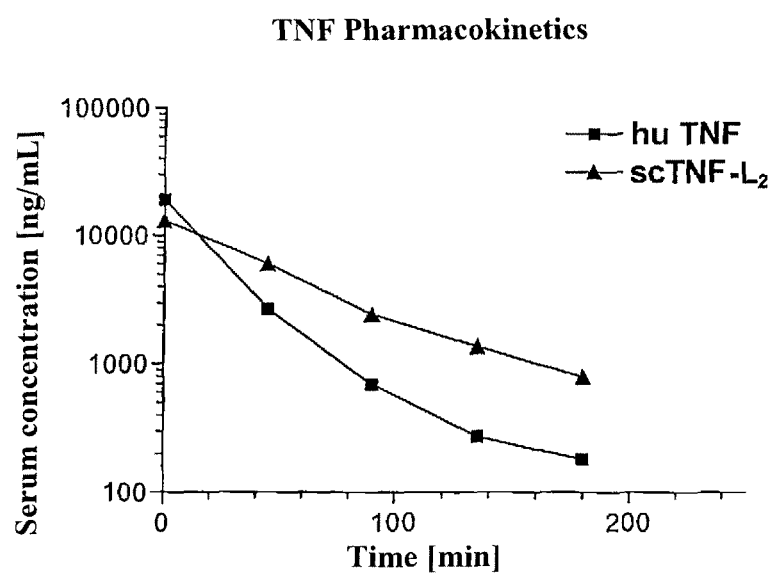

Sequence of the human TNF module3 (extracellular domain of the natural human TNF molecule): AA 372-526, NT 1114-1581
Stop codon: NT 1799-1581
FIGS. 24A, 24B and 24C shows the nucleic acid sequence and the corresponding amino acid sequence of scFasL-AMAIZe (construct F) (SEQ. ID NOs: 35 and 36)
Features of Construct F
　Leader peptide sequence for secretion of the protein in eukaryotic cells: AA 1-19, NT 1-57
　Sequence of the single-chain (scFv) antibody fragment 40 specific for the tumor stroma antigen FAP: AA 20-267, NT 58-801
　Flag tag peptide sequence for affinity purification of the formed protein: AA 278-285, NT 832-855
　Sequence of the human FasL module1 (extracellular domain, AA 139-281, of the natural human FasL molecule): AA 290-432, NT 868-1296
　Sequence of the (GGGS)$_4$-linker1: (SEQ. ID NO: 3) AA 433-448, NT 1297-1344
　Sequence of the human FasL module2 (extracellular domain, AA 139-281, of the natural human FasL molecule): AA 449-591, NT 1345-1773
　Sequence of the (GGGS)$_4$-linker2: (SEQ. ID NO: 3) AA 592-607, NT 1774-1821
　Sequence of the human FasL module3 (extracellular domain, AA 139-281, of the natural human FasL molecule): AA 608-750, NT 1822-2250
　Stop codon: NT 2251-2253
FIGS. 25A, 25B-25C and 25D shows the nucleic acid sequence and the corresponding amino acid sequence of scTRAIL-AMAIZe (construct G) (SEQ. ID NOs: 37 and 38)
Features of Construct G
　Leader peptide sequence for secretion of the protein in eukaryotic cells: AA 1-19, NT 1-57
　Sequence of the single-chain (scFv) antibody fragment 40 specific for the tumor stroma antigen FAP: AA 20-267, NT 58-801
　Flag tag peptide sequence for affinity purification of the formed protein: AA 278-285, NT 832-855
　Sequence of the human TRAIL module1 (extracellular domain, AA 95-281, of the natural human TRAIL molecule): AA 289-475, NT 865-1426
　Sequence of the (GGGS)$_4$-linker1: (SEQ. ID NO: 3) AA 476-491, NT 1427-1476
　Sequence of the human TRAIL module2 (extracellular domain, AA 95-281, of the natural human TRAIL molecule): AA 492-678, NT 1477-2034
　Sequence of the (GGGS)$_4$-linker2: (SEQ. ID NO: 3) AA 679-694, NT 2035-208 [sic]
　Sequence of the human TRAIL module3 (extracellular domain, AA 95-281, of the natural human TRAIL molecule): AA 695-, NT 2083-2643
　Stop codon: NT 2644-2646
FIGS. 26A, 26B and 26C shows the nucleic acid sequence and the corresponding amino acid sequence of scTNF-AMAIZe (construct H) (SEQ. ID NOs: 39 and 40)
Features of Construct H
　Leader peptide sequence for secretion of the protein in eukaryotic cells: AA 1-19, NT 1-57
　Sequence of the single-chain (scFv) antibody fragment 40 specific for the tumor stroma antigen FAP: AA 20-267, NT 58-801
　Flag tag peptide sequence for affinity purification of the formed protein: AA 278-285, NT 832-855
　Sequence of the human TNF module1 (extracellular domain, AA 79-181, of the natural human TNF molecule): AA 289-443, NT 865-1329
　Sequence of the (GGGS)$_4$-linker1: (SEQ. ID NO: 3) AA 444-, NT 1330-1377
　Sequence of the human TNF module2 (extracellular domain, AA 79-181, of the natural human TNF molecule): AA 460-614, NT 1378-1842
　Sequence of the (GGGS)$_4$-linker2: (SEQ. ID NO: 3) AA 615-630, NT 1843-1890
　Sequence of the human TNF module3 (extracellular domain, AA 79-181, of the natural human TNF molecule): AA 631-785, NT 1891-2353
　Stop codon: NT 2356-2358
FIG. 27 shows the pharmacokinetics of human wild-type TNF and human scTNF (cf. Example 2). The data in FIG. 27 show a clear increase in the in vivo half-life of the scTNF variants. A clearly increased duration of action in vivo is expected for scTNF compared with TNF, which thereby emphasizes the value of scTNF, particularly of scTNF-L$_2$, as a potential therapeutic agent.

Figure 28:
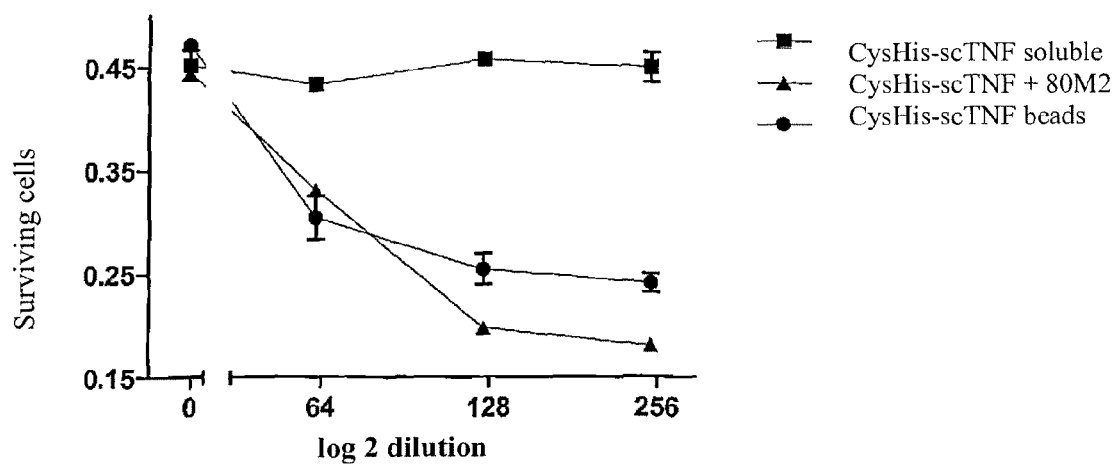

FIG. 28 shows CysHis-scTNF coupled covalently to particles (silica). This covalently coupled CysHis-scTNF is bioactive and possesses the special activity of membrane-bound TNF; i.e., it activates TNFR2. FIG. 28 shows that cells from mouse fibroblasts, which are transfected with the construct TNFR2-Fas and were treated with serial dilutions of the indicated reagents, are totally resistant to soluble wtTNF. After covalent coupling of reduced CysHis-scTNF to silica microparticles (beads) according to established protocols (DPA 2001, No. DE 10144252), these cause a strong cytotoxic response (circle), like a positive control consisting of CysHis-scTNF and a TNFR2 cross-linking antibody, mAk 80M2 (triangle). Cys-His scTNF, which is not coupled, as expected shows no activity on TNFR2-positive cells (squares).

The present invention will be illustrated below by the examples:

DETAILED DESCRIPTION OF THE INVENTION

Examples

Example 1

Preparation of Different Polypeptide Constructs of the Invention

All clonings were performed according to standard protocols. The conditions for these are given below.
Standard PCR:
　60 ng of template, 0.5 µL, of 100 µM primer, 1 µL of 10 mM dNTPs, 5 µL of 10× buffer, and 2 U of Taq polymerase were amplified in a reaction volume of 50 µL using the following PCR program. Denaturation: 94° C. 3 minutes; 15 cycles: denaturation 94° C. 30 seconds, annealing 55° C. 30 seconds, elongation 72° C. 90 seconds; final elongation: 72° C. 7 minutes.
Digestion of PCR Products:
　The PCR product was purified over an agarose gel and eluted and then digested with the appropriate restriction enzymes (see specific instructions) in a 40-µL reaction batch at an optimal cleavage temperature (indicated by the manufacturer) for 2 hours.
Digestion of Vectors:
　1 µg of vector was digested with 5 U of the appropriate restriction enzymes in a 20-µL reaction volume for 2 hours at an optimal cleavage temperature (this depends on employed enzyme and is indicated by the manufacturer). To dephosphorylate the vectors, 10 U of alkaline phosphatase was added for 1 hour to the reaction digest.

Fill-In Reaction:

The batch from a vector digestion was combined with 33 µM dNTPs and 1 U/1 µg of DNA Klenow fragment of DNA polymerase I and incubated for 15 minutes at 25° C. This reaction was stopped with 10 mM EDTA for 20 minutes at 75° C.

Ligation:

Vector and insert were ligated at a molar ratio of 1:5 together with 400 U of ligase in a 10-µL volume overnight at 16° C.

I. Preparation of scTNF$_{human}$ (scTNF) with 4x or 3x Linkers:

Two scTNF variants were prepared, which differ in the length of the peptide linker between the individual modules. Primers with a 4x or 3x peptide-linker sequence were used: linker$_{long}$ with the (GGGS)$_4$: (SEQ. ID NO: 3) sequence or linker$_{short}$ with the (GGGS)$_3$: (SEQ. ID NO: 2) sequence. The produced constructs accordingly contained either only two 4x linkers (L1 or L2 with (GGGS)$_4$: (SEQ. ID NO: 3)—designated as "long") or only two 3x linkers (L1 or L2 with (GGGS)$_3$—designated as "short").

1. A standard PCR was run with primers V and I or II (for linker$_{long}$) and the pQE-9 vector with a TNF module (pQE9-HisTNF) as the template. The vector bears a His tag sequence for later affinity purification of the produced protein.
2. The obtained PCR product I was then digested with 20 U of the appropriate restriction enzymes StuI and HindIII at 37° C. The same digestion and a dephosphorylation reaction were performed with the pQE9-HisTNF vector, and the PCR product I was inserted into the pQE9-HisTNF vector by ligation. The result of this step was a His tag-TNF module1 with a linker1$_{short\ or\ long}$, or the following construct in the pQE9 vector:

EcoRI-His tag-TNF module1-linker1$_{short\ or\ long}$-BamHI
3. PCR product II was produced by another PCR with primers III and I or II (for linker$_{long}$) and the pQE9-HisTNF vector as the template. PCR product II was then cut each time with 20 U of the restriction enzymes EcoRI and HindIII and inserted into the pQE9-HisTNF vector, which was cut with the same enzymes and dephosphorylated. The result of this cloning was a pQE9 vector, which was as follows:

TNF module2-linker2$_{short\ or\ long}$-BamHI

This construct has no sequence for a His tag before the TNF sequence.
4. The cloned PCR product II from step 3 was first cut from the vector with the restriction enzyme Hind III and then partially with BamHI (1 U/µg of DNA). The pQE9-His tag TNF module1-linker1$_{short\ or\ long}$ vector was also cut sequentially with the restriction enzymes BamHI and HindIII, dephosphorylated, and the PCR product II ligated into this vector. The result was a pQE9 vector with following construct:

His tag-TNF module1-linker1$_{short\ or\ long}$ TNF module2-linker2$_{short\ or\ long}$.
5. Another PCR was performed under standard conditions with the pQE9-HisTNF vector as the template and primers III and IV, and the obtained PCR product III was sequentially digested with restriction enzymes BamHI (40 U) and HindIII (40 U). This fragment was then ligated into a pBluescript SKII vector, which was also cut with the restriction enzymes BamHI and HindIII. The result of this cloning was a pBluescript SKII vector, which contains the TNF module 3 without linkers.
6. The pQE9 vector with the His tag-TNF module1-linker1$_{short\ or\ long}$ TNF module2-linker2$_{short\ or\ long}$ construct was cut with the restriction enzyme EcoRI; this vector was then treated with the Klenow fragment of DNA polymerase I from *E. coli*, to carry out a fill in. After this step, a partial restriction digestion was carried out with the enzyme BamHI (1 U/µg DNA).
7. Parallel to Step 6, the pBluescript SKII vector, which contains the TNF module 3, was cut with the restriction enzyme XbaI; this vector was then treated with the Klenow fragment of DNA polymerase I from *E. coli*, to carry out a fill in. After this step, a second restriction digestion was carried out with the enzyme BamHI under standard conditions with additional dephosphorylation.
8. The fragment obtained by the restriction digestion from Step 6 was then ligated into the linear vector generated in Step 7. The constructs were in reverse order as follows:

HindIII-TNF module3-linker2$_{short\ or\ long}$-TNF module2-linker2$_{short\ or\ long}$-TNF module1-His tag-EcoRI
9. The reverse TNF construct from Step 8 was cut from the pBluescript SKII vector with the restriction enzymes EcoRI and HindIII and ligated into the pQE9-HisTNF vector, which was treated with the same enzymes and dephosphorylated. As a result, the following construct with the complete scTNF in correct orientation formed:

EcoRI-His Tag-TNF module1-linker1$_{short\ or\ long}$-TNF module2-linker2$_{short\ or\ long}$-TNF module3-HindIII
10. To prepare an scTNF with an N-terminal cysteine, the oligos cys-scTNF VI and VII were annealed (20 µL each of 100 µM oligo VI or VII were heated together for 5 minutes at 95° C. and slowly allowed to cool to room temperature), and oligo1 was formed in this way. The construct from Step 9 was digested with the restriction enzymes EcoRI and BbsI and the oligo1, which has the same cut sites, was ligated into the vector. Alternatively, the cysteine was inserted via PCR mutagenesis. The result of this cloning was the following construct:

EcoRI-Cysteine-His Tag-TNF module1-linker1$_{short\ or\ long}$-TNF module2-linker2$_{short\ or\ long}$-TNF module3-HindIII All constructs were verified by sequencing.

The expression was carried out in the *E. coli* strain XL-1 blue. The purification of the expressed scTNF variants occurred with use of chromatographic methods (His tag affinity and anion exchange chromatography).

The sequences of the employed primers are given below:

Peptide linker sequences at the protein level (SEQ. ID NOs: 2 and 3)

```
3x GGGS-linker (short) = (GGGS)₃:
GGGS GGGS GGGS

4x GGGS-linker (long) = (GGGS)₄:
GGGS GGGS GGGS GGGS
```

Peptide linker sequences at the nucleotide level (SEQ. ID NOs: 4 and 5)

```
3x GGGS-linker (short):
5'GGT GGC GGT TCT GGT GGC GGT TCT GGT GGC GGA
TCC3'

4x GGGS-linker (long):
5'GGT GGC GGT TCT GGT GGC GGT TCT GGT GGC GGT TCT
GGT GGC GGA TCC3'
```

Primers for the Clonings

```
scTNF Primer I (SEQ. ID NO: 6)
5'-TCG ATT AAG CTT CCC GGG GGA TCC GCC ACC AGA ACC
GCC ACC AGA ACC GCC ACC CAG AGC GAT GAT ACC GAA
GTA AAC CTG ACC-3' scTNF Primer II (SEQ. ID NO: 7)
5'-ATC GAT TAA GCT TCC CGG GGG ATC CGC CAC CAG AAC
CGC CAC CAG AAC CGC CAC CAG AAC CGC CAC CCA GAG
CGA TGA TAC CGA AGT AAA CCT GAC C-3' scTNF Primer III (SEQ. ID NO: 8)
5'-CCC CGA ATT CGG ATC CTC TTC TCG TAC CCG TCG TGA
CAA ACC G-3' scTNF Primer IV (SEQ. ID NO: 9)
5'-GGG GGG GAA GCT TAT CGA TAG TTA GAT ATC ATC ACA
GAG CGA TGA TAC CGA AG-3' scTNF Primer V (SEQ. ID NO: 10)
5'-CCT GTA CCT GAT CTA CTC CCA GGT TCT GTT CAA AGG
CCA GG-3'
```

Oligo for CysHis Insertion:

```
cys-scTNF Primer VI (SEQ. ID NO: 11)
AAT TCA TTA AAG AGG AGA AAT TAA CTA TGG GAG AGC
TCA TCG AAG GTC GCT GCG CCG GTG GAT CTG GTC ATC
ATC ATC ACC ATC ACG GCT CAG ACG G cys-sscTNF Primer VII (SEQ. ID NO: 12)
CGC TCC GTC TGA GCC GTG ATG GTG ATG ATG ATG ACC
AGA TCC ACC GGC GCA GCG ACC TTC GAT GAG CTC TCC
CAT AGT TAA TTT CTC CTC TTT AAT G
```

II. Preparation of scFasL in pcDNA3 and AMAIZe Constructs:

The standard conditions given in Example 1 were used for the following clonings.

A. Generation of the HA Signal in pcDNA3

1. Digestion of the pcDNA3 vector with KpnI and NotI.
2. Preparation of the HA oligo with the KpnI-HA-signal-NotI sequence by annealing of the primers HA-IF and HA-IIR for the leader peptide sequence:
3. Ligation of the HA oligo (contains KpnI and NotI cut sites) into the pcDNA3 vector B. Preparation of scFasL in the pcDNA3(+) Vector 1. PCR with primers FasL#1F and FasL#2R on the template FasL-AMAIZE vector. The preparation of this type of constructs is described in German Patent Application DE 10045591.3, which is herewith incorporated in its entirety in the disclosure of the present invention. The product of this PCR 1 was a NotI-Flag tag-FasL module1-linker1-BamHI-XbaI construct.
2. Using the NotI and XbaI restriction cut sites, this construct was cloned in the pcDNA3-HA sequence vector with the same enzymes, so that the following construct forms:

HA sequence-Flag tag-FasL module1-linker1-BamHI-XbaI

3. The following PCR product 2 was generated with the use of another PCR on the template FasL-AMAIZE vector and the primers FasL#3 and FasL#1:

blunt end-FasL module2-linker2-BamHI-XbaI

4. In the next step, the pcDNA3 vector from Step 2 was digested with BamHI; this cut site was filled with the Klenow enzyme and then cut with XbaI, so that a "blunt end" and a "sticky end" formed. PCR product 2 was then cloned in this thus modified vector, with the formation of the following construct:

HA sequence-Flag tag-FasL module1-linker1-FasL module2-linker2-BamHI-XbaI

5. For the third module, another PCR was performed with the template FasL-AMAIZE vector and the primers FasL#4 and FasL#5. The formed PCR product was then digested with the restriction enzymes BamHII and XbaI and ligated into the vector, cut with the same enzymes, from Step 4. The result of this cloning was the following construct in the pcDNA3 vector:

HA sequence-NotI-Flag tag-FasL module1-linker1-FasL module2-linker2-FasL module3-stop-XbaI.

To prepare the scFasL- or scTNF-AMAIZe constructs, the corresponding scFasL or scTNF was digested with the restriction enzymes NotI or EcoRI and XbaI and the inserts were inserted as cassettes into the corresponding AMAIZe vectors (see German Patent Application DE 10045591.3), whereby these vectors were also cut with the enzymes NotI or EcoRI and XbaI. The following constructs were prepared in this way:

Leading peptide-scFv40-Flag tag-FasL module1-linker1-FasL module2-linker2-FasL module3

Leading peptide-scFv40-Flag tag-TNF module1-linker1-TNF module2-linker2-TNF module3

The sequences of the employed primers are given below: (SEQ. ID NOs: 13-19)

```
FasL#1R:
5'ATCGATTTCTAGACCCGGGGGATCGCCACCAGAACCGCCACCAGAACC
GCCACCAGAACCGCCACCGAGCTTATATAAGCCGAAAAACGTCTGAGATT
C3'

FasL#2F:
5'GGGGTAGCGGCCGCGCTGTCGACGATTACAAAGAC3'

FasL#3F:
5'AGAAAAAAAGGAGCTGAGGAAAGTGG3'

FasL#4F:
5'GGGGCGGATCCGAAAAAAAGGAGCTGAGGAAAGTGG3'

FasL#5R:
5'GGGGCCTCTAGAATCGATGGTCAGAGCTTATATAAGCCGAAAAACGTC
TG3'

HA-IF
5'CGCCAT GGCTATCATC TACCTCATCC TCCTGTTTCAC
CGCTGTGCGG GGAGC3'

HA-IIR
5'GGC CGC TGC CCC GCA CAG CGG TGA ACA GGA GGA TGA
GGT AGA TGA TAG CCA TGG CGG TAC3'
```

III. scTRAIL Cloning and Preparation of scTRAIL AMAIZe Constructs

The standard conditions given in Example 1 were used for the following clonings.

1. PCR with primers TRAIL#1 and TRAIL#2 on the template pcDNA3-sc40-TRAIL (see German Patent Application DE 10045591.3). PCR product 1 was cut with EcoRI and XbaI and ligated into the pcDNA3-scFasL vector digested with the same restriction enzymes. This digestion deleted the FasL sequence, whereby the HA and Flag tag sequence was retained and the following construct was now formed:

HA sequence-Flag tag-TRAIL module1-linker1-BamHI-XbaI

2. Using the primers TRAIL#1R and TRAIL#2F, PCR product 2 was generated with the template TRAIL-AMAIZE (see German Patent Application DE 10045591.3). This was cut only with XbaI, a blunt end and a sticky end forming. The construct from Step 1 was digested with BamHI and then treated with the Klenow enzyme, so that the ends were filled. After this, an XbaI digestion was performed and the PCR product 2 was cloned in this vector. The result was the following construct: HA sequence-Flag tag-TRAIL module1-linker1-TRAIL module2-linker2-BamHI-XbaI 3. For the cloning of TRAIL module 3, a PCR was carried out with the primers TRAIL#4 and TRAIL#5 on the template TRAIL-AMAIZe, the product was then digested with BamHI and XbaI, and cloned in the construct from Step 2—also digested with BamHI and XbaI, as a result of which the following construct formed:

HA sequence-Flag tag-TRAIL module1-linker1-TRAIL module2-linker2-TRAIL module3 Stop-XbaI For the preparation of the scTRAIL-AMAIZe constructs, the specific scTRAIL vectors were digested with the restriction enzymes NotI or EcoRI and XbaI and the inserts were inserted as cassettes into the corresponding AMAIZe vectors (see German Patent Application DE 10045591.3), whereby these vectors were also cut with the enzymes NotI or EcoRI and XbaI. The following constructs were prepared in this way:

HA svFv40-Flag tag-TRAIL module1-linker1-TRAIL module2-linker2-TRAIL module3

The sequences of the employed primers are given below:
Primers for the scTRAIL cloning (SEQ. ID NOs: 20-24)

```
TRAIL#1R:
5'ATCGATTTCTAGACCCGGGGGATCCGCCACCAGAACCGCCACCAGAAC
CGCCACCAGAACCGCCACCGCCAACTAAAAAGGCCCCGAAAAAACTGGCT
T-CATGGTC3'

TRAIL#2F:
5'GGGGTAGAATTCGGAACCTCTGAGGAAACCATTTCTACAGTTCAAG3'

TRAIL#3F:
5'AACCTCTGAGGAAACCATTTCTACAG3'

TRAIL#4F:
5'GGGGCGGATCCACCTCTGAGGAAACCATTTCTACAG3'

TRAIL#5R:
5'GGGGCCTCTAGAATCGATGGTCAGCCAACTAAAAAGGCCCCGAAAAAA
CTGGC3'
```

Example 2

Pharmacokinetics of Human Wild-Type TNF and Human scTNF

Six-week-old Balb/c mice were injected i.v. with 12 μg of TNF or scTNF (3 mice in each case). Blood was taken every 45 minutes and collected, and the concentration of TNF in the serum was determined using a human TNF-specific ELISA kit. The data in FIG. 27 show a clear increase in the in vivo half-life of the scTNF variants. It is therefore expected for scTNF that it has a clearly increased duration of biological action in vivo, which thereby emphasizes the value of scTNF as a potential therapeutic agent.

Example 3

CysHis-scTNF Coupled Covalently to Particles (Silica)

Mouse fibroblasts, transfected with the construct TNFR2-Fas, were treated with serial dilutions of the indicated reagents. These cells are completely resistant to soluble wtTNF. After covalent coupling of reduced CysHis-scTNF to silica microparticles (beads) according to established protocols (DPA 2001, No. DE 10144252), these cause a strong cytotoxic response (circle), like a positive control consisting of CysHis-scTNF and a TNFR2 cross-linking antibody, mAk 80M2 (triangle). Cys-His scTNF, which is not coupled, as expected shows no activity on TNFR2 positive cells (squares). Covalently coupled CysHis-scTNF is bioactive and possesses the special activity of membrane-bound TNF; i.e., it activates TNFR2.

Example 4

Comparison of Standard Recombinant Human (Rh)TNF and scTNF in In Vivo Tumor Necrosis Models and In Vitro L929 Cytotoxicity Activity Mice: C3H/HeJ (female), 17-19 g, from Charles River
Tumor cells: CFS-1 methylcholanthrene-induced fibrosarcoma cell line derived from C3H/HeN mouse (reference: Hafner M., P. Orosz, A. Krüger, and D. N. Männel. 1996 TNF promotes metastasis by impairing natural killer cell activity. *Internat. J. Cancer* 66:388-392).

Tumor necrosis experiment: The mice received $1.6 \times 10^7$ CFS-1 cells in 50 μL of medium (RPMI, 10% FCS) intradermally in the back; the tumors were allowed to grow for 12 days until they reached a size of about 5-6 mm in diameter, before the intraperitoneal injection of TNF (10 μg per mouse) in 200 μL of PBS or PBS alone as control. The tumor size was measured daily and examined grossly. The mice were sacrificed on Day 6 after the treatment and the tumors were removed for histology. The tumors were excised, fixed overnight in 4% PBS-buffered formalin, and embedded in paraffin. Equatorial vertical sections (4 μm) were stained with hematoxylin and eosin, and examined microscopically for necrosis (as described, e.g., in: Lucas R. et al., 2001, Int J Cancer, 91:543-549).

TNF: rhTNF specific activity $6.6 \times 10^6$ U/mg (48-hour L929 test without Act D) scTNF In vitro experiment, $LD_{50}$ activity in the L929 cytotoxicity assay with Act D for:
rhTNF=391 pg/mL
scTNF=39 pg/mL
(tested with the same TNF samples, which were used for in vivo experiments) scTNF in this in vitro experiment shows a 10-fold increased activity.

In Vivo Tumor Necrosis Experiment:

| | | | | | Necrosis | |
|---|---|---|---|---|---|---|
| | | Tumor diameter | | | microscopic** | |
| Group | n | d0 | d4 | gross* | <5% | >10% |
| PBS | 6 | 5.2 + 1 | 7.4 + 0.5 | 1 | 2 | 0 |
| rhTNF | 7 | 5.2 + 0.9 | 6.6 + 1.7 | 3 | 6 | 1 |
| scTNF | 7 | 5.9 + 0.5 | 7.3 + 0.3 | 5 | 0 | 7 |

*= grossly clearly discernible superficial necrosis
**= on microscopic examination, central hemorrhagic necrosis, <5% or >10% of the tumor tissue

CONCLUSION

After 4 days of treatment with single doses, there was no difference in the tumor size (for an overview on TNF as a tumor therapeutic agent, see, e.g., Eggermont et al, Lancet Oncol. 4, 429 (2003)).

rhTNF induced small hemorrhagic necrosis (<5% of the tumor area), visible grossly in only 3/7 of the animals.

scTNF induced larger hemorrhagic necroses (>10% of the tumor area) in all tumors (7/7), 5/7 of which can be seen grossly.

seTNF>>rhTNF in relation to tumor cytotoxicity in vitro and induction of necrosis.

The invention claimed is:

1. A method for extracorporeal depletion or removal of tumor necrosis factor receptor (TNFR) from blood or blood fractions comprising the following steps:
   a) Optional separation of the blood into one or more blood fractions with solid or liquid components;
   b) Binding of the blood or the blood fractions expressing a TNFR to a surface or particle coupled to a polypeptide wherein the polypeptide comprises at least three components A and at least two components B, wherein each component A comprises a tumor necrosis factor (TNF) monomer or a functional fragment or a functional variant thereof, and each component B is a peptide linker under conditions allowing binding of TNFR in the blood or the blood fractions to the surface or the particle; and
   c) Separating the bound TNFR from the blood or the blood fractions, thereby depleting or removing TNFR from the blood or the blood fractions.

2. The method according to claim 1, wherein before step a) or b) blood is taken from a patient.

3. The method according to claim 1, wherein after a step b) or c), the blood or blood fraction is injected or reinjected into a patient.

4. The method according to claim 1, wherein components A are identical or different.

5. The method according to claim 1, wherein the blood or the blood fraction is from the same organism or different organisms.

6. The method according to claim 1, wherein components B each link together two of the at least three components A.

7. The method according to claim 1, wherein at least one of components B has the amino acid sequence (GGGS)$_3$ (SEQ ID NO:2) or (GGGS)$_4$ (SEQ ID NO:3).

8. The method according to claim 1, wherein components A and components B form a trimeric protein structure.

9. The method according to claim 8, wherein components A and components B form a homotrimeric protein structure.

10. The method according to claim 8, wherein components A and components B form a heterotrimeric protein structure.

11. The method according to claim 1, wherein components B are identical or different.

12. The method according to claim 1, wherein components B are from the same organism or different organisms.

13. The method according to claim 1, wherein the polypeptide has an N-terminal tag sequence.

14. The method according to claim 13, wherein the N-terminal tag sequence is a His tag sequence or a Flag tag sequence.

15. The method according to claim 1, wherein the polypeptide has an N-terminal leader peptide sequence.

16. The method according to claim 1, wherein the polypeptide further comprises component C, wherein component C comprises an antibody fragment or a different protein or peptide, which selectively recognizes a specific target molecule on a cell surface.

17. The method according to claim 16, wherein component C is an antibody fragment from a mammal.

18. The method according to claim 17, wherein the mammal is human.

19. The method according to claim 17, wherein the antibody fragment is a humanized antibody fragment.

20. The method according to claim 16, wherein the antibody fragment comprises scFv.

21. The method according to claim 1, wherein at least one component A comprises a soluble tumor necrosis factor (TNF) monomer.

22. The method according to claim 1, wherein each component A comprises a soluble tumor necrosis factor (TNF) monomer.

23. The method according to claim 1, wherein the polypeptide is coupled to the surface or particle by a cysteine residue in the first 1-15 N-terminal amino acids of the polypeptide.

* * * * *